US010898122B2

(12) United States Patent
Torres

(10) Patent No.: US 10,898,122 B2
(45) Date of Patent: Jan. 26, 2021

(54) SYSTEM AND METHOD FOR MEASURING PHYSIOLOGICALLY RELEVANT MOTION

(71) Applicant: Rutgers, The State University of New Jersey, New Brunswick, NJ (US)

(72) Inventor: Elizabeth B. Torres, Piscataway, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 224 days.

(21) Appl. No.: 15/617,822

(22) Filed: Jun. 8, 2017

(65) Prior Publication Data

US 2017/0340261 A1    Nov. 30, 2017

Related U.S. Application Data

(63) Continuation-in-part of application No. PCT/US2015/064440, filed on Dec. 8, 2015.

(60) Provisional application No. 62/089,031, filed on Dec. 8, 2014.

(51) Int. Cl.
| | |
|---|---|
| *A61B 5/00* | (2006.01) |
| *A61B 5/11* | (2006.01) |
| *A61B 5/01* | (2006.01) |
| *A61B 5/024* | (2006.01) |
| *A61B 5/0476* | (2006.01) |
| *A61B 5/0488* | (2006.01) |

(52) U.S. Cl.
CPC .......... *A61B 5/4082* (2013.01); *A61B 5/1101* (2013.01); *A61B 5/721* (2013.01); *A61B 5/01* (2013.01); *A61B 5/024* (2013.01); *A61B 5/0476* (2013.01); *A61B 5/0488* (2013.01); *A61B 5/459* (2013.01)

(58) Field of Classification Search
None
See application file for complete search history.

(56) References Cited

U.S. PATENT DOCUMENTS

| 8,121,694 B2 | 2/2012 | Molnar et al. | |
|---|---|---|---|
| 9,615,547 B2 * | 4/2017 | Menkes | A61B 5/1105 |
| 2003/0105409 A1 | 6/2003 | Donoghue et al. | |

(Continued)

FOREIGN PATENT DOCUMENTS

| WO | WO-2013071285 A1 * | 5/2013 | ............... A61B 5/11 |

*Primary Examiner* — Matthew Kremer
*Assistant Examiner* — Samuel C Kim
(74) *Attorney, Agent, or Firm* — Wolter Van Dyke Davis, PLLC; Eugene J. Molinelli

(57) ABSTRACT

A system for measuring and monitoring physiologically relevant motion of a subject includes at least a motion sensor to measure movement of the subject and produce a series of movement data representing the movement of the subject over a period of time. The system also includes at least a biometric sensor to simultaneously measure biometrics of the subject and produce a series of biometric values of the subject over the period of time. The system is configured to determine a noise-to-signal ratio for the series of movement data as a function of biometric intervals in the series of biometric values and identify at least a portion of the series of movement data as corresponding to a physiologically relevant biorhythm. The system can be used to diagnose and monitor a disease or disorder, including a neurological disorder or a traumatic brain injury.

23 Claims, 40 Drawing Sheets

(56) References Cited

U.S. PATENT DOCUMENTS

| | | | |
|---|---|---|---|
| 2004/0138540 A1* | 7/2004 | Baker, Jr. | A61B 5/024 600/336 |
| 2005/0143589 A1* | 6/2005 | Donoghue | A61B 5/04001 552/650 |
| 2005/0165327 A1 | 7/2005 | Thibault et al. | |
| 2007/0280508 A1* | 12/2007 | Ernst | G06K 9/00624 382/107 |
| 2008/0001735 A1 | 1/2008 | Tran | |
| 2011/0066381 A1* | 3/2011 | Garudadri | A61B 5/0002 702/19 |
| 2011/0270104 A1* | 11/2011 | Stadler | A61B 5/0464 600/515 |
| 2014/0070957 A1* | 3/2014 | Longinotti-Buitoni | A61B 5/6804 340/870.01 |
| 2014/0123912 A1* | 5/2014 | Menkes | A61B 5/1118 119/859 |
| 2014/0336539 A1 | 11/2014 | Torres et al. | |
| 2015/0190096 A1* | 7/2015 | Zong | A61B 5/721 600/301 |

* cited by examiner

Noise to Signal Ratio from Max Acceleration

RIGHT WRIST DATA

LEFT WRIST DATA

SYSTEM AND METHOD FOR MEASURING PHYSIOLOGICALLY RELEVANT MOTION

RELATED APPLICATIONS

This patent application is a continuation-in-part of International Application Number PCT/US2015/064440 filed Dec. 8, 2015, which claims priority under 35 U.S.C. 119(e) to U.S. Patent Ser. No. 62/089,031 filed on Dec. 8, 2014. The content of the above applications are incorporated by reference in their entirety.

BACKGROUND

This patent disclosure relates generally to systems and methods for measuring and monitoring physiologically relevant motion, particularly, with respect to diagnosing and/or monitoring a disease or disorder, such as a neurological disorder or a traumatic brain injury, in a subject.

Several publications and patent documents are cited throughout the specification in order to describe the state of the art to which this invention pertains. Each of these citations is incorporated herein by reference as though set forth in full.

According to the Centers for Disease Control (CDC) severe traumatic brain injury (sTBI) is a contributing factor to a third (30%) of all injury-related deaths in the US (Carroll et al. (2012) Neurosurgery 71:1064-70; CDC (2013) MMWR 62:549-52), thus posing a large societal and economic toll (Finkelstein et al. (2006) The incidence and economic burden of injuries in the United States. New York: Oxford University Press). Non-fatal sTBI may result in immediate unconsciousness (coma) and amnesia states followed by slow recovery with subsequent extended periods of impairments in one or more general functional areas. These may include impaired cognitive and/or motor functions as well as impaired sensations and/or emotional responses. Physicians and researchers now generally recognize that the spectrum of disorders related to coma can be more broadly defined as a range of disorders of consciousness (DOC) that can be mapped onto a multi-dimensional space primarily defined by cognitive and motor impairments.

In many cases the initial coma state may evolve towards improved levels of consciousness and physical function such as a minimally conscious state (MCS). To assess coma and impaired consciousness in the early stages of TBI there are several clinical tools based on reports from observation. These include the Glasgow Coma Scale (GCS), Coma Recovery Scale-Revised (CRS-R), the Abbreviated Injury Scale (AIS) and the Trauma Score or Abbreviated Trauma Score, among others. These observational tools can also be used to track progress while at the hospital or during subsequent visits, in cases where the patient improves and undergoes rehabilitation at home. Other tools used in the hospital settings include objective assessments of the brain condition using imaging techniques. The use of these techniques is however limited to a few times per year, due primarily to their cost and regional availability.

Upon recovery from the initial coma state, many patients undergo rehabilitation and eventually return home to be looked after by a caregiver and to continue receiving therapy. At that stage there are presently no objective tracking tools to help the caregivers and/or the occupational and physical therapists to assess the daily progression of the patient in response to treatments. The current assessments to track physical progress rely primarily on observation (e.g. the use of inventories such as the Western Neuro Sensory Stimulation Profile, WNSSP). Yet the human eye has limited capacity to detect subtle changes in physical motions that could signal improvement, or call for immediate attention to some sharp change in physiological states. Physicians and therapists look for eye opening to detect changes in arousal and behavioral command following and/or changes in spontaneous/reflexive movement to detect changes in awareness. Diagnoses of changes in states of awareness or arousal based on clinical observation alone have high rates of diagnostic error, approximately 40% (Schnakers et al. (2009) BMC Neurol., 9:35). Improved methods of diagnosing and monitoring are clearly needed.

SUMMARY

A system for measuring and monitoring physiologically relevant motion of a subject includes at least a motion sensor to measure movement of the subject and produce a series of movement data representing the movement of the subject over a period of time. The system also includes at least a biometric sensor to simultaneously measure biometrics of the subject and produce a series of biometric values of the subject over the period of time. The motion sensor can be an inertial measure unit (IMU) sensor attachable to a body part of the subject or a functional magnetic resonance imaging (fMRI) device to collect a sequence of images of the head of the subject over the period of time. The biometric sensor can be one of the following: a thermometer, an electroencephalogram (EEG), an electromyography (EMG), a stethoscope or a heart rate monitor.

The system also includes a processing device and a non-transitory computer readable medium containing programming instructions that cause the processing device to determine a noise-to-signal ratio for the series of movement data as a function of biometric intervals in the series of biometric values and identify at least a portion of the series of movement data as corresponding to a physiologically relevant biorhythm. The system may also include additional programming instructions configured to cause the processing device to analyze motion fluctuation in the portion of the series of movement data that correspond to the physiologically relevant biorhythm to determine a rate of change of the noise-to-signal value for each biometric interval and use the rate of change to determine whether the physiological relevant biorhythm at each biometric interval is systematic or spontaneously random.

The system may estimate parameters of a continuous Gamma distribution family based on the portion of the series of movement data at each biometric interval and determine a shape parameter of the continuous Gamma distribution and a rate of change of the shape parameter of the continuous Gamma distribution.

Various methods can be implemented using the above described system. A method of identifying physiologically relevant biorhythm of the subject includes measuring, by the motion sensor, movement of the subject and producing a series of movement data representing the movement of the subject over a period of time. The method also includes measuring simultaneously, by the biometric sensor, biometrics of the subject and producing a series of biometric values of the subject over the period of time. The method also includes determining, by the processing device, the noise-to-signal ratio for the series of movement data as a function of biometric intervals in the series of biometric values and identifying at least a portion of the series of movement data as corresponding to a physiologically relevant biorhythm.

The method may further involves analyzing, by the processing device, motion fluctuation in the portion of the series of movement data that correspond to a physiologically relevant biorhythm to determine the rate of change of the noise-to-signal value for each biometric interval and using the rate of change to determine whether the physiological relevant biorhythm at each biometric interval is systematic or spontaneously random.

BRIEF DESCRIPTIONS OF THE DRAWING

Figure 4A:
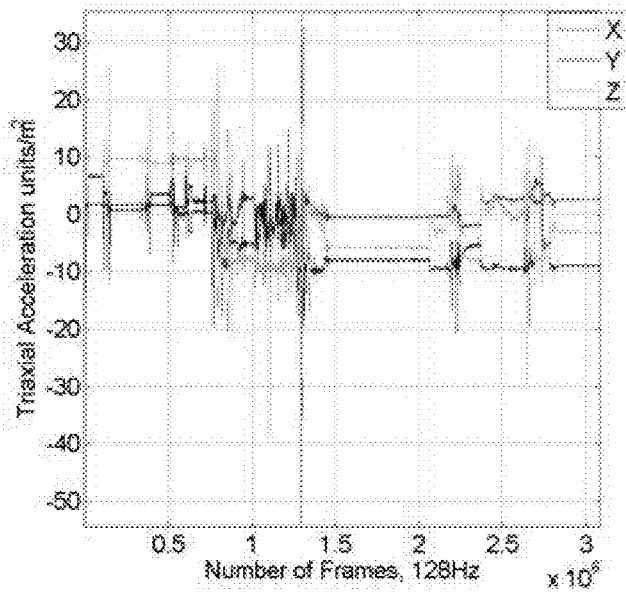
Figure 4B:
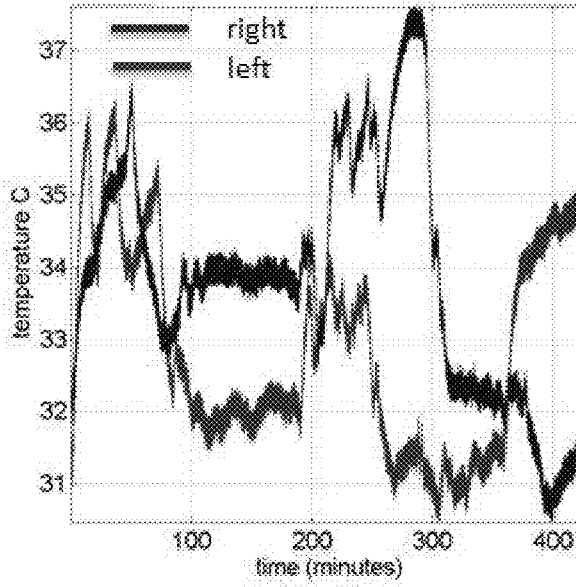
Figure 4C:
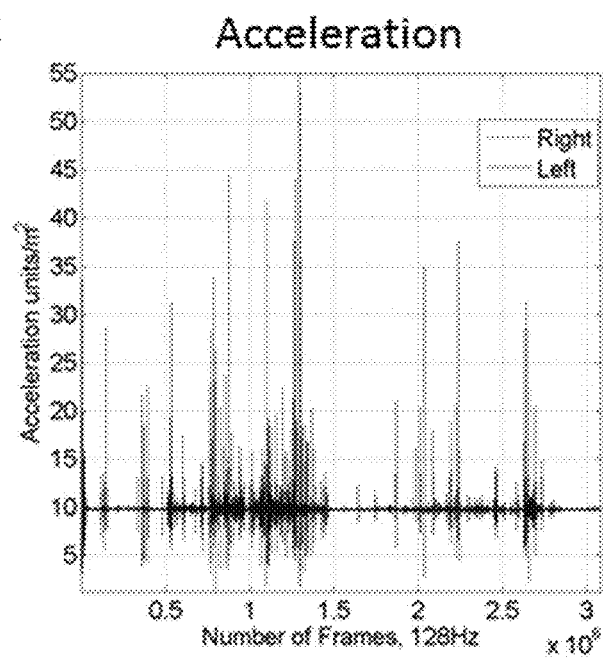
Figure 4D:
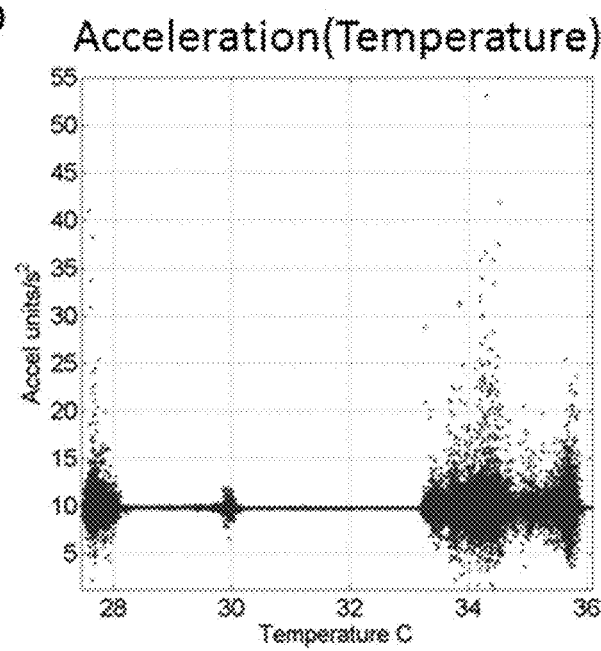
Figure 4E:
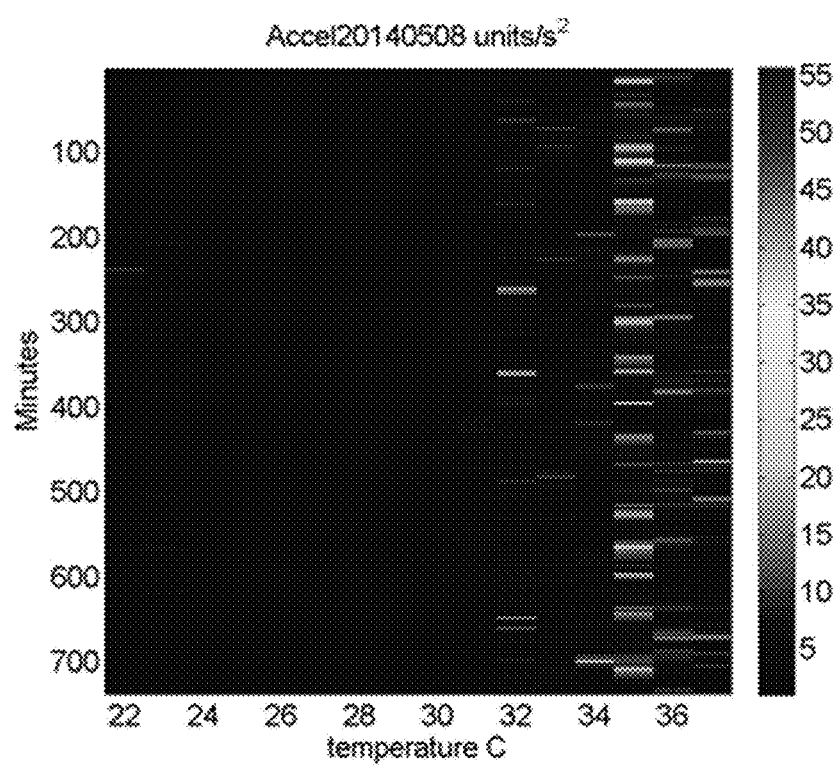

FIG. 4A shows the tri-axial acceleration measurements from one of the sensors during recording one session of 7.09 hours. FIG. 4B shows temperature measurements from both the left and right wrist sensors during the session. FIG. 4C shows acceleration scalar obtained by computing the norm of each acceleration vector over time. FIG. 4D shows acceleration plotted as a function of temperature (degree Celsius) for the full range of temperatures registered across the 7.09 hour session of Apr. 24, 2014. FIG. 4E shows a matrix of maximal deviations from the mean acceleration values registered on May 8, 2014 for the temperature range and time duration in minutes (for 12.28 hours). For each minute and ° C. the motion content was registered. The bar shows the range of the motion values (units/s$^2$). The range of changes in temperature values was registered between 22° C. and 38° C. for that day's recording session.

Figure 5:
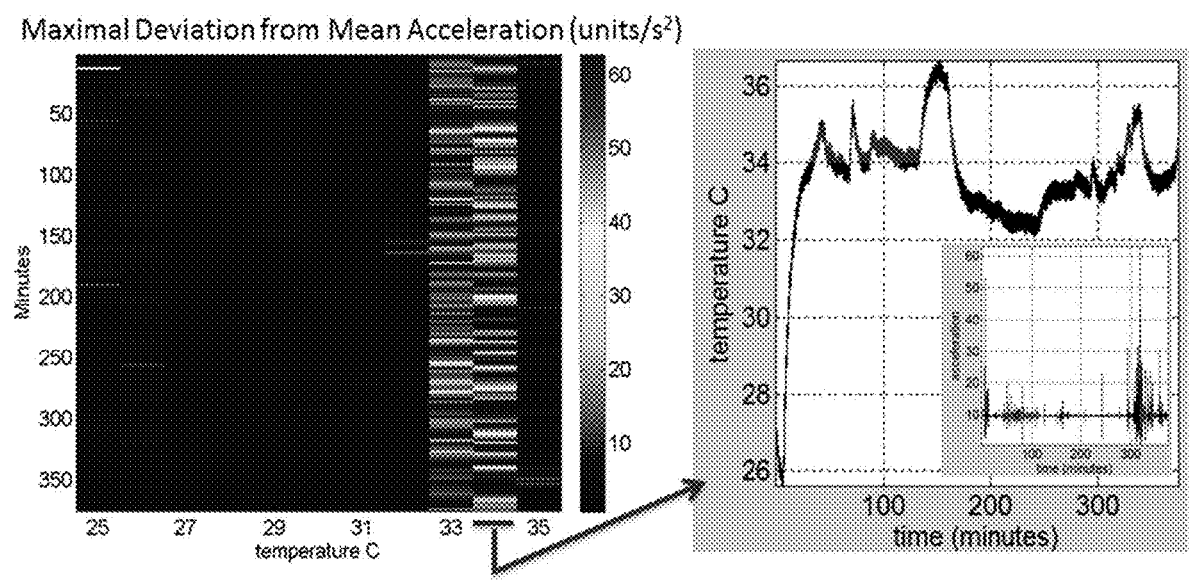

FIG. 5 shows the construction of the matrix containing the sensor data from a registered range of surface skin temperatures. Motion data from the tri-axial linear accelerometers are obtained continuously for each minute of recordings (128 Hz×60 frames) in 6.26 hours (375.6 minutes) for this session. Each entry of the matrix contains the maximal deviation from the mean acceleration at each ° C.-interval (columns) and for each minute (rows) of the session. The right panel shows the 34-35° C.-interval and the inset shows the linear acceleration data corresponding to that temperature ° C. interval. On the left panel the 34-35° C.-interval is marked to show the patterns of the maximal deviation from the mean acceleration over the session's time length.

Figure 6A:
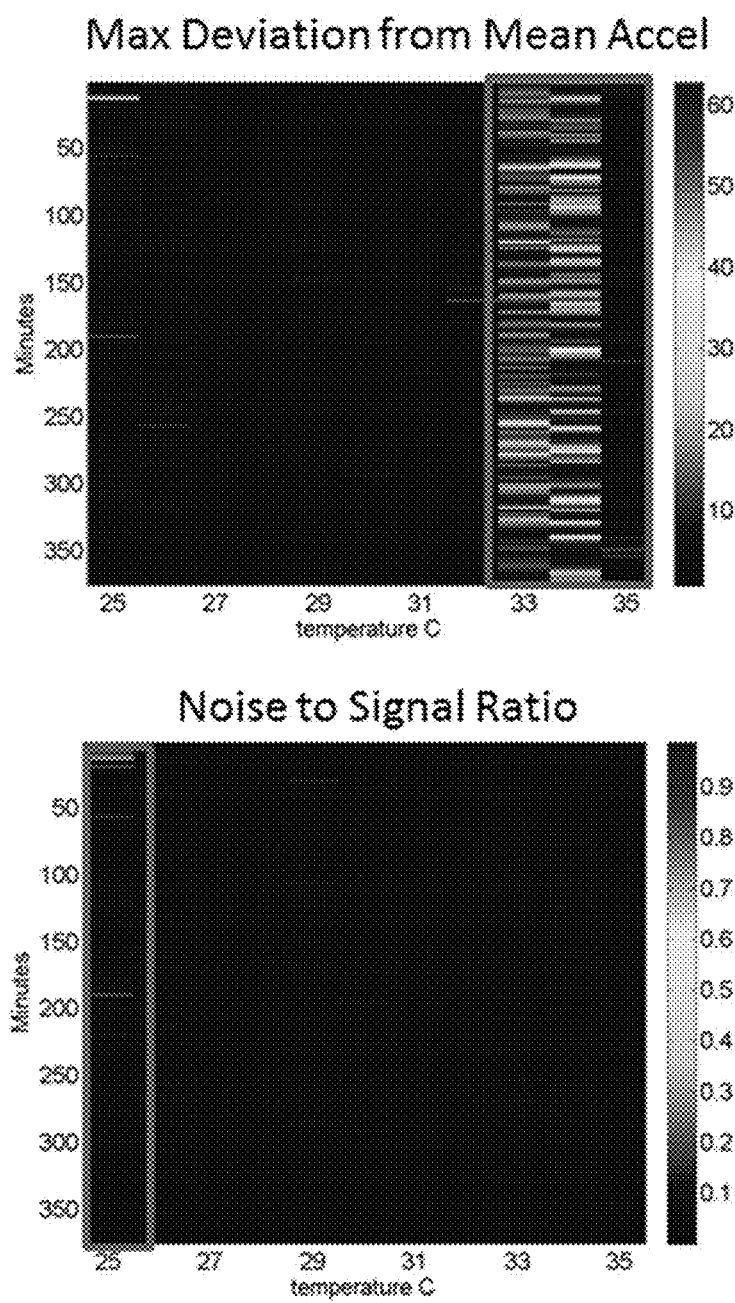
Figure 6B:
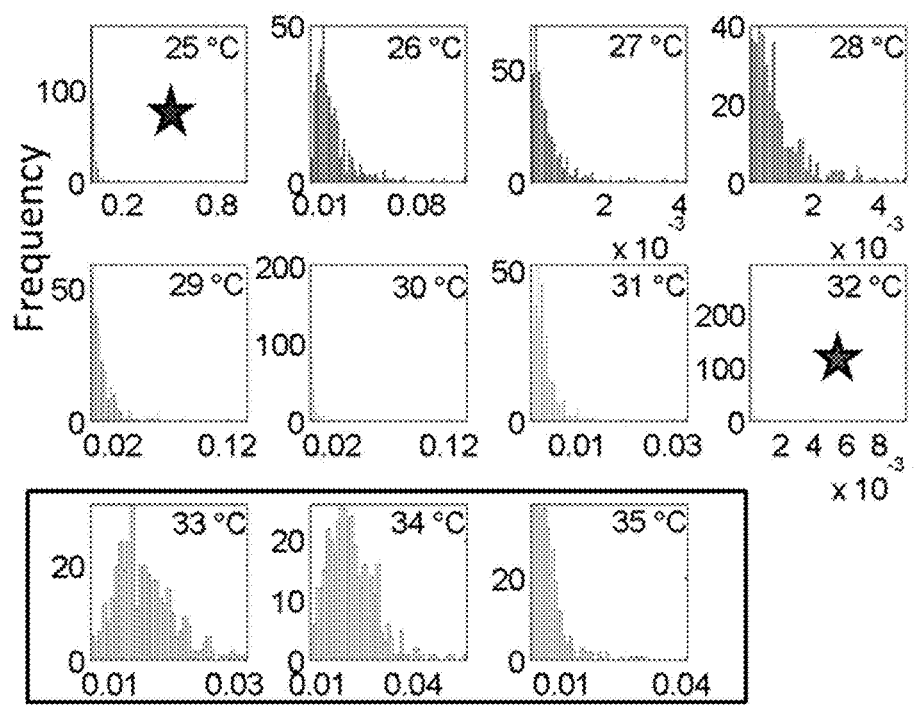
Figure 6C:
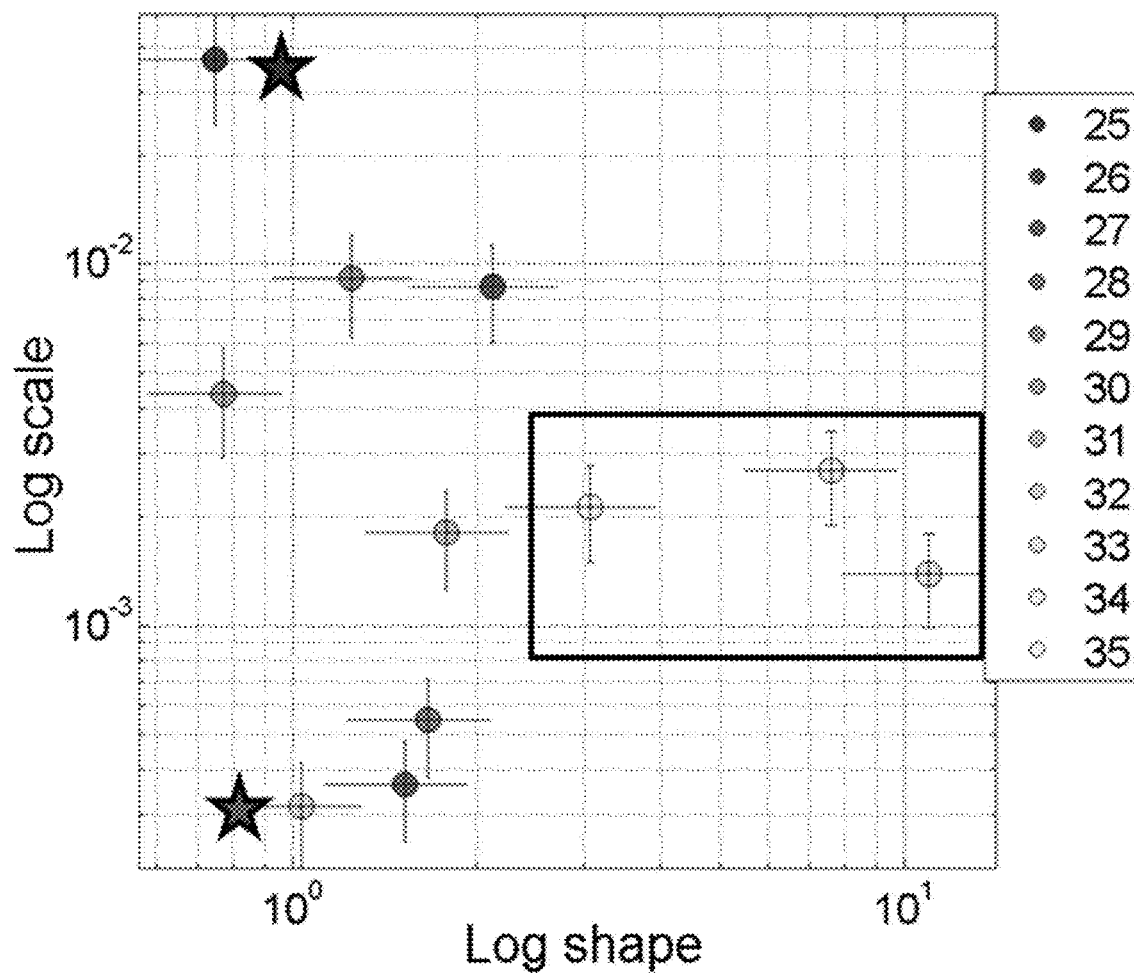

FIGS. 6A-6C show the noise analyses to separate predictable and reliable from random and noisy motion data. The minute by minute variability is obtained for the maximal deviations from the mean acceleration, taken for each ° C. interval. For FIG. 6A, the top panel is the matrix of maximal deviations from the mean linear acceleration (explained in FIG. 4) within the temperature regime of motions. The bottom panel is the matrix of the noise-to-signal ratio (the Fano Factor: the estimated Gamma variance divided by the estimated Gamma mean) obtained from the estimated shape and scale parameters of the continuous Gamma family of probability distributions. The highest motion regime occurs between 33° C. and 35° C. The highest noise regime occurs at 25° C. while the lowest noise regime occurs at 32° C. FIG. 6B: frequency histograms of the noise-to-signal values are coded in order of increasing temperature values. FIG. 6C provides a Gamma plane. The star marks the highest noise-to-signal regime and the lowest regime. The temperature intervals containing the highest motion patterns are enclosed by a rectangle. These correspond to the three right most points in the Gamma plane (most systematic patterns), also enclosed within a rectangle.

Figure 7:
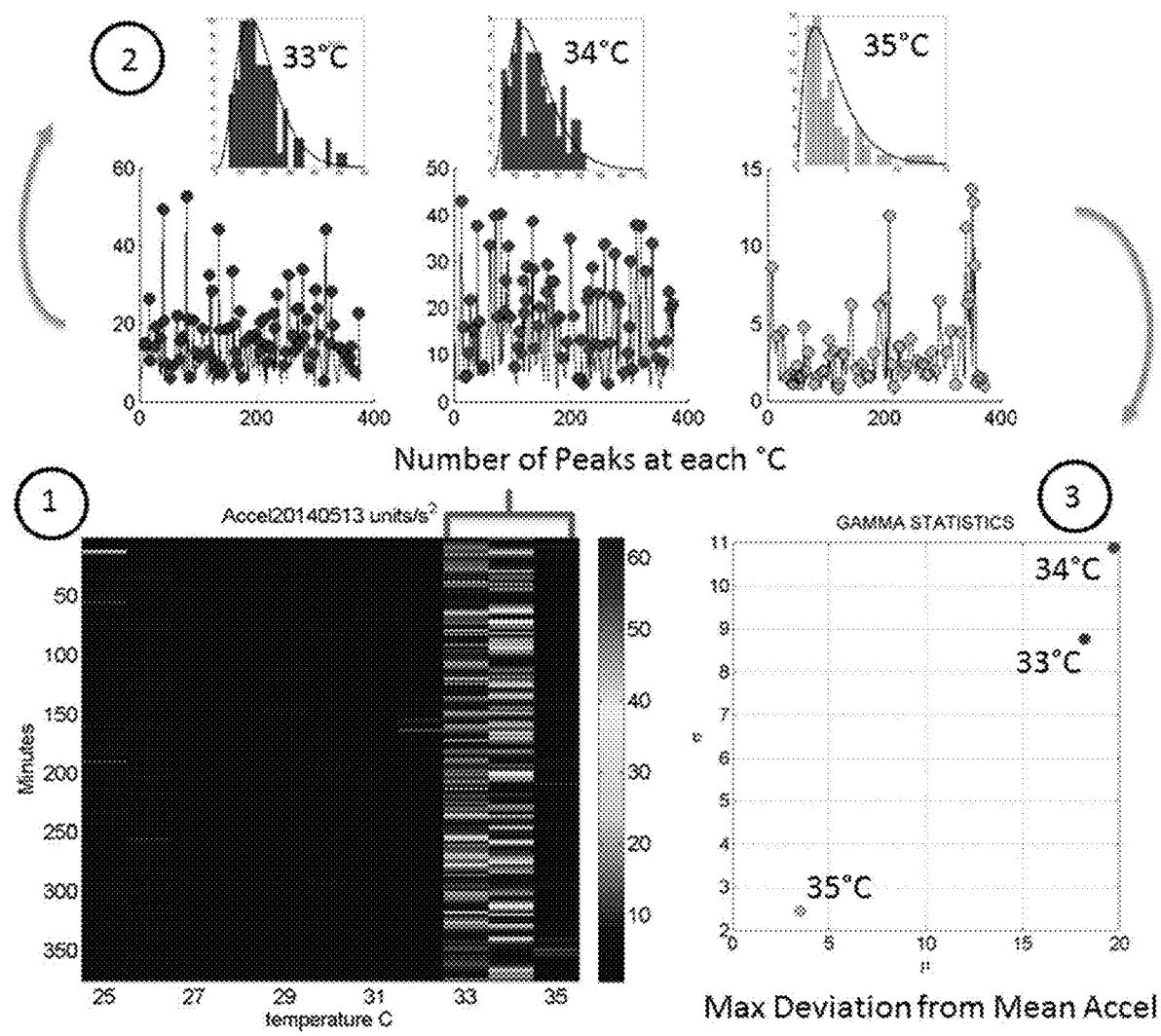

FIG. 7 shows the steps to analyze the patterns of acceleration variability. (1) Build the matrix having in each entry the maximal deviations from the mean acceleration, as described in FIG. 2, for each minute of the 6.26-hours session and each ° C.-interval of the surface skin temperature range registered. (2) For each column harness the peaks from the entries of the matrix with low and predictable noise-to-signal ratio. The frequency histogram of the peak deviations from the mean is obtained for each ° C. interval and the best fitting probability distribution function obtained. (3) Obtain the empirically estimated Gamma mean and Gamma variance from the experimental data using the estimates of the shape and scale Gamma parameters.

Figure 8A:
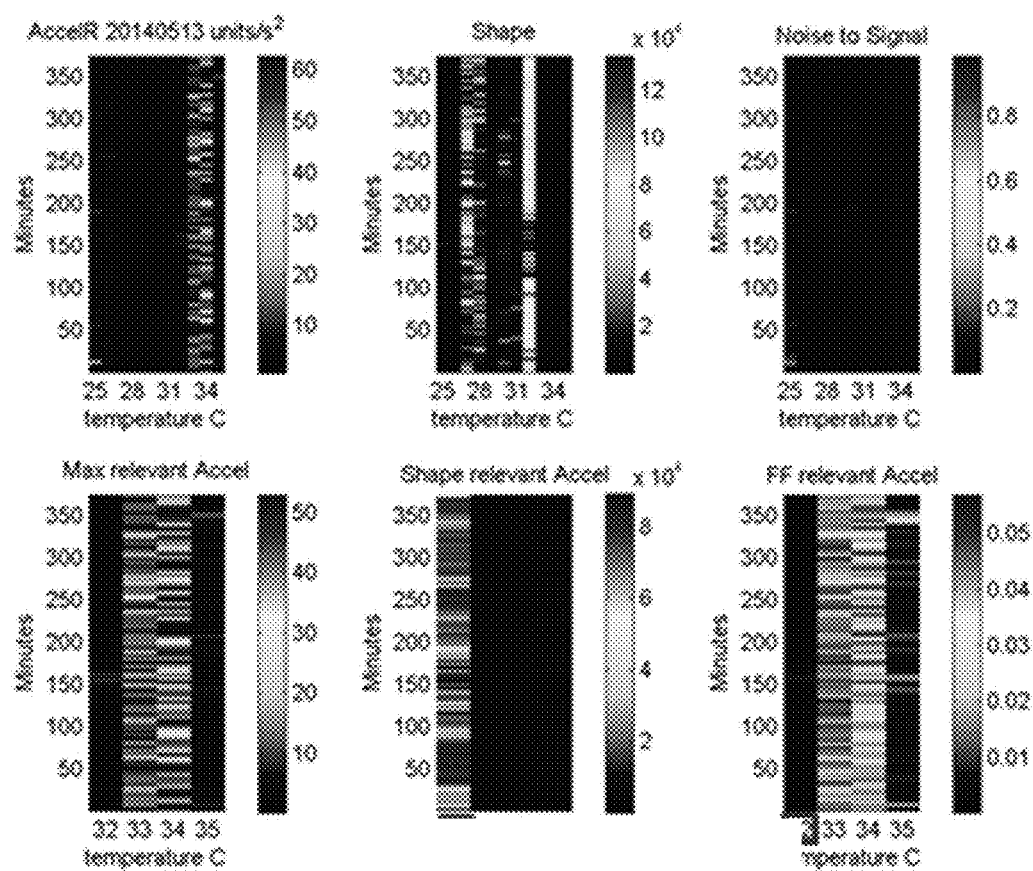
Figure 8B:
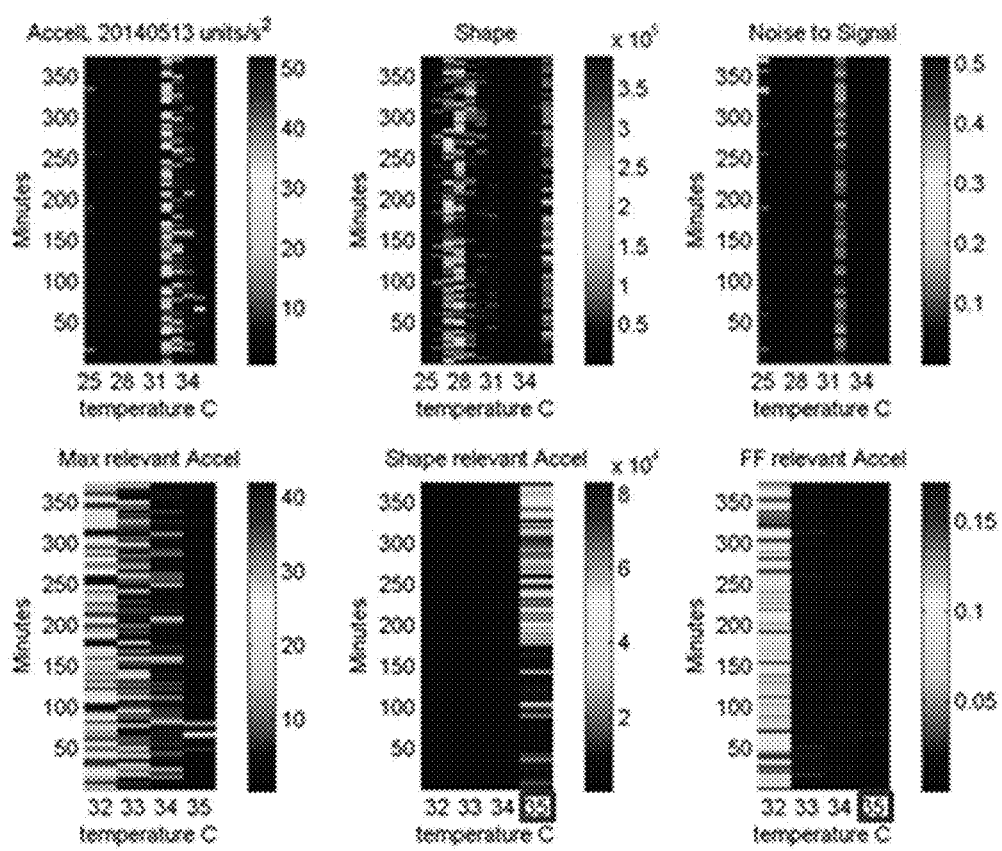

FIGS. 8A and 8B show the automatic extraction of physiologically relevant data. FIG. 8A: Right wrist accelerometer and temperature data represented in matrix form and coded by activity level in minute-by-minute intervals. As explained in FIG. 4, in the first panel each entry of the matrix represents the maximal deviation from the mean acceleration for each given minute and ° C. Scale represents motion intensity from low to high. In the second panel each entry of the matrix represents the values of the shape parameter of the continuous Gamma family of probability distributions estimated from acceleration data. Each (i,j)-entry is the shape estimate for the ith minute the jth ° C. Each entry in the third matrix, as explained in FIG. 5, has the Fano Factor, the noise-to-signal ratio from the estimated Gamma mean and variance parameters for the ith minute and the jth ° C. The lower panel contains the subset from the full range of surface skin temperature registered where the noise to signal is lower (minimal level enclosed by red square.) In FIG. 8A (the right wrist) minimal noise in the acceleration is at 32° C. (also the highest shape value, indicating most symmetric distribution of the motion parameter). In FIG. 8B (the left wrist) the noise-to-signal is low for 32-35° C., with 35° C. having the lowest noise-to-signal regimes and the most systematic motions indicated by the higher values of the shape parameter.

Figure 9A:
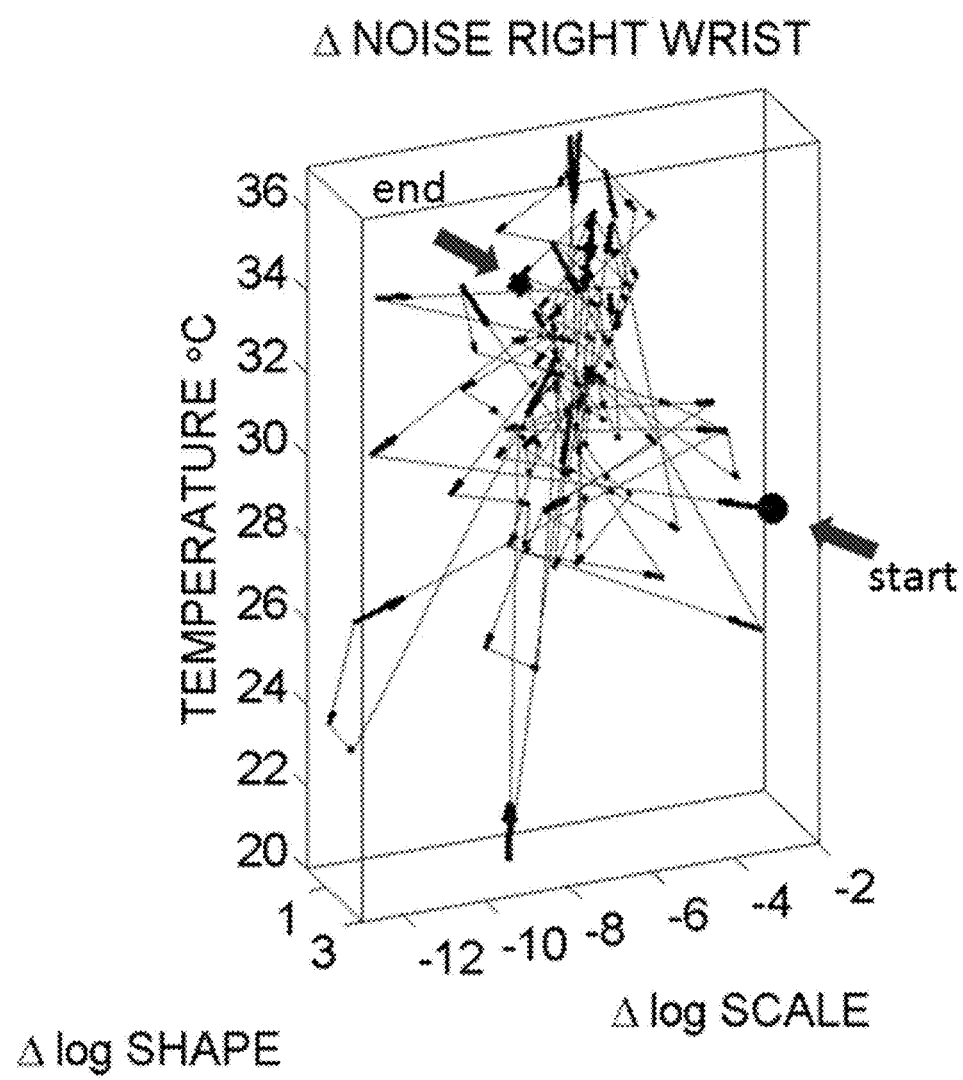
Figure 9B:
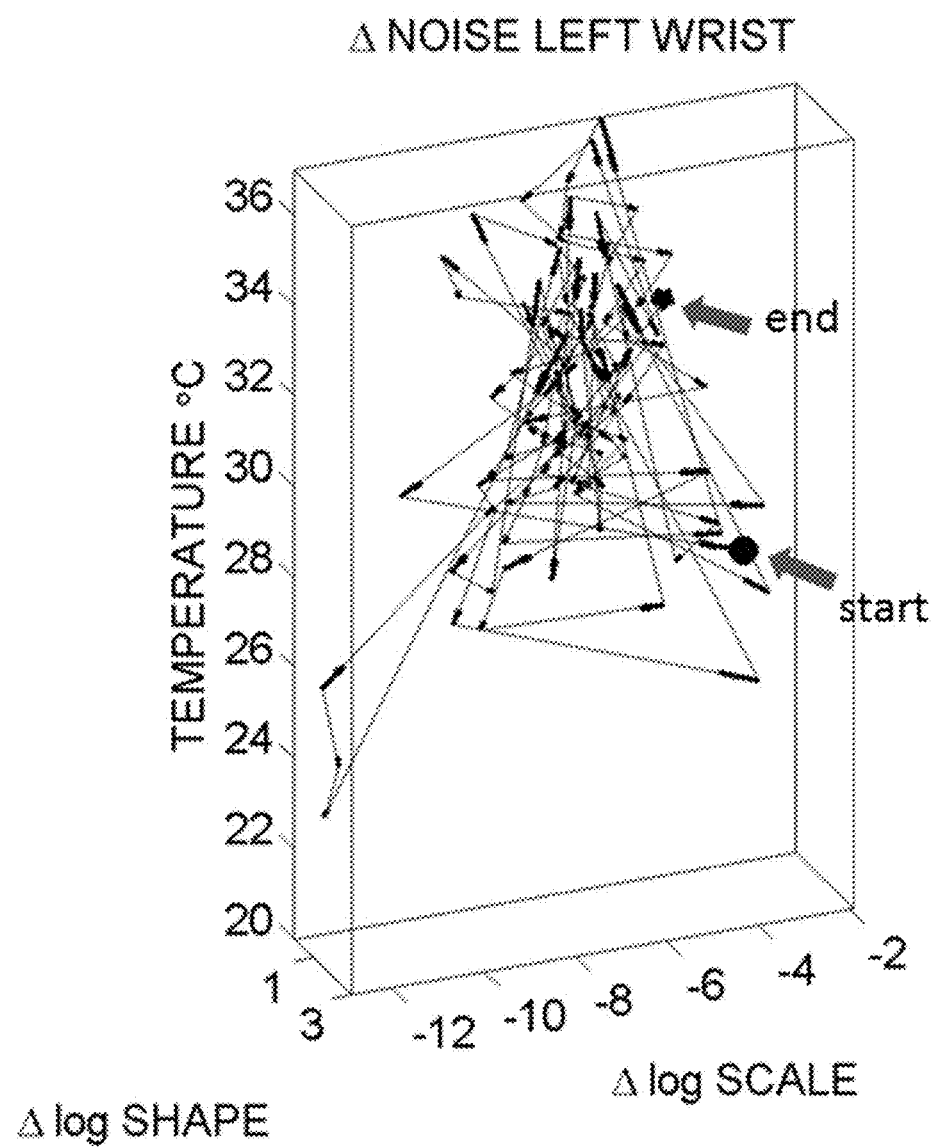
Figure 9C:
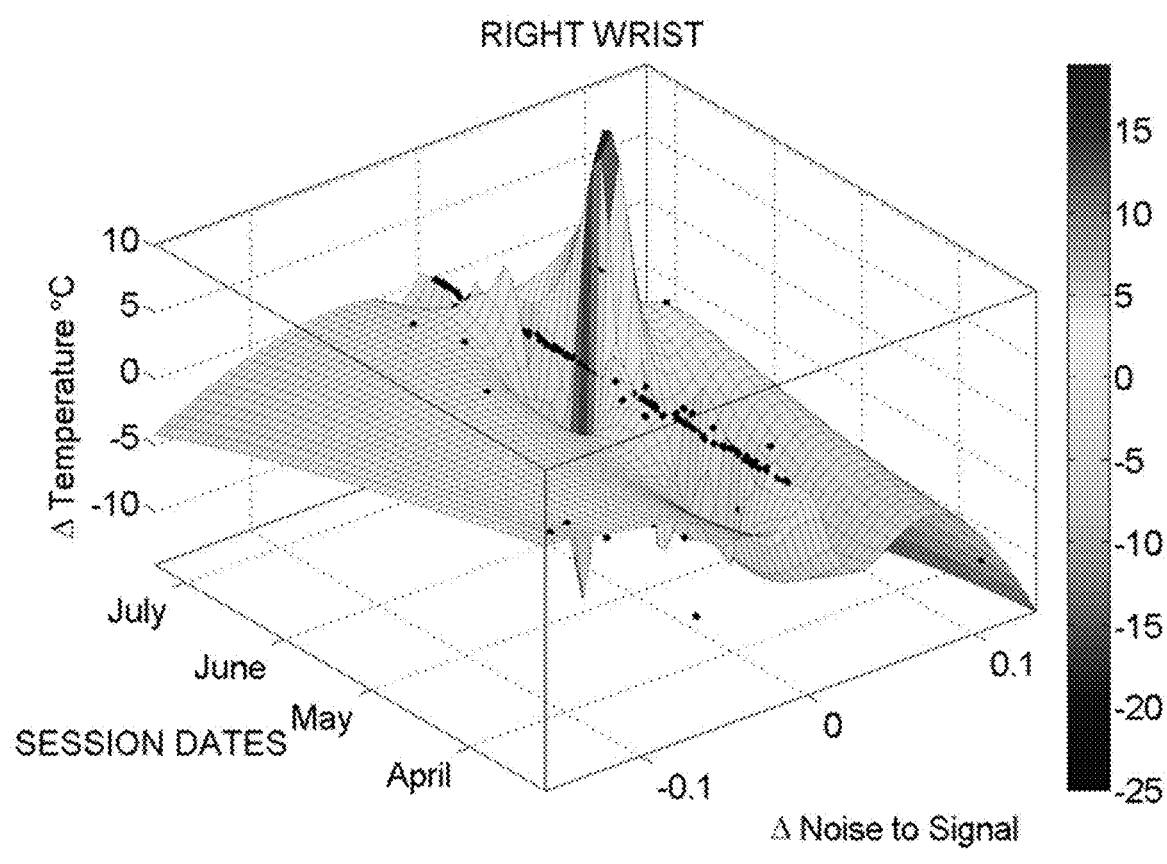
Figure 9D:
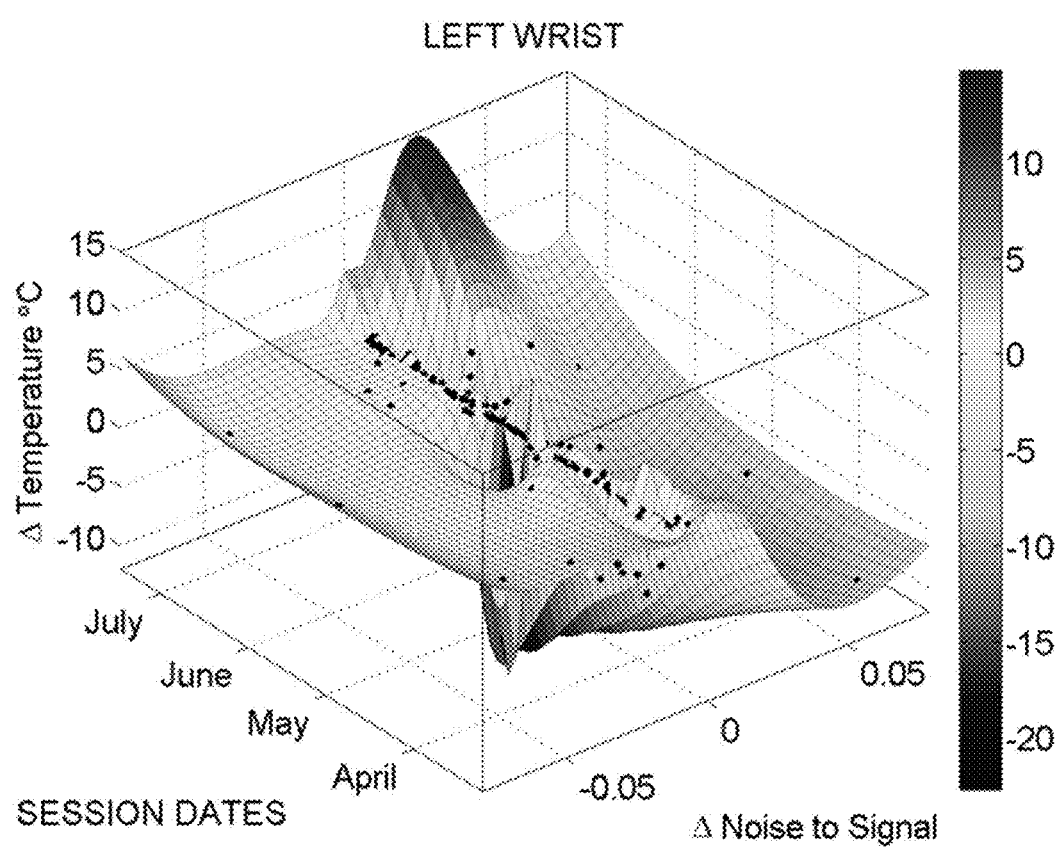

FIGS. 9A and 9B show the longitudinal changes in temperature and noise-to-signal ratio. FIG. 9A: Stochastic trajectories of the right wrist variability in the acceleration data registered within the range of temperature with the lowest noise-to-signal ratio. Arrows show the flow of directional change towards stable temperature regimes of low changes in the noise of the motion. This is marked by the size of the arrows from large at low temperature to small at higher temperature values (between 32-34° C.). The starting and ending points of the stochastic trajectories are marked. FIG. 9B: Same as in FIG. 9A for the left wrist. FIG. 9C: Surface fit through 124 points from the motion data longitudinally obtained from the right wrist. These are the data with the lowest noise level in the maximal deviations from the mean acceleration. Notice that the area showing the sharpest rate of change in temperature and noise-to-signal levels was registered in May. FIG. 9D: The surface fitting the 124 longitudinal data points from the left wrist shows decrease in the rate of change of temperature in May, followed by a gradually slow increase of this parameter across the subsequent months of June and July. In both cases there are also points aligned at near zero-change in noise-to-signal ratio for the motion. These are the points where the signatures of variability in the motion patterns registered by the sensors were more stable and had more steady state of temperature levels as well.

Figure 10A:
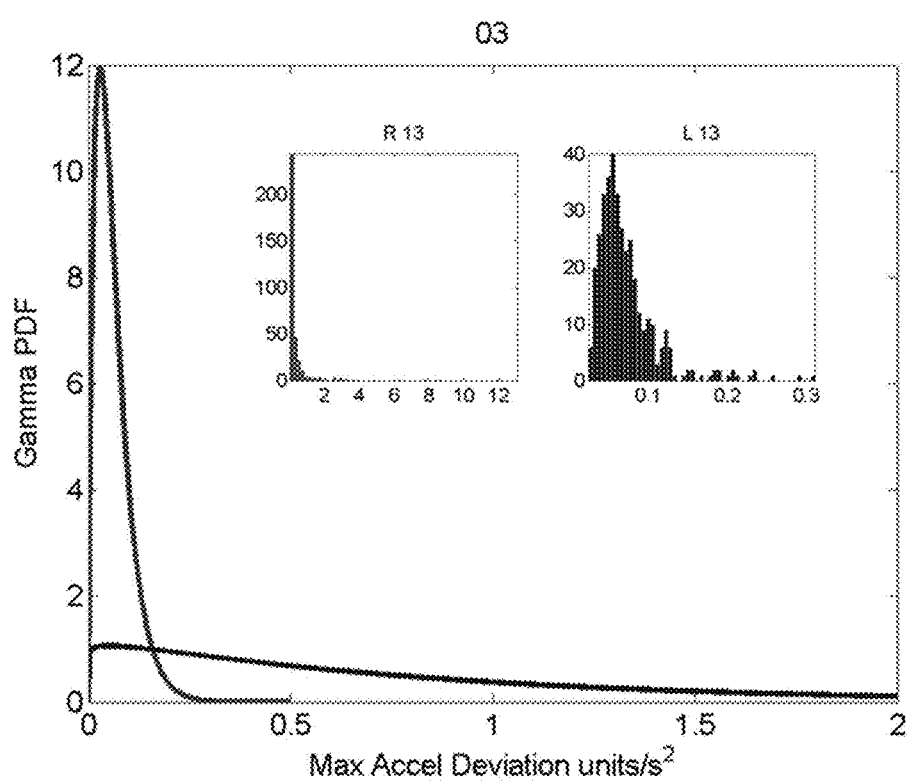
Figure 10B:
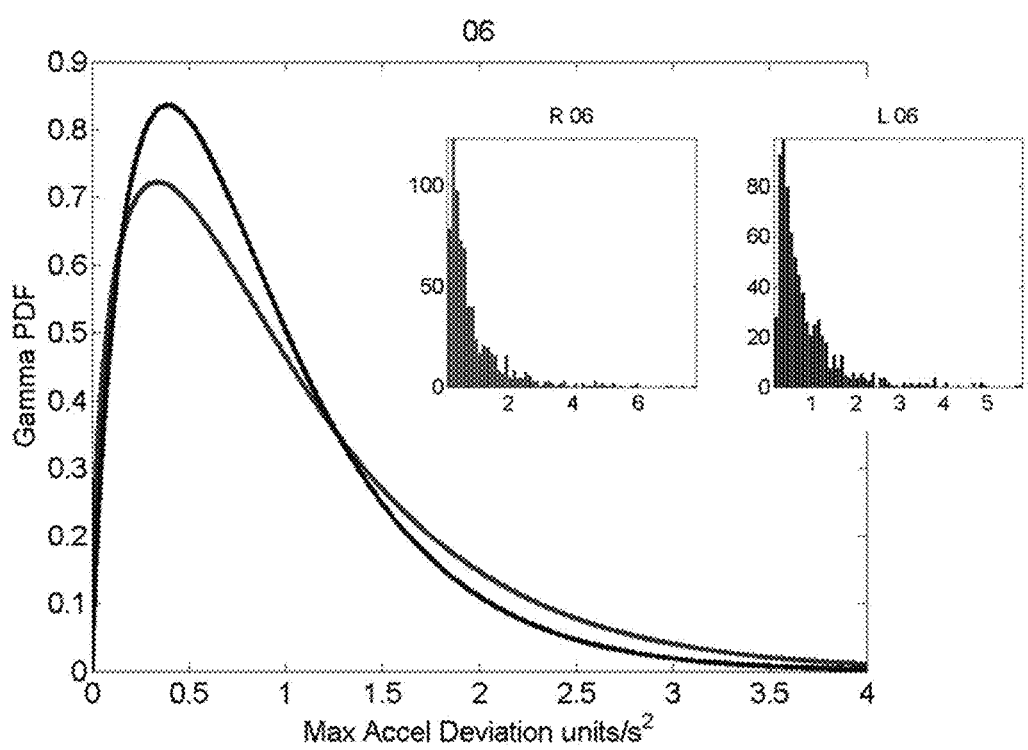
Figure 10C:
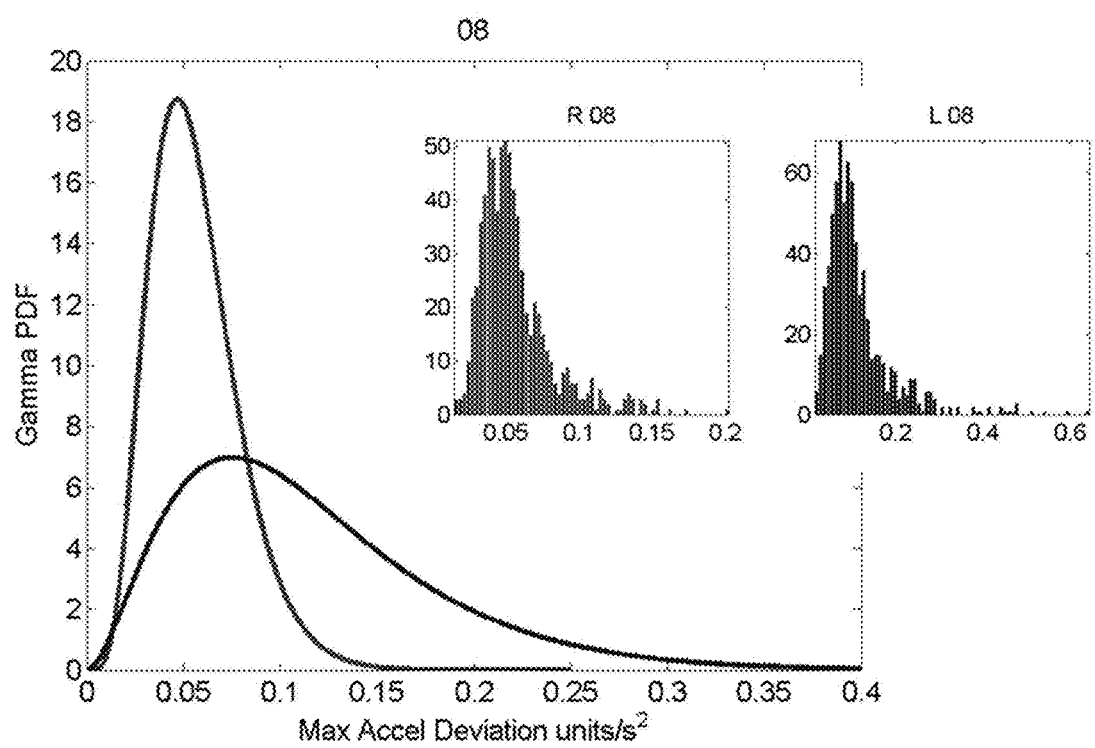
Figure 10D:
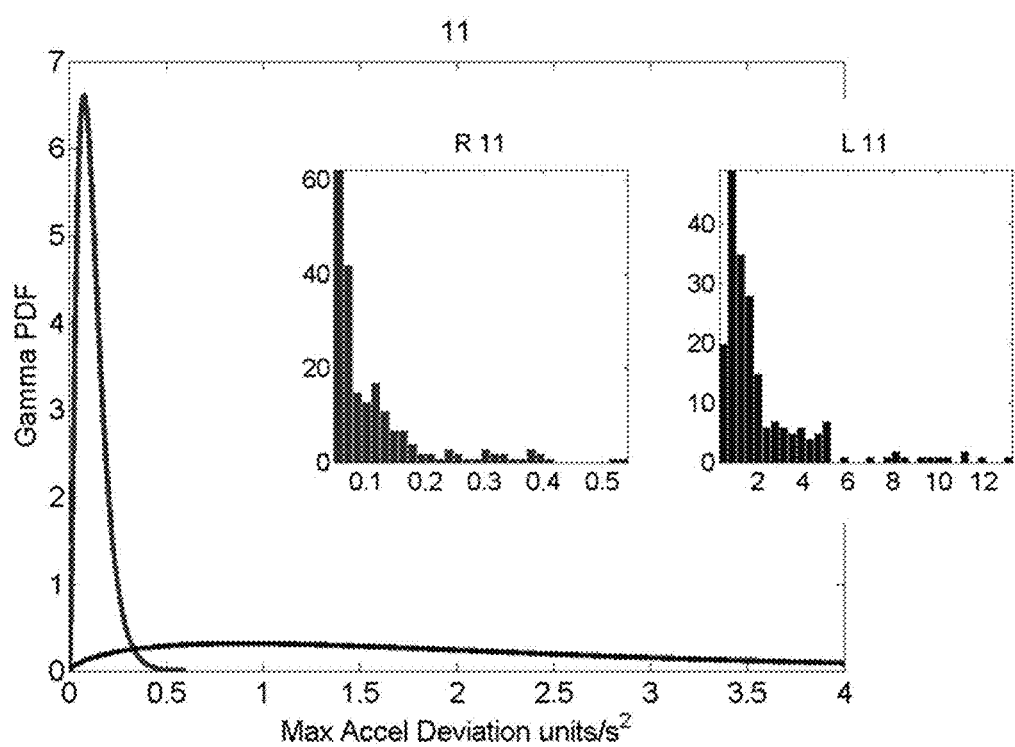
Figure 10E:
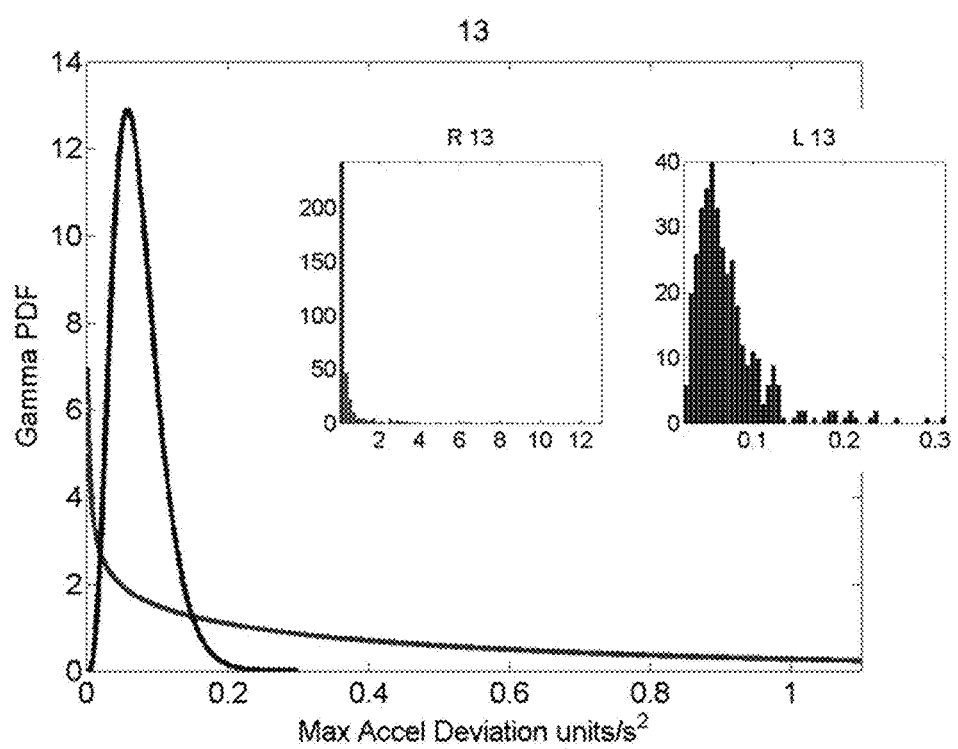
Figure 10F:
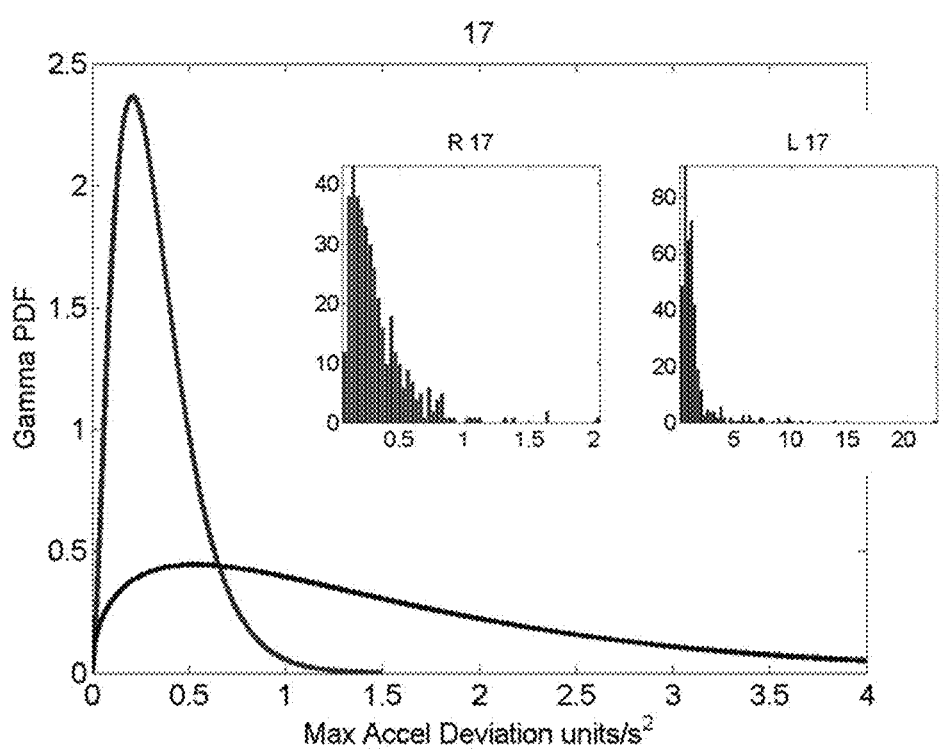
Figure 10G:
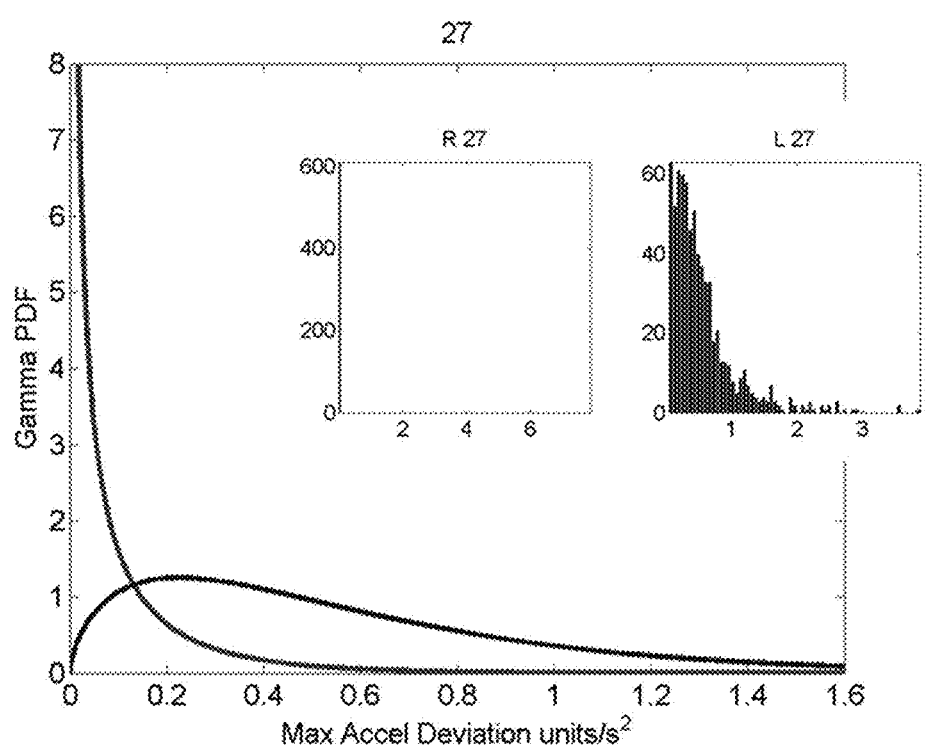
Figure 10H:
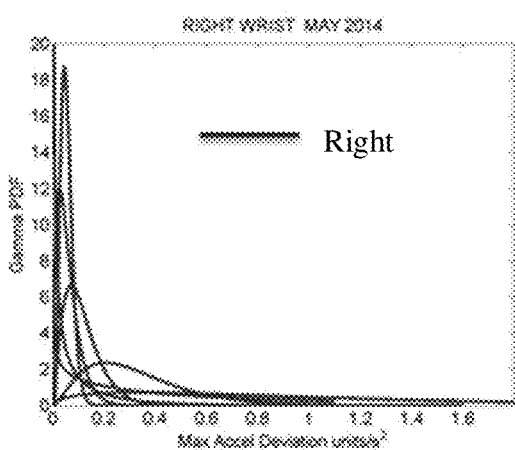
Figure 10I:
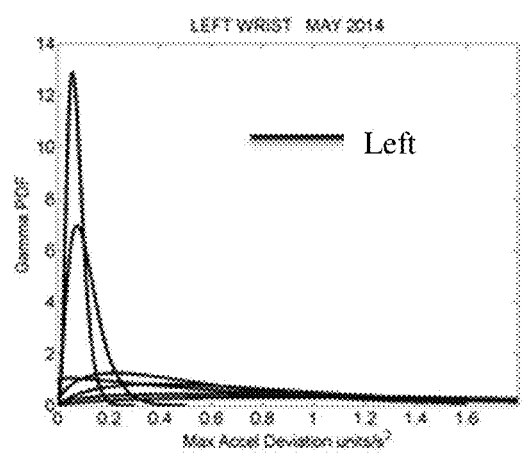

FIG. 10A-10I show gamma pdf estimation from each session and temperature range having low noise-to-signal information in the month of May 2014. FIGS. 10A-10G: The estimation of the Gamma pdf's across 7 sessions was done from the empirical data registered by the sensors at the wrist. Insets are the frequency histograms of the maximal deviations from the mean acceleration and graphs are the pdf curves within the ranges of the experimental data and for the estimated shape and scale parameters of the continuous Gamma family of probability distributions. FIGS. 10H-10I: Summary of the right and left wrist Gamma pdf patterns obtained within the temperature values determined using the methods of FIG. 2 according to the minimal noise-to-signal values within the temperature ranges from the sensor's readings. Each number on the graph represents the day of the recording in the month of May.

Figure 11A:
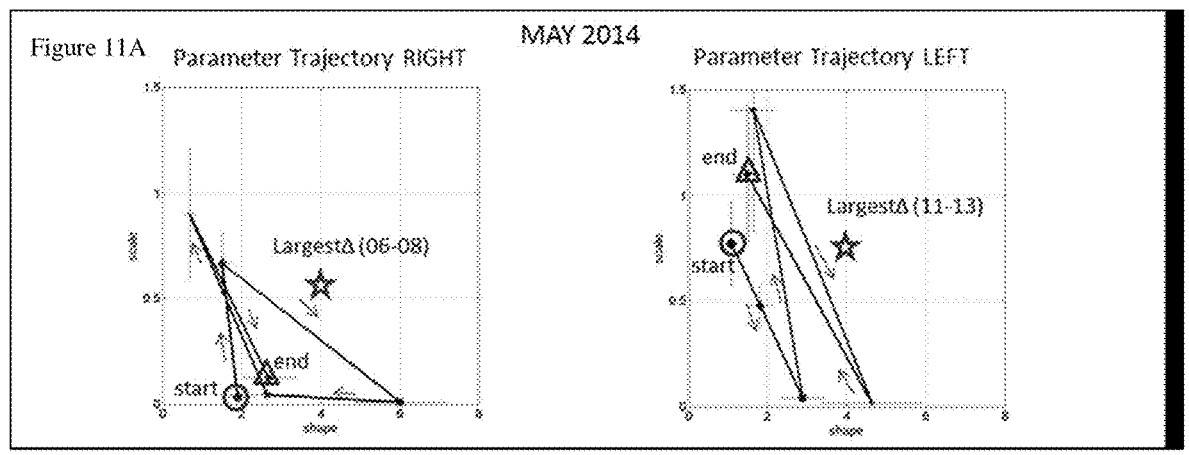
Figure 11B:
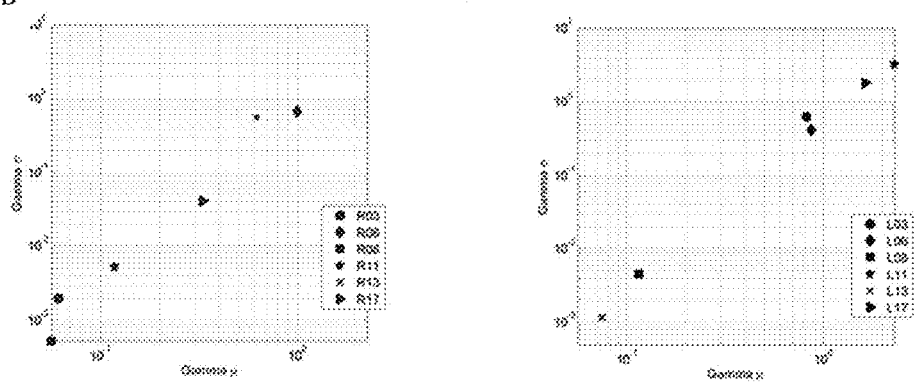

FIGS. 11A-11B show the longitudinal trends in changes of stochastic signatures of acceleration variability (May). FIG. 11A: Trajectory across recording sessions of the estimated scale and shape parameters for maximal acceleration using the continuous Gamma family of probability distributions. Each point is plotted on the Gamma parameter plane with 95% confidence intervals. Arrows indicate the flow of the trajectory in the order in which the data were acquired from the start circle (May 6) to the end triangle (May 17th). The star is the point of maximal change in shape (towards symmetric Gaussian-like range of the Gamma plane) and drop in scale value (decrease in the noise-to-signal ratio). FIG. 11B: Estimated mean and variance parameters of the Gamma probability distribution for each session (see legend with dates for right R and left L cases) with symbols corresponding as well to parameters in FIG. 11A. The log-log plot is used for better visualization. Notice that the values of the variance and the mean corresponding to the maximal shifts in stochastic parameters marked by stars in FIG. 11A are at the extreme locations of the Gamma-statistics plane.

Figure 12A:
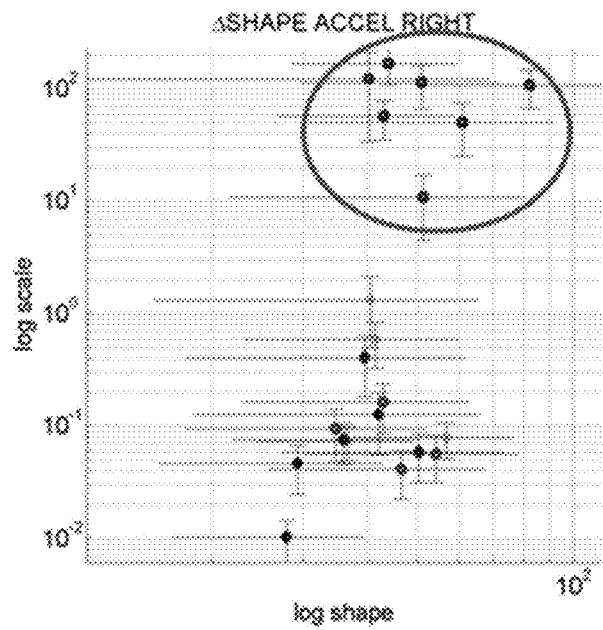
Figure 12B:
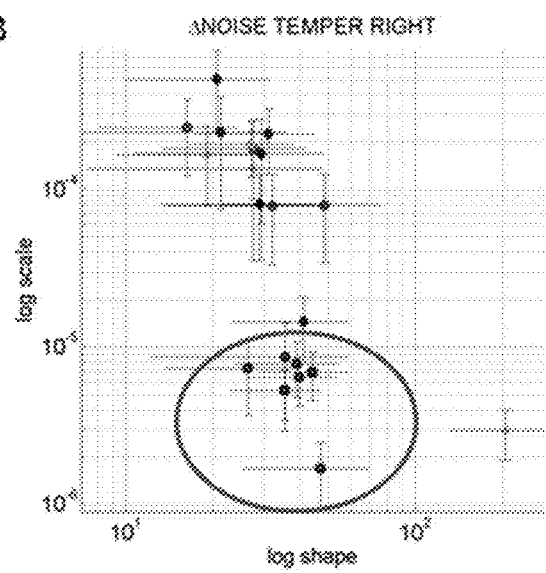
Figure 12C:
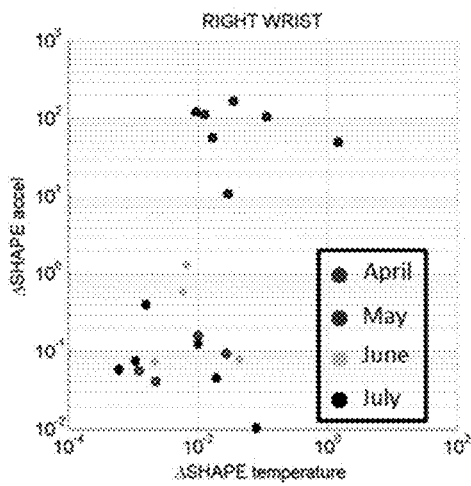
Figure 12D:
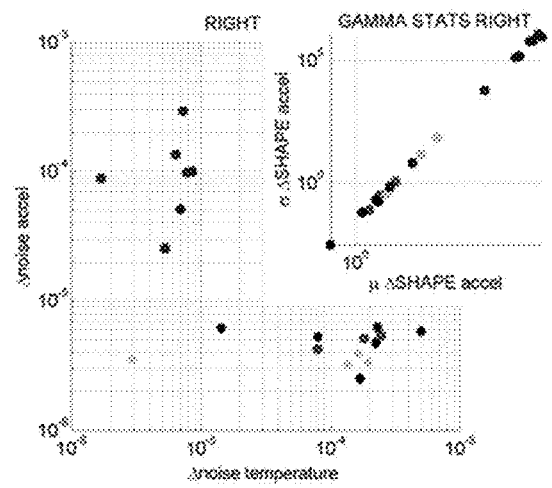

FIGS. 12A-12D show the longitudinal analyses of the rates of change of the noise-to-signal levels of the acceleration as a function of the temperature readings. FIG. 12A: The changes in the shape of the distributions of the noise-to-signal values of the motion (maximal deviations from the mean acceleration) followed a Gamma distribution. They are plotted on the Gamma parameter plane. Notice that the stochastic signatures corresponding to the sessions recorded in May stand out from those in the other months. FIG. 12B: Similar analyses in the rate of change of the noise-to-signal of the temperature of the right wrist single out the month of May as a separate cluster from all other readings. Lower changes in the noise level and overall higher values of the parameter indicating the shape of the distribution were registered in May, as compared to the other months. FIG. 12C: The rates of change in the shape of the distributions characterizing the noise-to-signal levels of the acceleration as a function of the temperature were systematic during the month of May and clustered apart from the readings of the other months. FIG. 12D: The stochastic signatures of the rates of change in the noise-to-signal levels of the acceleration expressed as a function of those of the temperature also clustered apart in May from the rest of the recordings in other months. Inset shows the estimated Gamma statistics for the rate of change in the shape of the Gamma distribution corresponding to the acceleration parameters with systematic increases in the variability of the maximal deviation from the average acceleration with increases in the mean value of this parameter.

Figure 13A:
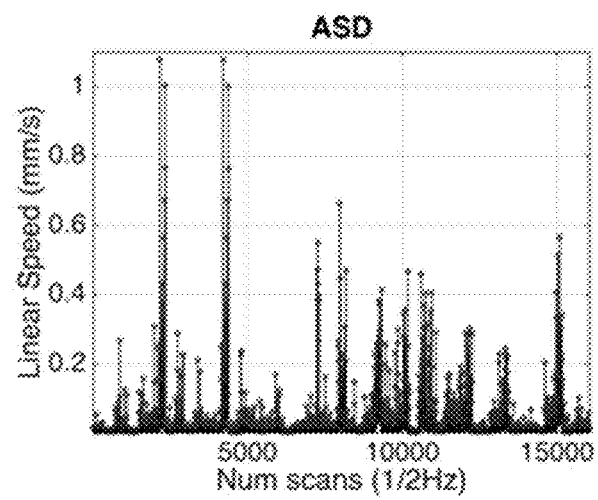
Figure 13B:
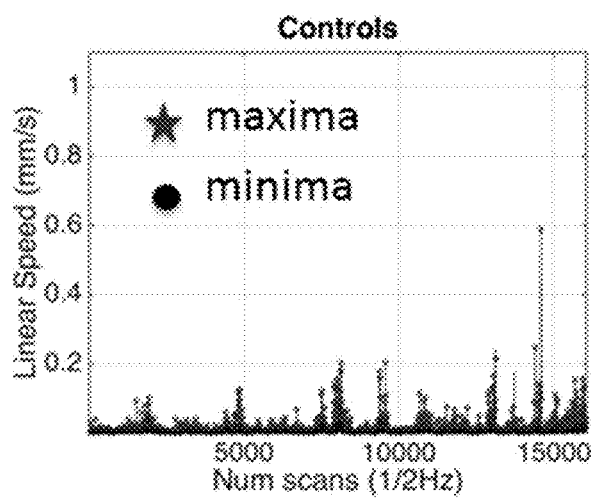
Figure 13C:
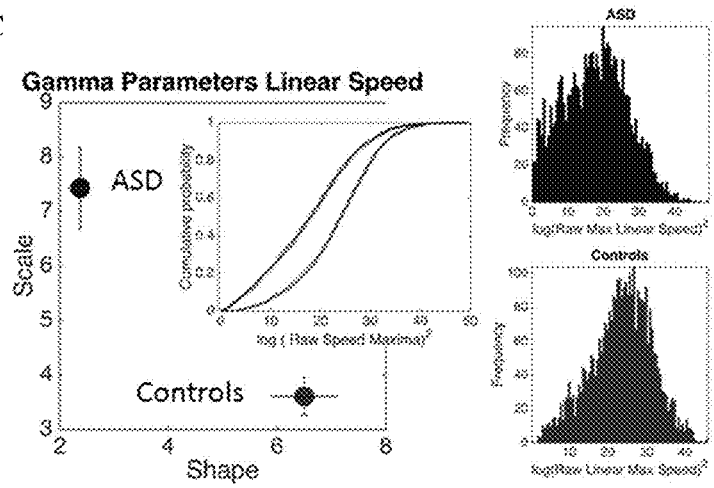
Figure 13D:
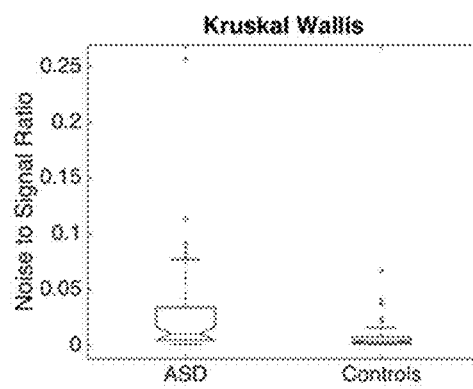

FIGS. 13A and 13B show the magnitude of the rate of change of linear head displacement over time (speed scalar profile) for the 110 participants pooling the motion data over the dataset from one site (UM_1, 300 scans per participant) taken every 2 seconds. The landmarks of interest in this time series are the speed maxima and minima also highlighted in the plots. FIGS. 13A and 13B show time series for ASD (N=55) and control (N=55) participants, respectively. FIG. 13C provides frequency histograms of the squared log of the raw maxima speeds are presented for each group along with the corresponding empirical cumulative probability distribution plots (with tight confidence intervals). The corresponding estimated parameters of the continuous Gamma family of probability distributions, the estimated shape and the estimated scale from the empirical data, are plotted for each group on the Gamma plane with 95%-confidence intervals. Notice the unambiguous differences in stochastic signatures between the two groups. FIG. 13D provides the scale parameter (the noise to signal ratio) estimated from the raw peaks is significantly different according to the Kruskal-Wallis (non-parametric one-way ANOVA) test at the 0.01 alpha level.

Figure 14A:
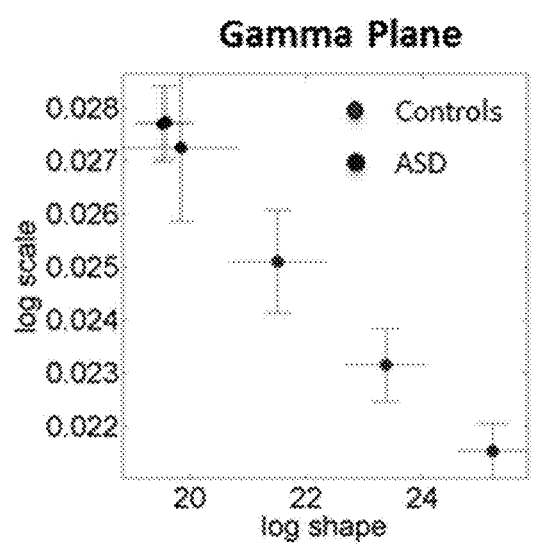
Figure 14B:
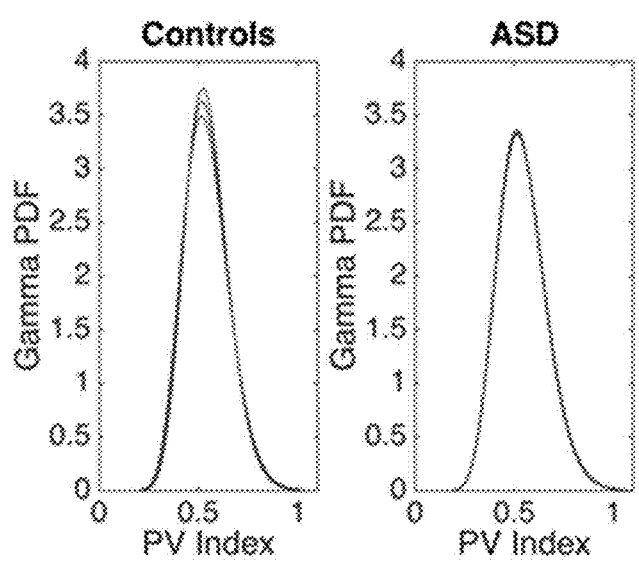
Figure 14C:
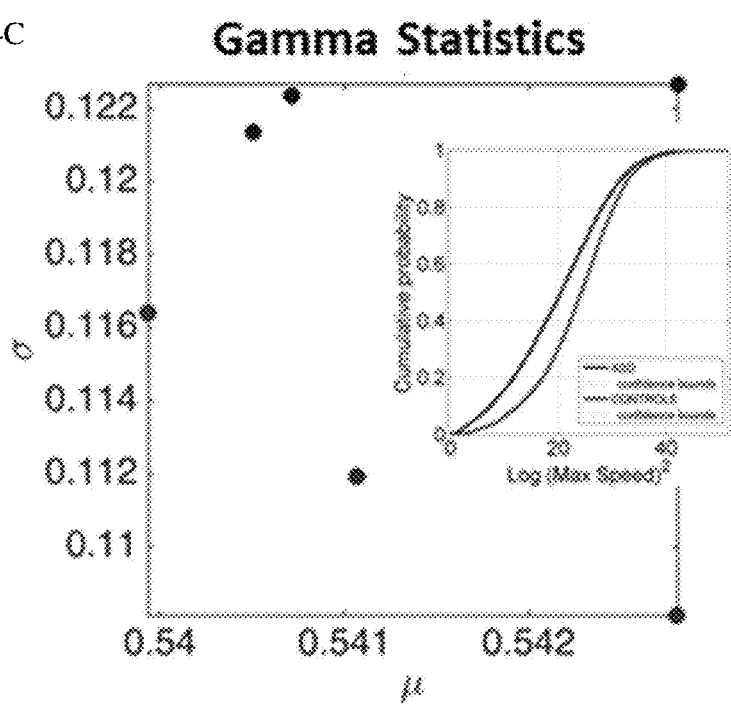
Figure 14D:
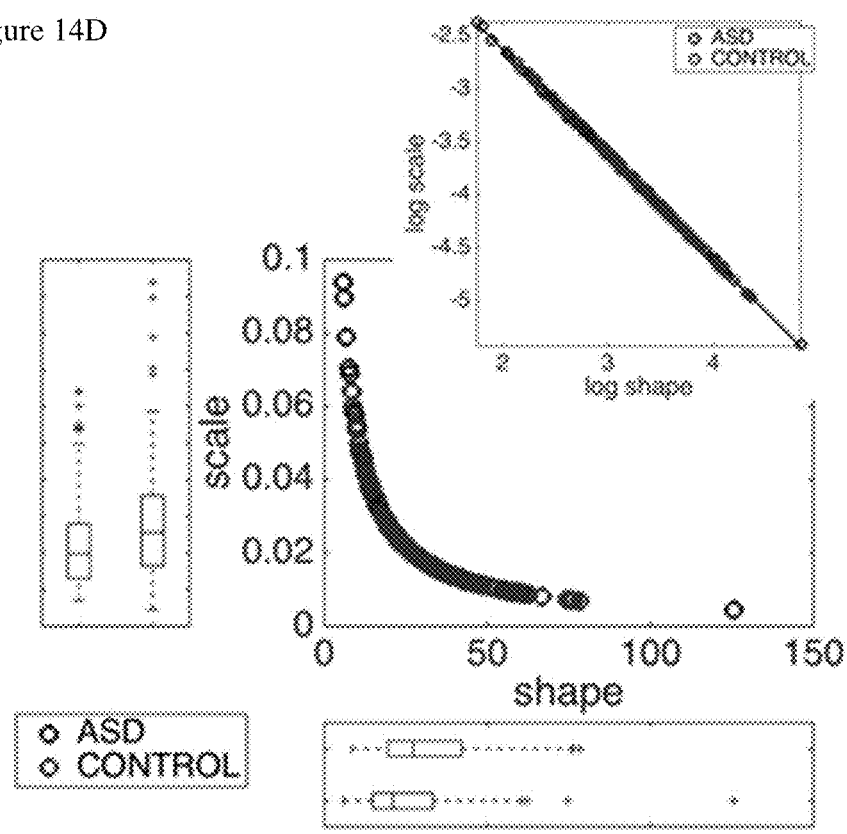
Figure 14E:
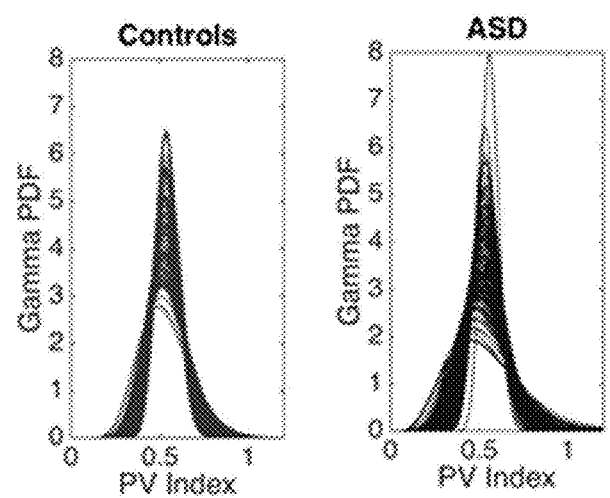
Figure 14F:
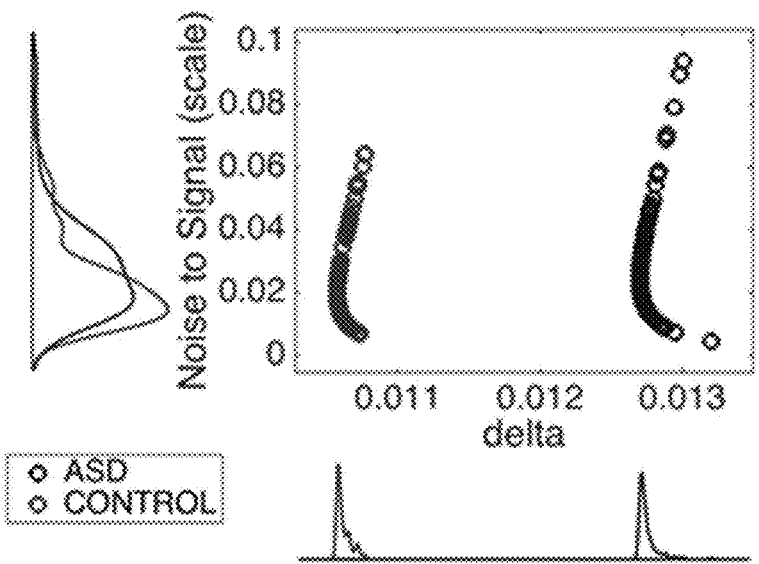

FIG. 14A provides the empirically estimated shape and scale Gamma parameters of the normalized PV index plotted on the Gamma plane with 95% confidence intervals for each study aligns ASD and controls on different locations of the plane. FIG. 14B provides estimated Gamma probability density functions (PDF) per group and study-site. FIG. 14C provides the estimated Gamma statistics (mean and variance) plotted on the statistics plane per group and study-site. Inset shows the differences between the empirical cumulative distribution functions (eCDF). FIG. 14D provides the ensemble data unfolded for all 246 participants (126ASD, 120TD). Log-log plot of the shape, scale plane values reveal a power relation in the data. Despite overlapping regions, the box plots reveal significant differences in both estimated Gamma parameters between the two groups. FIG. 14E provides the estimated PDFs across all participants in the two diagnostic groups from all 3 studies. FIG. 14F provides scatter plots and histograms of the noise to signal ratio as a function of the fitting residual (denoted delta) from the power fit in FIG. 14D separate the two group types and hints at an ASD subset with much higher noise levels than controls.

Figure 15A:
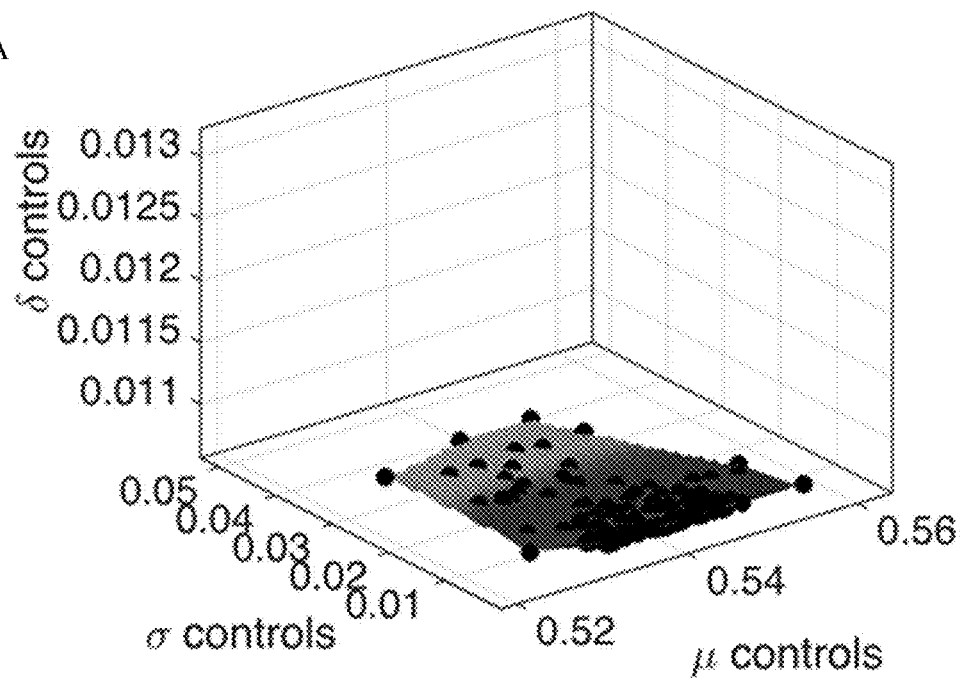
Figure 15B:
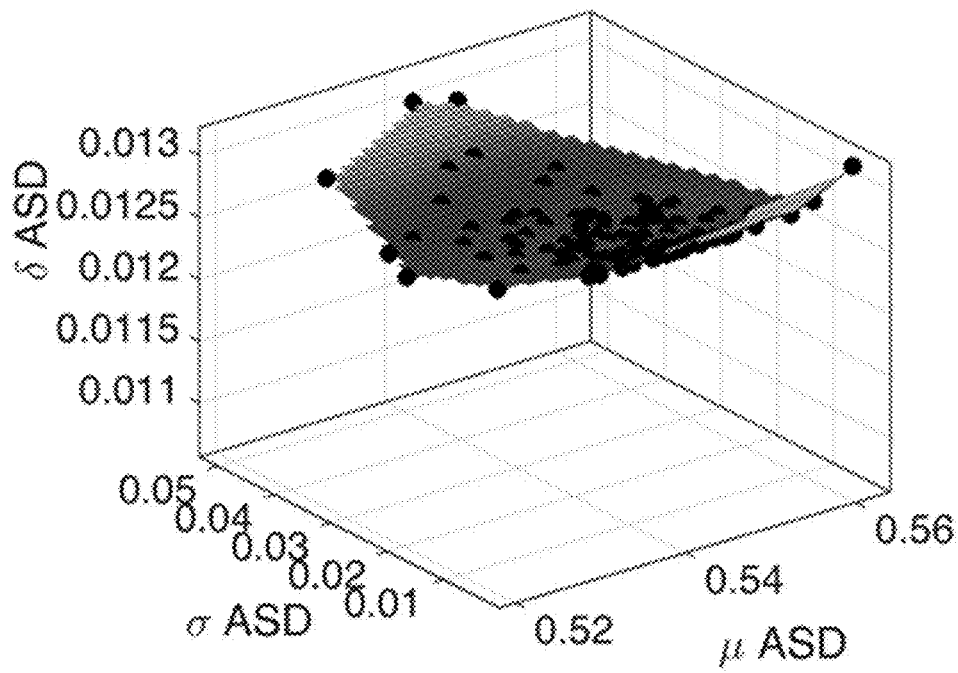
Figure 15C:
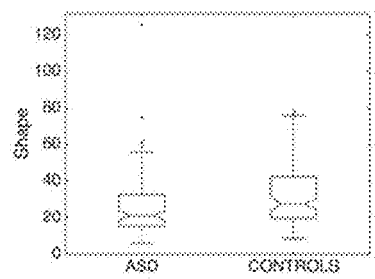
Figure 15D:
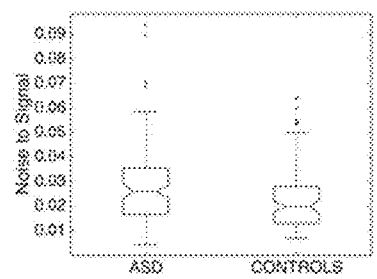
Figure 15E:
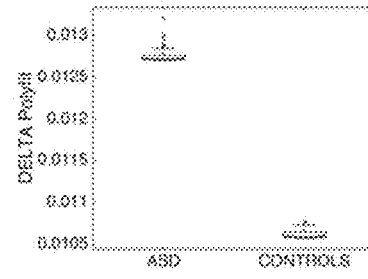

FIGS. 15A and 15B provides three dimensional surfaces fitting the parameter points of the controls and of the ASD, respectively. FIGS. 15C-15E show Kruskall-Wallis (one way non-parametric ANOVA) test yields statistically significant differences at the 0.01 level for comparison differences between the two groups along the Gamma mean, standard deviation and delta residual from the polynomial fit to the scatters in FIGS. 15A-15B (ranksum Wilcoxon test, $P<10^{-4}$ in FIGS. 15C, 15D and $p<10^{-41}$ in FIG. 15E).

Figure 16A:
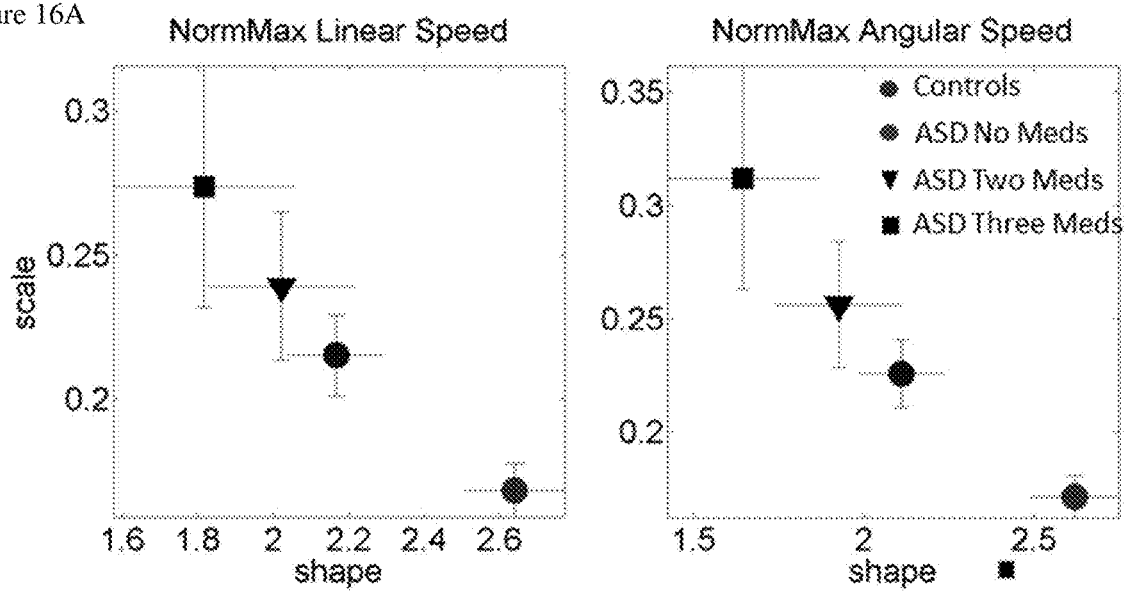
Figure 16B:
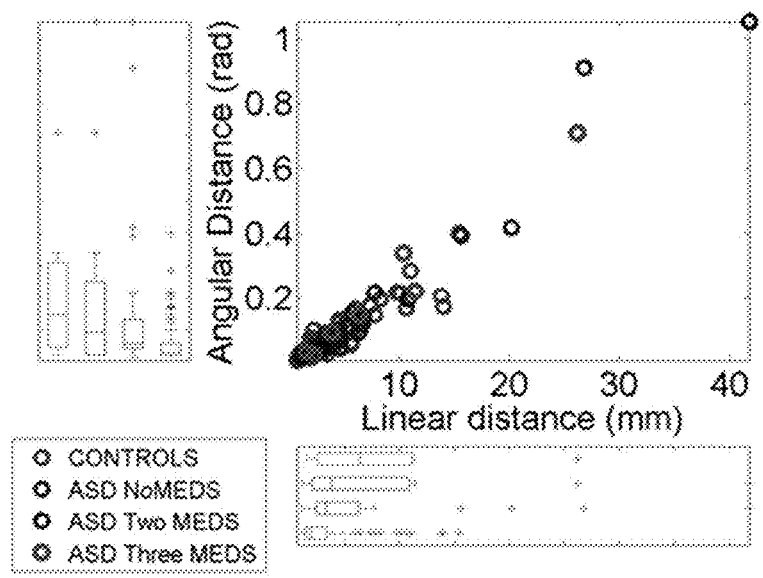

FIG. 16A provides the shape and scale parameterization of the normalized linear peak velocity and normalized angular velocity indexed with 95% confidence intervals show systematic shifts with no medications, one medication and two medications in ASD vs. controls. FIG. 16B provides the quantification of the cumulative linear displacements and angular rotations across the entire session (300 frames) for all 4 groups of UM_1 and UM_2. Systematic increase of the head excursion (cumulative linear and angular distances covered in a session) as a function of medication quantity.

Figure 17:
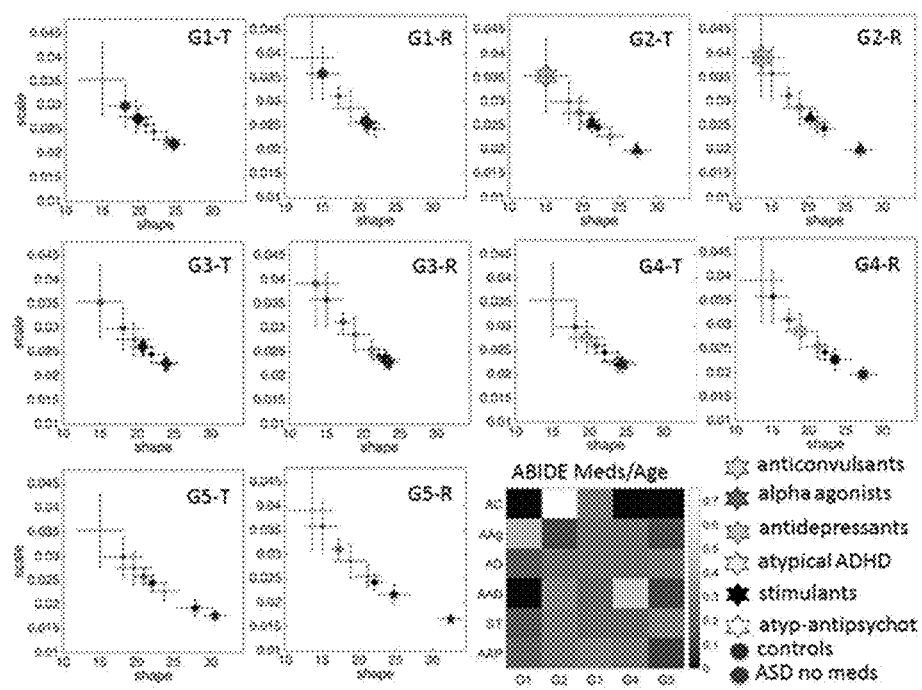

FIG. 17 provides the speed-dependent stochastic signatures of head micro-motions variability for medication classes when taken as part of a combination-treatment. Each age group number (e.g. G1-T and G1-R) plots the translational (T) and rotational (R) speed-dependent signatures across medication type with 95% confidence intervals. Groups by age are G1 (6-10), G2 (11-12), G3 (13-14), G3 (15-16), G5 (above 17) years old. The empirically estimated Gamma parameters for the medicated ASD are obtained from the pooled data whereas each point is cast against the members of an age group. The size of the marker represents the percentage of that medication type within the group based on the ABIDE reports. The matrix contains these percentages as well for each age group (columns) and medication class (rows). Each age group has a most prevalent medication class (G1 alpha agonist, G2 anticonvulsant, G3 anticonvulsant, G4 atypical ADHD and G5 stimulant). No marker means that the medication is not present in the group (darkest entry in the matrix if there is one). Independently of the proportion, from highest to lowest scale (noise-to-signal ratio) and from lowest to highest shape values the order found is listed in the legend. The controls have the lowest noise-to-signal ratio and the highest shape (most symmetric) value in all cases. All other locations representing medicated and non-medicated ASD can be referenced to the age-control group.

Figure 18:
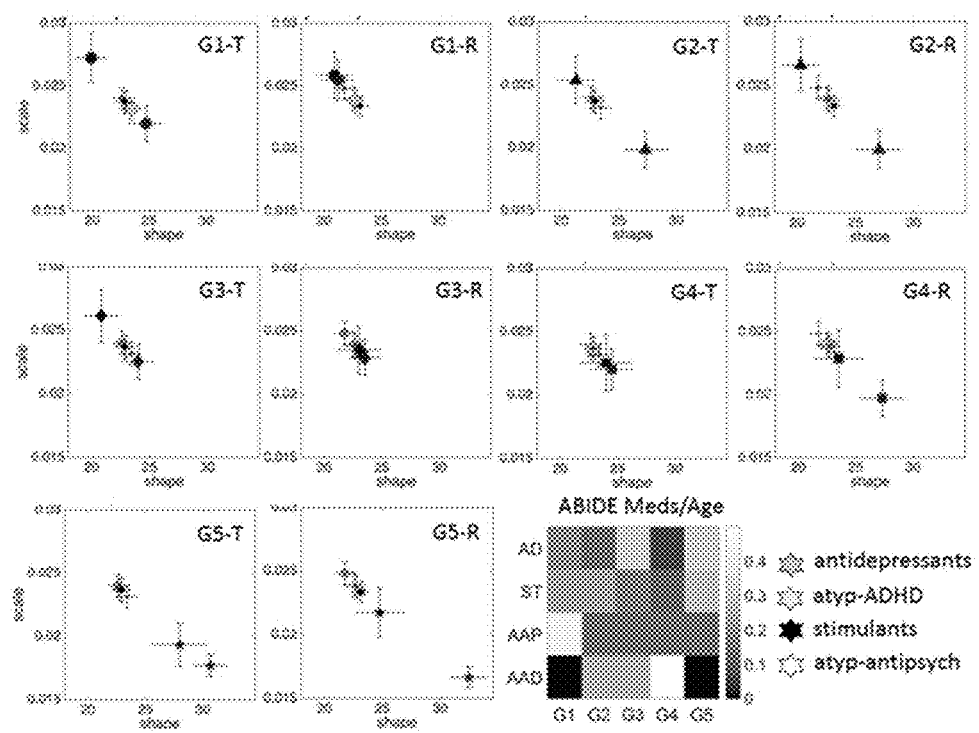

FIG. 18 provides speed-dependent stochastic signatures of head micro-motions variability for medication classes when taken in isolation. The highest percentages across age groups are: G1 atypical antipsychotic, G2 atypical ADHD, G3 antidepressant, G4 atypical ADHD, G5 antidepressant. Notice that when taken in isolation, the same medication class has a different effect for each age group than when taken as part of a medication combination.

Figure 19:
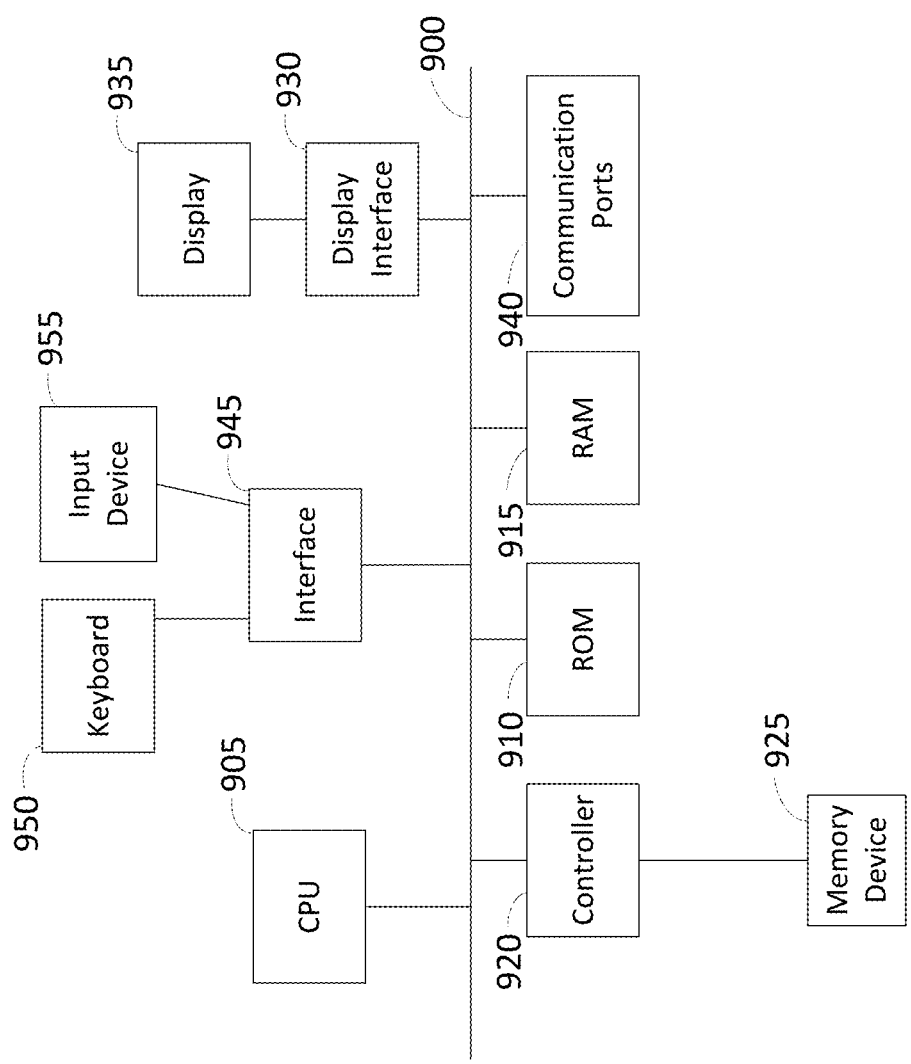

FIG. 19 is a block diagram of elements of a computing device on which the various systems and methods in this document could be implemented.

DETAILED DESCRIPTION OF THE INVENTION

With the advent of wearable sensing technology, motion tracking can be used, optionally, in combination with other physiologically relevant signals (temperature, electrodermal activity, heart beat variability, etc.), to help medical personnel and care givers assess the patient's mental and physical states daily, both during the hospitalization period and after discharge (e.g., when the patient goes into rehabilitation). Here, new personalized statistical methods are provided that allow for the tracking of the progression of patients with a disease or disorder (e.g., neurological disorder or post TBI (e.g., severe TBI)). Particularly, the methods are illustrated with data from a pregnant patient who underwent a severe TBI, slipped into a coma and had her baby successfully delivered by C-section. The methods are also illustrated with subjects having an autism spectrum disorder.

Figure 1:
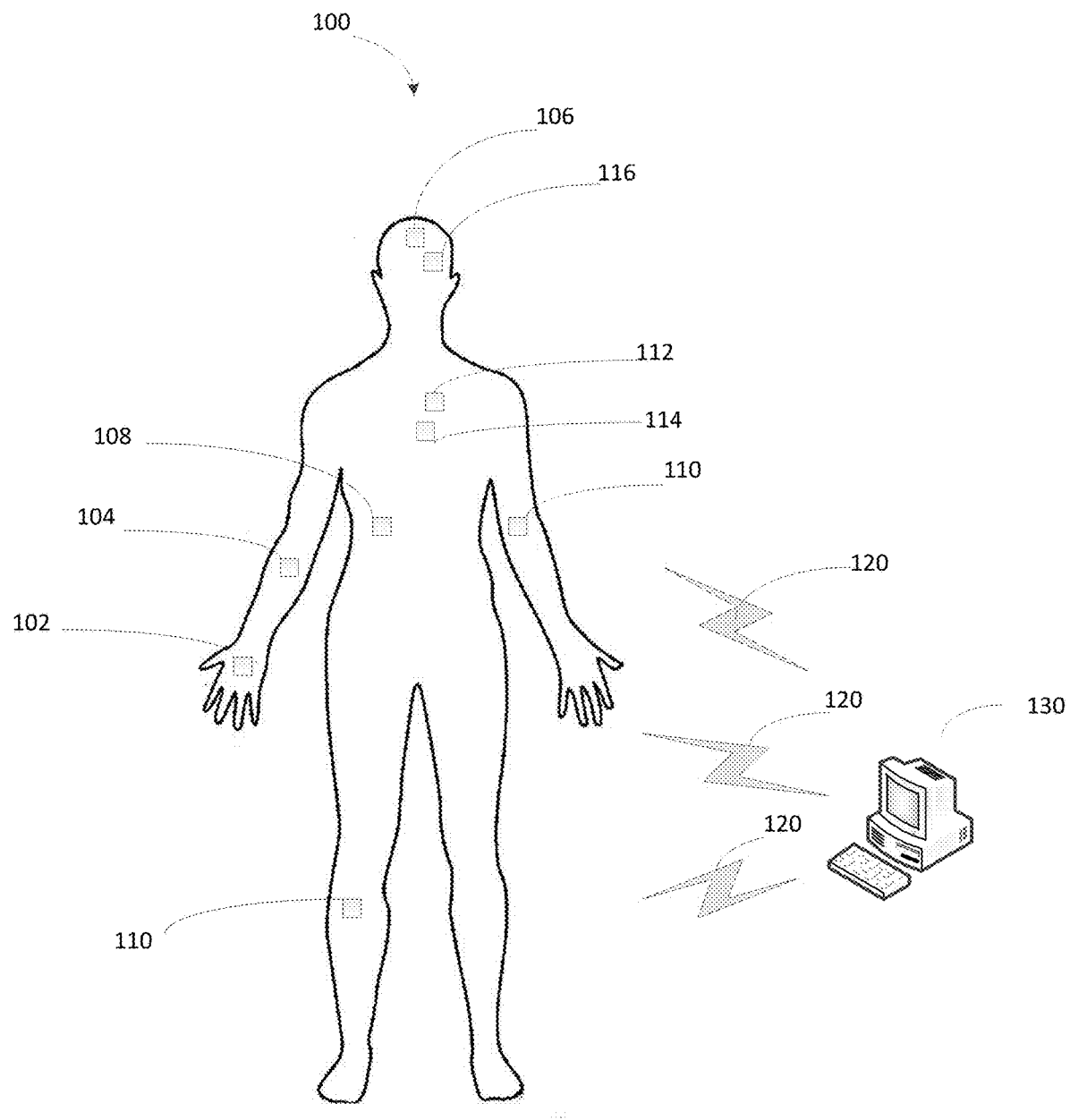
FIG. 1 shows an example of a system for identifying physiologically relevant biorhythm of a subject.

In FIG. 1, a system 100 for identifying physiologically relevant biorhythm of a subject includes at least a motion sensor 102, 104, 106, 108, 110 attachable to a body part of the subject and biometric sensors 112, 114, 116 also attachable to a body part of the subject. The system also includes one or more communication links 120 (wired or wirelessly) for retrieving sensor data and also one or more computing device 130 for analyzing the sensor data.

The motion sensor 102, 104, 106, 108, 110 are configured to measure movement of the subject and produce a series of movement data representing the movement of the subject over a period of time. The motion sensor may be an inertial measure unit (IMU) and attachable to a body part of the subject to monitor the motion of any part of the body. For example, the motion sensor 102, 104, 106, 108, 110 may be attached to the hands, arms, head, trunk and limbs (including foot and ankle) etc., respectively, to monitor the motion of the respective body part of the subject. In a particular example, the motion pattern of the subject's arm or hand, particularly the dominant arm or hand, is measured. In a particular example, the motion pattern of the subject's head is measured. In a particular example, the difference in size of the body parts (e.g., limb size) of subjects and controls is accounted for (e.g., normalized).

With the motion sensors, the system produce series of movement data over a period of time. Any parameter of the motion of the subject may be measured (e.g., by a wearable motion sensor). Parameters that can be measured include, without limitation: velocity, acceleration, speed profile, max speed, max acceleration, minimum speed, minimum acceleration, time to reach maximum speed, time to reach maximum acceleration, max retraction speed, time to reach max retraction speed, inter-peak intervals, three-dimensional path, accuracy of target touching, overall amount of time for motion, body part rotation or positioning, translational movement, rotational movement, and joint angle. In a particular embodiment, acceleration of the movement is measured.

The biometric sensors 112-114 are configured to measure simultaneously (e.g., in tandem with the motion sensor) biometrics of the subject and produce a series of biometric values of the subject over the period of time. The biometric sensor may be one of the following: a thermometer, an electroencephalogram (EEG), an electromyography (EMG), a stethoscope or a heart rate monitor. With the biometric sensors, the system may simultaneously measure (i.e. in tandem with the motion sensor) biometrics of the subject and produce series of biometric values over the period of time. Any biometric of the subject may be measured. For example, the subject's temperature (e.g., skin temperature), heart rate (e.g., beats per minute or inter beat time interval), electrodermal activity, electrical activity of brain (e.g., brain waves, for example, as measured by electroencephalogram (EEG)), electrical activity of muscles (e.g., as measured by electromyography (EMG)), and/or breathing pattern are measured. In a particular embodiment, the subject's temperature is measured.

The system of FIG. 1 also include non-transitory computer readable medium containing programming instructions that, when executed, will cause the processing device to produce series of movement data and biometric values over a period of time analyze the series of data to identify physiological relevant biorhythms of the subject, as will be described in detail with reference to FIG. 2.

Figure 2:
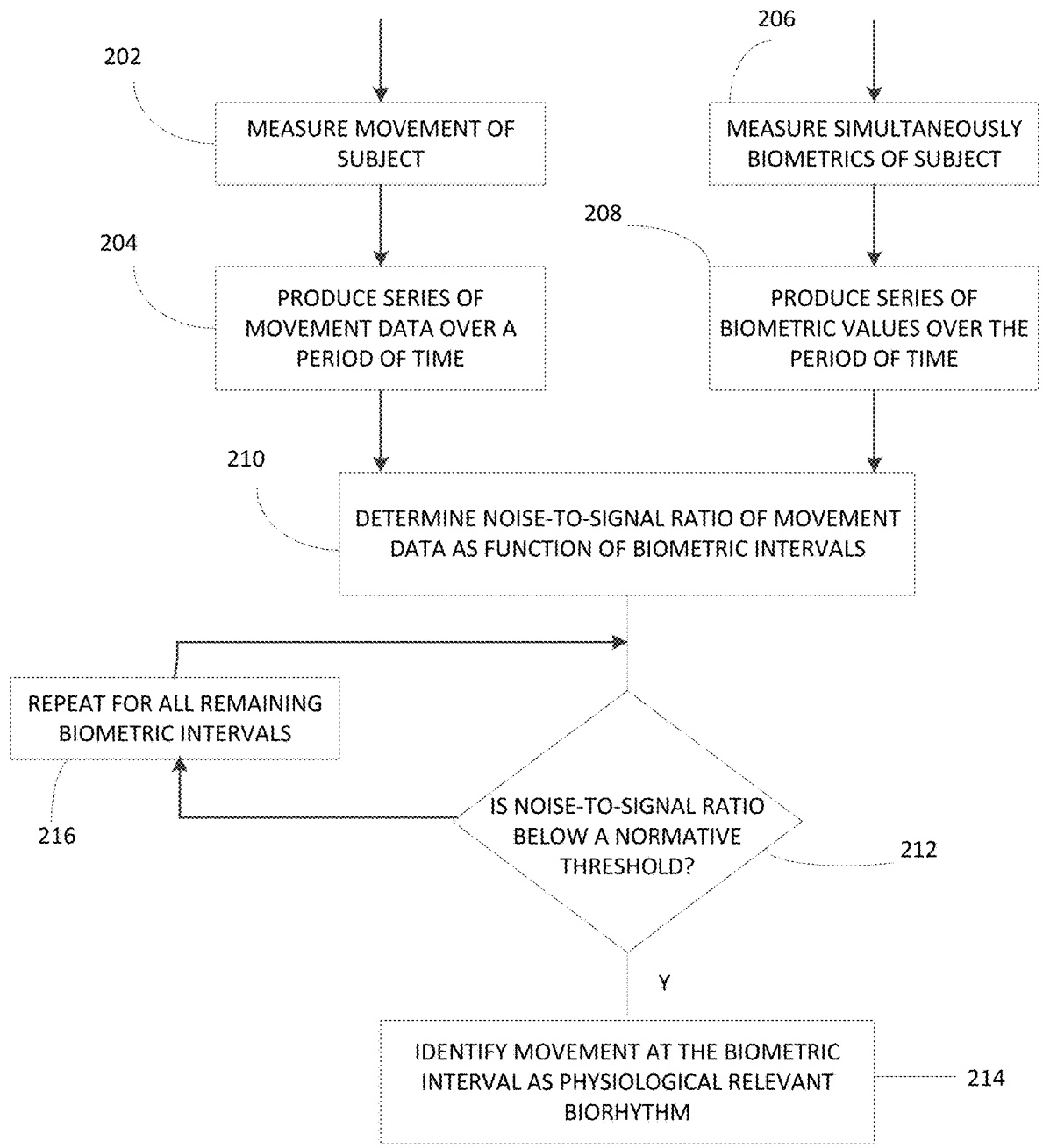
FIG. 2 shows an example of a process of identifying physiologically relevant biorhythm of a subject.

In FIG. 2, in accordance with the instant invention, a methods of detecting, measuring, and/or monitoring motion (e.g., physiologically relevant biorhythm or spontaneous motion (e.g., not deliberate or intended movement)) of a subject are provided. In a particular example, a method includes measuring movement of a subject 202 using one or more motion sensors attached to one or more body parts of the subject, and producing series of movement data over a period of time 204. The method may also include measuring simultaneously (e.g. in tandem with the motion sensor) biometrics of the subject 206, and producing series of biometric values over the period of time 208. In a particular example, the movement is a micro-movement (e.g., a movement not recognizable (or not easily recognizable) by the naked eye; e.g., movements in the millisecond and/millimeter range). In a particular embodiment, the subject is actively attempting not to move and/or attempting to remain still.

The method may also include determining the noise-to-signal ratio for the movement data as a function of the biometric intervals 210. This is further illustrated with examples shown in FIGS. 5 and 6A). For example, in FIG. 5, the noise-to-signal ratio for the acceleration data is represented by a maximal deviation from mean acceleration as a function of temperature intervals, e.g. 25° C., 27° C., 29° C., 31° C., 33° C., and 35° C. The method further includes determining whether a noise-to-signal value for a portion of the series at a particular biometric interval is lower than a normative threshold 212. If the noise-to-signal ratio is below a normative threshold, the system may identifying the portion of the series of movement data as corresponding to a physiologically relevant biorhythm 214. The system may repeat checking remaining portions of the series of movement data at other biometric intervals 216. In a particular example, the system may determine that movements with the lowest noise noise-to-signal ratio (e.g., the lowest 50%, lowest 25%, the lowest 10%, the lowest 5% or the lowest 1%) are the physiologically relevant biorhythms.

Figure 3:
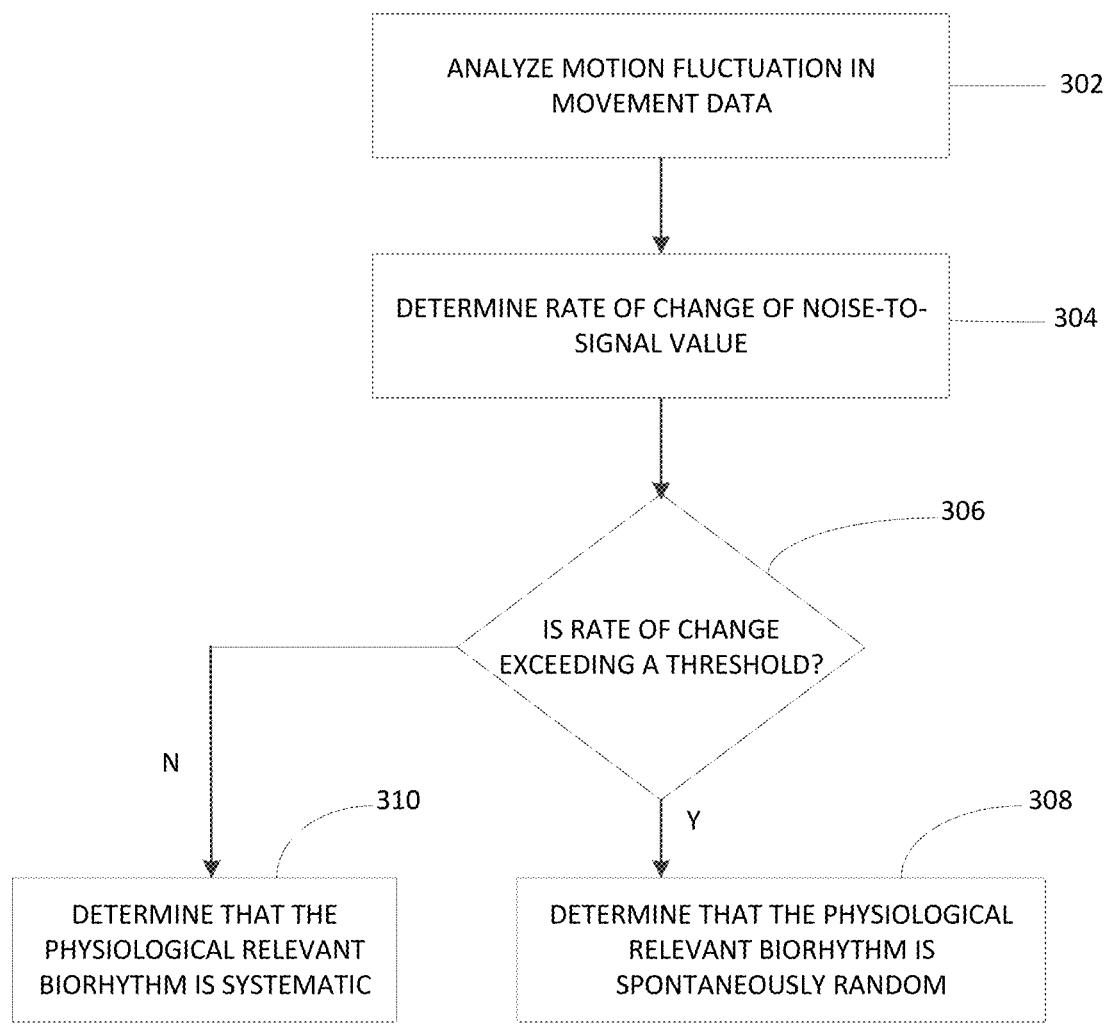
FIG. 3 shows an example of a process of determining whether a physiological relevant biorhythm is spontaneously random.

In FIG. 3, the system may also include analyzing motion fluctuation in the movement data 302, and determine the rate of change of noise-to-signal value 304. For example, for the portion of the series of movement data that correspond to the physiologically relevant biorhythm, the system may determine a rate of change of the noise-to-signal value for each biometric interval. The system may further determine whether the rate of change exceeds a threshold 306. Upon determining that the rate of change at the biometric interval exceeds the threshold, the system may determine that the physiological relevant biorhythm at the biometric interval is spontaneously random 308. Otherwise, the physiological relevant biorhythm at the biometric interval is systematic 310.

In an example, the series of movement data include an acceleration and the biometric values include a temperature. The method of determining the rate of change of the noise-to-signal value above may includes estimating parameters of a continuous Gamma distribution family based on the portion of the series of movement data at each biometric interval; determining a shape parameter of the continuous Gamma distribution; and determining a rate of change of the shape parameter of the continuous Gamma distribution. This will be further illustrated in Examples 1 and 2 below.

In some scenarios, the system may also be configured to measure head movement of a subject by using a functional magnetic resonance imaging (fMRI) device. For example, the fMRI device may be configured to collect a sequence of images of the head of the subject over a period of time, and the system may be configured to use a motion estimate method to estimate the movement of the head of the subject over the period of time. The methods for determining head motion will be further explained with reference to Example 2.

In some scenarios, the system may also display a three-dimensional matrix on a display. For example, in FIG. 4E, the three-dimensional matrix include a plurality of cells in a two-dimensional plane, in which the y-axis (first dimension) is the period of time. The resolution of the y-axis may be the same as the sampling resolution of the motion sensor. For example, a minute is a basic unit of time interval, the sensors are sampled at 128 Hz (128 samples per second) so in 60 sec there will be 128×60 samples which are sufficient to make a statistical estimation. As shown in FIG. 5, with 128 Hz sample resolution of motion sensor and on minute time interval, there will be plenty of peaks and valleys to estimate fluctuations in amplitude, peak coincidence and phase shifts between two signals, etc.

Returning to FIG. 4E, the x-axis (second dimension) is the series of biometric values, such as temperature intervals. The x-axis (second dimension) may also be another biometric value, such as a heart rate. Each of the plurality of cells is coded by a color or a gray scale that represents a maximal deviation from a mean acceleration of the series of movement data corresponding to an instant of time in the period of time and a biometric value in the series of biometric values.

The three-dimensional display shown above is a new data type that allows a user to understand and characterize the probabilities of one biorhythm given knowledge of the probability of another biorhythm. As shown in FIG. 4E, for example, the three-dimensional display combines two physiological signals ((1) motion and (2) temperature) harnessed simultaneously using the same sensor at the same sampling resolution. The example in FIG. 4E separates all the motion (parameter (1)) occurring within a given 2° C. interval, so if the range of temp (parameter (2)) spans from 26 to 34, for each 2° C. interval the motion can be isolated. In this way, the system may be able to examine a temperature dependent motion and specifically what happens to the body in motion at high temperature and what happens to it at low temperature.

The three-dimensional display may also have variations. For example, with heart rate, the display may isolate the inter-beat-interval (IBI) times in milliseconds and the system may examine all motion for different intervals (e.g. every 100 ms) to produce a heat-rate dependent motion profile. The first and second dimensions may also vary and there may not be a fixed order. For example, the three-dimensional display may be inverted to allow user to see motion-dependent temperature regimes or motion-dependent heart-rate regimes.

In some scenarios, the subject may be conscious or unconscious. In a particular embodiment, the subject is unconscious. In a particular embodiment, the subject has suffered a traumatic brain injury. As used herein, "traumatic brain injury" or "TBI" refers to an acquired brain injury or a head injury, when a trauma causes damage to the brain. Trauma includes, e.g., post-head trauma, impact trauma, and other traumas to the head such as, for example, traumas caused by an external, physical force, accidents and/or sports injuries, military injuries, concussive injuries, penetrating head wounds, brain tumors, stroke, heart attack, meningitis, viral encephalitis, and other conditions that deprive the brain of oxygen. The damage can be focal (confined to one area of the brain) or diffuse (involving more than one area of the brain). The TBI can be chronic or acute. The traumatic brain injury can result from a closed head injury (a brain injury when the head suddenly and violently hits an object but the object does not break through the skull). Clinically, traumatic brain injury can be rated as mild, moderate or severe based on TBI variables that include duration of loss of consciousness (LOC), Glasgow Coma Score (GCS; e.g., mild 13-15; moderate=9-12; severe=≤8) and post traumatic stress amnesia (see, e.g., Levin et al. (1979) J. Nervous Mental Dis., 167:675-84; Holm et al. (2005) J. Rehabil. Med., 37:137-41). In a particular embodiment, the TBI is severe.

In accordance with another aspect of the instant invention, methods of monitoring and/or diagnosing a disease or disorder in a subject. In a particular embodiment, the method comprises monitoring the motion (e.g., physiologically relevant motion or spontaneous movement) of the subject by the methods described herein over time (e.g., at least two time points). In a particular embodiment, the movement is a micromovement. In a particular embodiment, the subject is actively attempting not to move and/or attempting to remain still. In a particular embodiment, the subject is unconscious or in a coma. The subject may have suffered a TBI, particularly a severe TBI. The subject may have a neurological disorder. In a particular embodiment, the subject has an autism spectrum disorder. In a particular embodiment, the methods of the instant invention diagnose and/or monitor a subtype of autism spectrum disorder. In a particular embodiment, the gender and/or age of the subject and the control standards are the same.

The instant invention also encompasses methods for determining the ability of a therapy to modulate a disease or disorder in a subject. In a particular embodiment, the method comprises administering the therapy to a subject and monitoring the motion (e.g., physiologically relevant motion or spontaneous movement) of the subject by the methods described herein (e.g., over time) to determine whether the administered therapy modulated (e.g., treated) the disease or disorder (e.g., by comparing to standards/controls or previously obtained standards of the subject). The modulation of the motion (e.g., physiologically relevant motion) of the subject after administration of the therapy (e.g., towards the physiologically relevant motion of a healthy or normal individual) indicates that the therapy modulates the disease or disorder. The direction of this modulation (away or towards typicality, or neutral meaning no change) is evaluated so the effectiveness of treatment can be objectively determined. In a particular embodiment, the method comprises monitoring the motion of the subject, administering the therapy to the subject, and re-monitoring the motion of the subject, wherein a change in the motion after therapy compared to before therapy indicates that the therapy modulates the disease or disorder. In a particular embodiment, if the motion after therapy more closely approximates the pattern of a healthy individual than before the therapy, the therapy is effective against the disorder or disease.

In a particular embodiment, the disease or disorder of the instant invention is a developmental/mental disability or neurological disorder. Neurological disorders include neurodevelopmental and neurodegenerative disorders. Specific examples of neurological disorders include, without limitation: Parkinson's disease, parkinsonian syndrome, Autism, Autism spectrum disorder, Huntington's disease, athetosis, dystonia, cerebellar and spinal atrophy, multiple system atrophy, striatonigral degeneration, olivopontocerebellar atrophy, Shy-Drager syndrome, corticobasal degeneration, progressive supranuclear palsy, basal ganglia calcification, parkinsonism-dementia syndrome, diffuse Lewy body disease, Alzheimer's disease, Pick's disease, Wilson's disease, multiple sclerosis, peripheral nerve disease, brain tumor, cerebral stroke, attention deficit hyperactivity disorder (ADHD), Down syndrome, William syndrome, schizophrenias, etc. In a particular embodiment, the developmental/mental disabilities or neurological disorders that the instant methods can be used with include, without limitation, attention deficit hyperactivity disorder (ADHD), Parkinson's Disease, stroke (e.g., stroke in the cortex, particularly the posterior parietal cortex; Torres et al. (2010) J. Neurophysiol., 104:2375-2388), Down syndrome, William syndrome, schizophrenics, concussive injuries (e.g., sports concussion), autism spectrum disorders, autism, Tourette's, neurodegenerative disorders, Fragile X syndrome, movement disorders, and the like. In a particular embodiment, the neurological disorder is Autism, Autism spectrum disorder, or Parkinson's disease.

Definitions

The following definitions are provided to facilitate an understanding of the present invention:

The singular forms "a," "an," and "the" include plural referents unless the context clearly dictates otherwise.

As used herein, "diagnose" refers to detecting and identifying a disease/disorder in a subject. The term may also encompass assessing or evaluating the disease/disorder status (severity, classification, progression, regression, stabilization, response to treatment, etc.) in a patient. The diagnosis may include a prognosis of the disease/disorder in the subject.

As used herein, the term "prognosis" refers to providing information regarding the impact of the presence of a disease/disorder on a subject's future health (e.g., expected morbidity or mortality). In other words, the term "prognosis" refers to providing a prediction of the probable course and outcome of a disease/disorder or the likelihood of recovery from the disease/disorder.

The term "treat" as used herein refers to any type of treatment that imparts a benefit to a patient afflicted with a disease, including improvement in the condition of the patient (e.g., in one or more symptoms), delay in the progression of the condition, etc.

As used herein, the phrase "millisecond range" may refer to a time frame that is less than one second, particularly less than about 0.5 second, y less than about 100 milliseconds, less than about 50 milliseconds, less than about 25 milliseconds, or less than about 5 or 10 milliseconds. In a particular embodiment, the motion of the subject (e.g., the speed) is observed over segments of time in the millisecond range (e.g., from about one to about 3 millisecond, from about 1 to about 5 milliseconds, from about 1 to about 10 milliseconds, from about 1 to about 25 milliseconds, about 1 to about 50 milliseconds, about 1 to about 100 milliseconds, or about 1 to about 500 milliseconds).

As used herein, the phrase "millimeter range" may refer to a distance that is less than 100 cm, particularly less than about 100 mm or less than about 10 mm. In a particular embodiment, the millimeter range is from about 0.1 mm to about 100 cm, from about 1 mm to about 100 mm, or about 1 to about 10 mm.

As used herein, "autistic spectrum disorder" or "ASD" refers to autism and similar disorders. Examples of ASD include disorders listed in the Diagnostic and Statistical Manual of Mental Disorders (DSM-V). Examples include, without limitation, autistic disorder, Asperger's disorder, pervasive developmental disorder, childhood disintegrative disorder, and Rett's disorder. Known ASD diagnostic screenings methods include, without limitation: Modified Checklist for Autism in Toddlers (M-CHAT), the Early Screening of Autistic Traits Questionnaire, and the First Year Inventory; the M-CHAT and its predecessor CHAT on children aged 18-30 months, Autism Diagnostic Interview (ADI), Autism Diagnostic Interview-Revised (ADI-R), the Autism Diagnostic Observation Schedule (ADOS) The Childhood Autism Rating Scale (CARS), and combinations thereof. Known symptoms, impairments, or behaviors associated with ASD include without limitation: impairment in social interaction, impairment in social development, impairment with communication, behavior problems, repetitive behavior, stereotypy, compulsive behavior, sameness, ritualistic behavior, restricted behavior, self-injury, unusual response to sensory stimuli, impairment in emotion, problems with emotional attachment, impaired communication, and combinations thereof.

The following examples are provided to illustrate certain embodiments of the invention. They are not intended to limit the invention in any way.

Example 1

Methods

Timeline of the Patient as Reported by her Doctors

MC is a 39-year-old, right handed woman who was pregnant when diagnosed with a grade 2 oligoastrocytoma on Mar. 5, 2014 after worsening headaches, fatigue, nausea and some degree of confusion which prompted an MRI scan. The MRI revealed on Mar. 7, 2014 a right frontal lobe mass lesion (8.5×5) with characteristics suggestive of oligodendroglioma. Surgical excision was recommended by the neurologist and scheduled for Mar. 12, 2014 in consultation with her high-risk Ob/Gyn. On the morning of Mar. 13, 2014 MC suffered an acute neurological decompensation with loss of consciousness and nonreactive dilated right pupil, sluggishly responsive pupil and decorticate posturing. It was thought that she had a seizure. She was intubated and given Mannitol and hyperventilated for probable increased intracranial pressure. A STAT CT of the brain revealed cerebral edema with uncal herniation. She underwent surgical decompression, a right hemicraniectomy with tumor debulking. EEG upon surgery did not reveal seizure activity. Postoperative exams included decerebrate posturing, CT and MRI. These tests revealed extensive hemorrhagic infarct or cytotoxic edema involving multiple vascular territories in the bilateral parietal temporal and occipital lobes, as well as bilateral (right more than left) thalami. Small foci of ischemia were also found on the right mid-brain, pons and right cerebellar hemisphere.

During the first week post-operation, MC remained unconscious. Her Glasgow Coma Scale (GCS) was 3. Even under comatose state she displayed spontaneous eye opening and movements in the extremities. Some examiners reported hand movement on command on Mar. 20, 2014, but subsequent reports have been inconclusive, possibly due to delays in response and inconsistencies in responses. On Mar. 20, 2014 an external ventricular drain was camped. An MRI on Mar. 23, 2014 revealed interval development of a large psudomeningocele at the right hemicraniectomy site. The external ventricular drain was removed on Mar. 24, 2014.

On May 22, 2014 MC underwent a C-section delivery of a healthy baby boy. On May 28, 2014 a percutaneous endoscopic jejunostomy tube was placed. She was transferred from the UCSF hospital to Kentfield Rehabilitation Hospital for neurorehabilitation.

At the hospital she had fever on Jun. 25, 2014 due to an infection. She underwent a course of antibiotics. A clot in her IVC was revealed by ultrasound on Jun. 26, 2014. She was fully anticoagulated prophylactically and fully anticoagulated with Lovenox.

Patient MC is on a trach collar. Her ABG on Jun. 30, 2014 showed adequate oxygenation. Her weekly scores on the Western Neuro Sensory Stimulation Profile (WNSSP) from Jun. 4, 2014 till Oct. 8, 2014 are reported on Table 1.

TABLE 1

Weekly scores from the Western Neuro Sensory Stimulation Profile (WNSSP) commonly used to track changes in neural sensory processing.

| Month | (Day) WNSSP | | | | |
|---|---|---|---|---|---|
| June | (4) 11 | (11) 10 | (18) 26 | (25) 27 | |
| July | (2) 27 | (10) 22 | (17) 22 | (24) 22 | (31) 29 |
| August | (6) 13 | (13) 14 | (20) 5 | (27) 17 | |
| September | (3) 7 | (10) 3 | (17) 10 | (24) 3 | |
| October | (1) 9 | (8) 14 | | | |

Discharge Medications

Medications administered per feeding tube: Amantadine 150 mg, 50 mg in the AM and 100 mg noon; Desmopressin 0.1 mg per day; Docusate 2 mg per day; Ferrous sulfate 300 mg; Folic acid 1 mg; Glycopyrrolate 0.5 mg; Keppra 1000 mg; Multivitamin (1 tablet); Potassium chloride 20 mEq; Senna two tabs; Vitamin D3 2000 IU; Aquatears to both eyes four times a day; Chlorhexidine 15 ml for oral care 4 times daily; Meropenem 1 g IV q 8.

Medications administered by subcutaneous bid: Enoxaparin 50 mg and Vancomycin 1 g IV.

Measurements

The wrist motions of patient MC were continuously captured in various daily sessions across the months of April till July 2014 using inertial measurement units (IMU; APDM opal, Portland, Oreg.). These IMU register linear and angular acceleration, surface skin temperature and magnetometer data at 128 Hz. The units are synchronized and operate through wireless technology in live streaming mode and also in robust logging mode. The former enables real time visualization of the synchronous data with no loss of data, while the latter allows the same without visualization of the recordings streamed in real time. Data is reported from the right and left wrists of the patient, synchronously recorded in robust logging mode (no data loss). Each session comprises several hours. Table 2 provides information on the number of hours per session when the data were registered. Statistical features of the data are described using new biometrics that connect acceleration-dependent motion and temperature data.

TABLE 2

Number of hours recorded by the APDM sensors per each day session across the 4 months.

| | Day, hours | | Day, hours | | Day, hours | | Day, hours | | Day, hours | | Day, hours | | Day, hours | |
|---|---|---|---|---|---|---|---|---|---|---|---|---|---|---|
| April | 24 | 7.09 | 25 | 7.22 | 26 | 7.16 | 29 | 6.41 | | | | | | |
| May | 3 | 9.45 | 6 | 12.56 | 8 | 12.28 | 11 | 3.45 | 13 | 6.26 | 17 | 6.74 | 27 | 12.24 |
| June | 5 | 3.57 | 8 | 11.33 | 12 | 7.32 | 20 | 13.29 | | | | | | |
| July | 1 | 9.34 | 9 | 7.06 | 12 | 9.43 | 15 | 4.32 | 17 | 5.37 | 19 | 7.14 | | |

Biometrics

The motion patterns were analyzed along with those of the temperature values, both registered simultaneously by the sensors. The analyses were focused on the linear acceleration obtained from the tri-axial linear accelerometers. To this end the linear acceleration is first expressed as the time series of the norm of the three-dimensional vector of accelerations expressed as a function of the temperature range in each section. The patterns of variability of the maximal instantaneous deviations of the acceleration from the overall mean acceleration across the session were examined using distributional analyses described in other work involving velocity- and acceleration dependent signals (Torres, E. B. (2011) Exp. Brain Res., 215:269-83; Torres, E. B. (2013) Front. Integr. Neurosci., 7:50; Torres, E. B. (2013) Behavioral Brain Functions 9:10; Torres et al. (2013) Front. Integr. Neurosci., 7:32 Torres et al. (2014) Front. Human Neurosci., 8:23).

FIG. 4 shows representative data from the patient's wrists. FIG. 4A shows the plots of the tri-axial acceleration profiles over several hours obtained on Apr. 24, 2014 (see also Table 2). FIG. 4B shows the profiles of temperature registered by the sensors while FIG. 4C shows the acceleration profiles. These are built as the time series of the instantaneous norm of the acceleration vector, $accel = \sqrt{(\vec{a}_1)^2 + (\vec{a}_2)^2 + (\vec{a}_3)^2}$ in a given session. Here the $a_i$ are the tri-axial components along the x, y, and z axes.

FIG. 4D shows the scalar acceleration expressed as a function of the temperature range registered by the sensors. The mean acceleration value and the instantaneous maximal deviation are taken from the overall mean of the session. These profiles are then obtained as a function of temperature. For each minute of the session all samples of the maximal deviation from the mean acceleration are obtained and plotted in matrix form in FIG. 4E (shown for a session in May 8, 2014) for 12.28 hours (739.6 minutes shown along the rows). The columns of the matrix show one-degree Celsius intervals spanning the range of temperatures for that session. The color of each entry in the matrix reflects for each minute and degree interval the maximal amount of motion deviating from the mean acceleration (see color bar) in units/s$^2$. FIG. 5 illustrates the steps followed to build these matrices. The acceleration and temperature data is first harnessed in one-minute-long intervals (128 Hz×60 sec, 7,680 registered frames). For each degree the range of motion registered is obtained over time. The example in FIG. 5 shows this for the 34-35° C.-interval. All motion data occurring in that interval is harnessed (inset in right panel). Then for each minute and each ° C. the maximal deviation from the mean acceleration is obtained. Across the minutes and degrees, these are the entries of the matrix depicted in FIG. 5. The color indicates the amount of motion maximally deviating from the mean acceleration of the session on May 8th.

In FIG. 6, the May 8th matrix is used to further illustrate the methods. The range from 33-35° C. is used to show the statistics of the motion. For each ° C., the number of maximal deviations (peaks) across the session (6.26-hours or 375 minutes along the rows of the matrix) were counted and were gathered in a frequency histogram. For each of the histograms representing the motions for each ° C.-interval, a probability distribution function was then fit. Using maximum likelihood estimation (MLE), estimates of the shape (a) and the scale (b) parameters of the Gamma probability distribution with 95% confidence intervals are obtained. The continuous Gamma family of probability distributions has been used to characterize the range of human motion variability across a range of neurological disorders and typical motions. From the Gamma estimated parameters, the Gamma statistical parameters (mean and variance) are obtained and then plotted on a ($\mu$, $\sigma$)-plane. Each point represents the Gamma statistical parameters of the acceleration-dependent motions for a temperature ° C.-interval taken across the time length of the session.

Noise-to-Signal Ratio Analyses

For each minute (comprising the 60 sec×128 Hz frames per minute) the above mentioned approach was also used to obtain for each entry in the matrix the Fano Factor. This is the variance divided by the mean, the noise to signal ratio. The resulting noise-to-signal ratio matrix corresponding to the motion matrix for the May 8th session is shown in FIG. 6A bottom panel. Notice here that at 25° C. the highest noise-to-signal level is revealed. FIG. 6B shows the frequency histograms for each of the 11 columns of the matrix corresponding to each ° C.-interval. The regimes with the highest (star) and lowest (star) noise levels detected at 25° C. and 32° C., respectively, were marked. This immediately indicates that not all motion from the accelerometers is physiologically relevant. At 25° C. for example this session reveals a pattern of motion whereby the motion noise registered by these accelerometers overpowers the signal. The range from 33-35° C. used in FIG. 7 to illustrate the methods are also marked here to show their range of noise-to-signal. Using the MLE procedure, the Gamma distribution shape and scale parameters of the distributions corresponding to the noise-to-signal values are estimated. This was done to determine the physiologically appropriate statistical regimes in the motion data to further analyze that data. These are regimes of temperature where the motion maintains minimal noise-to-signal ratios across the session, as opposed to the signal being overpowered by instrumentation noise. The estimated shape and scale parameters on the Gamma plane with 95% confidence intervals are plotted in FIG. 6C. The color code corresponds to the frequency histograms of 4B and the legend reflects the corresponding temperature ° C.-interval for this May 8th session. The points corresponding to the shape value of 1 (log-log plot along the horizontal axis is 100) are at the most random noise-to-signal levels. Those towards the right correspond to statistically more predictable (systematic) regimes of noise-to-signal levels (towards symmetric shapes of the distribution of the noise-to-signal ratios.) Along the scale axis, higher values indicate higher levels of noise (highest marked by blue star in correspondence with the frequency histogram in 4B). The 33-35° C. temperature interval used in 4B are marked to illustrate the methods to isolate the physiologically relevant motion regimes and in correspondence with the frequency histograms of the noise-to-signal ratio in 4B.

In summary, the motion statistical regimes for each minute and ° C.-interval (FIG. 6) are examined and then the noise-to-signal ratios corresponding to each of these acceleration-dependent motion entries are examined (FIG. 7). By combining temperature and motion of these sensors, one automatically extracts the range of physiologically relevant motion data to discriminate noise from signal. Then one can further perform longitudinal activity tracking analyses to blindly detect relevant changes in skin surface temperature and systematic or spontaneous acceleration-dependent motion patterns. FIG. 7 summarizes in matrix form the separation between relevant data and noisy data using the May 8th session as an example.

Automatic Blind Identification of Relevant Periods in the Longitudinal Data

The analyses of the evolution in the patterns of noise-to-signal ratio for one session can be extended to each of the sessions to assess the longitudinal evolution of the physiologically relevant data in each session. Recall that these are the data combining the minimal noise-to-signal ratios across the various °C.-intervals. FIG. 9 depicts the longitudinal stochastic trajectory of the noise-to-signal ratios extracted from the motion data across all sessions. There are 124 measurements automatically extracted from 21 sessions registered across 4 months (spanning from April to July). In each session several temperature °C.-intervals of low noise data were extracted and their shift in Gamma (b)-scale parameter levels obtained for each °C.-interval along with their shift in the Gamma (a)-shape parameter corresponding to the frequency histogram of the motion's noise-to-signal ratio and estimated using MLE. Notably, the Gamma (b)-scale parameter relates to the Fano Factor, the Gamma estimated variance divided by the Gamma estimated mean value. The former is a.b while the latter is a.b². The Fano Factor is then b, which is the scale parameter. Thus, the rate of change of the noise-to-signal ratio from the acceleration-dependent motions is being examined as they turn more or less random, and/or as they turn more or less systematic.

FIGS. 9A (right wrist) and 9B (left wrist) show the 3-dimensional trajectories of the changes in these Gama parameters (X-Y log-log plane) along the temperature ranges (Z-axis °C.) registered by the sensors. The vector field (black arrows) indicates the direction and the magnitude of the change in the reliability and predictability of the changes in the noise-to-signal ratio form the motion data. Low changes in values vs. high changes in values are better appreciated in FIGS. 9C-9D along the surface fitted through the 124 points of physiologically relevant (low noise) data across all sessions. Along the Z-axis of these surfaces are the changes in temperature level. Notice that the right wrist had a dramatically sharp change in the month of May, while the left wrist had a gradual change in temperature from June onwards. Points along the 0-change lines of temperature, scale and shape are steady states in each session.

Identification of and Further Distributional Analyses in Critical Sessions

Once the proper regimes of noise-to-signal levels are determined from the motion-temperature data, and their rates of change obtained, the stochastic analyses of the acceleration data is then used. The prior methods allow one to zoom in the month of highest (or lowest) change in activity across the longitudinal data. FIG. 10 shows the frequency histograms of the right and left wrists data involving the maximal deviations from the mean acceleration obtained within the proper temperature intervals (those identified with the lowest noise-to-signal levels). The figure focuses on the month of May which FIG. 9 identified as critical for the dominant hand. Notice the changes in the shape and width of these frequency histograms across the various sessions in May.

FIG. 11A tracks the stochastic trajectories of the estimated Gamma parameters for each wrist (corresponding to the acceleration-dependent motions) and identifies (with a star) in each case the session with the largest rate of change towards the regimes of lowest variability (most reliable) and most symmetric shape, towards systematic motions, away from the (most random) Exponential distribution regimes of the Gamma plane. The starting and ending points of the trajectories are also highlighted. FIG. 11B shows for each day the Gamma estimated statistics (mean and variance) highlighting in the legend the dates of the sessions and the largest change in statistical regimes. Other analyzes of the rates of change in these estimated parameters were performed for the month of May and for other months as well.

Results

Identification of the motion regimes with the lowest noise-to-signal ratio per session allowed for focusing on the physiologically relevant motion data and examining the rates of change of the width and the shape of the frequency distributions of the maximal deviation from the mean acceleration. The purpose of these analyses was to discriminate random from systematic changes in shape and scale parameters, as well as to establish possible relations between motion and temperature data.

FIG. 12A shows the result of the analyses corresponding to the stochastic changes in the shape of the distribution estimated for each of the sessions of each month where the noise-to-signal was at its minimum. The frequency distribution of the rate of change of the shape parameter in each session was well fit by the Gamma family. The estimated shape and scale parameters are plotted with 95% confidence intervals on the (log-log) Gamma Plane. This plane shows a clear separation in the clustering of the points corresponding to the sessions in the month of May for the right wrist. This separation is consistent with the overall behavior of the changes in temperature and motion data identified in FIGS. 9C and 9D. The upward shift in this cluster along the vertical axis indicates an increase in the variability (the width) of the shapes of the distributions of the acceleration-dependent motion parameter. The rightwards shift of this cluster along the horizontal axis indicates systematic changes towards more symmetric shapes. In summary these analyses revealed that the rate of change of the shape parameter estimated from the linear accelerations with the lowest noise-to-signal values singled out May as the critical month. This was the month with highest variability in the change of the shape parameter of the maximal deviations from the mean acceleration, but it was also the month when these changes were the most systematic. In other words, the variability in the acceleration-dependent motion of the dominant hand was not random during the month of May. The rate of change in the stochastic patterns was systematic.

FIG. 12B shows the results from similar analyses as in 10A but this time corresponding to the rate of change of the noise-to-signal levels in the surface skin temperature. The frequency distributions of the rate of change of surface skin temperature noise followed the Gamma distribution as well. The shape and scale parameters of each session were estimated with minimal acceleration-dependent motion noise and the point from each session was plotted on the (log-log) Gamma plane with 95% confidence interval. The month of May once again stood out as a separate cluster with shifts downwards towards regimes of reliable measurements (low noise) and shifts rightwards towards more systematic regimes tending towards symmetric shapes of the distribution of the rate of change in temperature noise. These patterns were not present in the values registered by the left wrist. In the left wrist the points from the sessions in the month of May did not cluster apart from those estimated from the measurements taken in the other months. Unlike in the right wrist, no reliable and systematic changes were revealed in the motions of the left wrist during the month of May.

FIG. 12C shows the patterns corresponding to the rate of change in the shape parameter discussed in 10A-B for the acceleration-dependent motion as a function of the temperature. The points representing the month of May cluster apart from the rest. Here, in relation to the other months, May had larger values for the change in the shape of the acceleration-dependent distribution corresponding to larger values in the change of the shape of the temperature-dependent distribution. This indicates a systematic change in the shapes of these distributions towards more symmetric shapes: as the changes in the shape of the distributions of temperature became more systematic so did the changes in the shape of the distributions of the maximal deviations from the mean acceleration. This means that in May the changes in the motions of the right wrist as a function of surface skin temperature were not random.

While FIG. 12C speaks of systematic changes in the shapes of the parameters' distributions, FIG. 12D speaks of the changes in their noise levels. In relation to other months, the measurements in the month of May stood out with lower changes in temperature noise and higher changes in acceleration noise. The rates of change in noise levels in temperature were steady, while the rates of change in the acceleration noise increased. There was more variability in the motion for steady temperature ranges. Yet this variability was systematic according to the statistics of the shape values of the distribution of motion parameters shown in the inset.

The inset zooms in the Gamma statistics of the changes in the shape of the distributions of maximal deviation from the mean acceleration. The figure shows that in May the motions were more systematic than in the other months and their variability in the shape of the distribution was higher. In particular, by May 17th the changes in surface skin temperature were steadier as the changes in motion patterns turned more systematic (as revealed by the higher values of the shape of the distribution of the relevant acceleration and temperature dependent parameters). Patient MC had the C-section delivery of her baby boy on May 22, 2014. All the data preceding that date indicated patterns of systematic variability in her motions from the dominant (right) hand that were absent in the motions from her non-dominant (left) hand. Furthermore, the medical records indicated the formation of a blood clot in the right arm after May. FIG. 9D shows a slow gradual increase in the changes in surface skin temperature for the left wrist that also coincided with higher levels of motion. These motions from the left wrist however had no discernable patterns of systematic changes in variability levels as those observed in May.

New methods are provided herein to assess in a personalized manner the longitudinal progression of body motions as a function of surface skin temperature using wearable sensors. The statistical metrics introduced here permit the continuous longitudinal assessment of patients as they move and as they undergo changes in physiological states. A particular case of post-sTBI has been used to illustrate the methods, yet these methods can be generally extended and used in other patients as well. These methods do not assume population statistics or expected values of the parameters of interest. Instead, they empirically estimate the probability distributions most likely underlying the changes in motion and physiologically relevant parameters registered in tandem within each daily session and longitudinally over months. The methods focus on the rates of change of these parameters' statistics along a continuum.

A surprising revelation from these analyses was that not all motions recorded by wearable sensors are physiologically relevant. A great deal of instrumentation noise was found that was separated from the signal in order to perform appropriate analyses on the motion data. This is important in light of the general use of wearable sensors in the market to track activity, wellness and fitness. Here high levels of noise-to-signal ratio were found in the acceleration data. The surface skin temperature was used as a natural filter to help separate the random rates of change of the noise levels in the motion from systematic rates of change. Systematic from random changes in the shape of the distributions of these parameters was also distinguished.

These data analyses indicate that in general more motion registered by accelerometers does not imply that there is more neural control of movements. The registration of higher acceleration values should not be associated with more volitional control or intent in the motions. Instead, one should separate the noisy data and assess the levels of reliability and systematicity in the data with low noise-to-signal ratio. In these sensors a layer of noise, particularly at low levels of temperature rendered irrelevant a large portion of high levels of motions registered by the tri-axial linear accelerometers. The lower temperature regimes coincided with motion data that was predominantly noisy. This was consistently the case across all sessions of recordings.

Notably, Newtonian mechanics concerned with acceleration estimations has no known relation to thermodynamics. The laws of mechanics governing physical motions were derived for inanimate objects and rigid bodies, rather than for biological bodies in motion undergoing physiological changes that impact the motions' variability. Although the field of neural control of movement employs primarily Newtonian mechanics in the analyses and modelings of behavioral states (Shadmehr et al. (2005) The computational neurobiology of reaching and pointing: a foundation for motor learning. Cambridge, Mass.:MIT Press), it may be important to introduce new ways of examining motion data in tandem with physiologically relevant measurements (such as temperature, heartbeat, breathing patterns, etc.) of use in clinical settings. An approach such as the one introduced here would then enable one to better understand the nature of motion data that is also governed by a nervous system and not exclusively described by the physical laws of motion.

While analyses and modeling of motion data is the exclusive focus of the field of neural control of movements without regards of physiological data, the medical field follows a complementary approach to patient assessment. In the clinical settings, measurements of physiological data such as temperature, breathing, heartbeat, etc. are routinely taken from the patient. These measurements are taken in isolation, without considering possible relationships to bodily motion patterns.

The human body is in constant motion in tandem with other physiological patterns of the person. Such patterns fluctuate and change over time. In clinical settings the absolute values of the parameters of interest are often registered, but very little is said about their rates of change over time. Here, it has been shown that the rates of change of those parameters over time contained information predictive of a relevant upcoming event. In particular, it was determined blindly that May was the month of highest relevance in these longitudinal data sets. A dramatic and sharp change in the patterns of motion and surface skin temperature of this patient's dominant hand manifested in May preceding the birth of her baby boy by C-section.

These metrics may be used to monitor critical events during pregnancy and foretell and even prevent potential problems. Here, the patterns of noise-to-signal corresponding to the painful contractions that are known to precede birth were captured and characterized. The methods may be used to characterize with unprecedented precision the risk of miscarriage as a function of age, as well as various individualized physiological scales of painful contractions as a function of temperature and motion profiles, among other symptoms during pregnancy. The former are now exclusively evaluated through subjective observational inventories and questionnaires.

This task of characterizing longitudinally the individualized profiles of various physiological stages of pregnancy in an objective manner can be performed using the new analytics presented herein in tandem with a broad range of wearable sensors available in the market. The current market offers sensors that capture heart rate variability, electro dermal activities, and blood-volume levels, among others. The outcomes of these biomarkers are currently examined in isolation. However, the analytics provided herein allow for integrating them with the motion's temporal profiles in a multi-dimensional setting. In such a setting, such physiological signals are used as natural filters to isolate systematic changes in bodily motion patterns that are physiologically relevant and independent of instrumentation noise.

By combining the motion and the physiological measures (registered in tandem), one can better and continuously monitor patients with post sTBI. One can better understand the course of individual changes in their motions and body physiology as the patient receives therapies and as the patient undergoes drug treatments. New ways to objectively track the progress of patients with post-TBI, identify critical points along the evolution of the person and assess the effectiveness of treatments in non-invasive ways can be performed.

Here, new analytics have been introduced that when paired with wearable sensors can track longitudinally physiologically meaningful patterns of motions under appropriate surface skin temperature regimes. The rates of change in the stochastic rhythms of such parameters, taken in tandem, singled out critical points and important trends in the trajectory of the patient's motions. In particular, these patterns blindly identified the periods of time prior to the baby's birth as one in which the bodily stochastic rhythms of motion and skin surface temperature reorganized and turned systematically predictable and reliable in the dominant hand. In the non-dominant hand the changes were registered much later and showing much more gradual (as opposed to sharp) trends.

In summary these sensor's physiological data were able to blindly forecast a significant biological event, even when the subject was under a coma state. The information revealed by this new analytical technology can also be used to individually track the longitudinal patterns of other patients with post-TBI and tailor their treatments accordingly. These new metrics can be used in true personalized medical practices.

Example 2

The human body is in constant motion, from every breath taken to every visibly purposeful action performed. Remaining still on command is one of the hardest things to achieve because micromovements across the body are hard to control under volition. Here, how head micromovements manifest in autism spectrum disorders (ASD) vs. healthy controls using shared data in the Autism Brain Imaging Data Exchange database is investigated. Since head-motion is detrimental for neuroimaging analyses, researchers ask participants to remain still and use motion-correcting methods to eliminate periods of high movement. Here, uncorrected resting-state scans from 605 participants were examined and excess noise and randomness in the head displacements and rotations of the ASD participants were found. Such patterns were exacerbated with psychotropic medications, but found as well without medication. The sensitivity and specificity of new individualized statistical biometrics to the sensory-motor patterns associated with the use of one or more commonly prescribed medications in the ASD cohort are reported, as well as interactions between specific medications and age. The signatures of micro-movement noise accumulation are a biologically informed core feature of ASD with medication-specific information to help assess risks and benefits of pharmacological treatments across different ages.

A critical need exists for new biometrics sensitive to various psychopharmacological treatments with the potential to detect interactions of such treatments across developmental stages. Under a new type of individualized statistical profiling such biometrics would automatically deliver objective oversight by dynamically tracking subtle changes in the sensory-motor patterns of the person's behaviors as well as blindly detecting self-emerging trends within a group. In line with the new platform of Precision Medicine (Hawgoog et al. (2015) Sci. Transl. Med., 7(300):300ps17), new personalized statistical approaches are needed in order to move beyond the "one-size-fits-all" current approach.

The traditional statistical approaches to the analyses of behaviors cannot address this need for personalized medicine in psychiatry because the data collected primarily represent observable behaviors and are analyzed under the assumption of normality and homogeneity. In contrast, data registered with high-resolution wearable sensors available today can capture subtle cumulative statistical changes in behavior that escape the naked eye. The statistical techniques used in other disciplines (e.g. physics, engineering, computational neuroscience, among other fields) can be adapted to the mental health and behavioral sciences to be used in the statistical estimation of sensory-motor patterns unique to each person. More specifically, instead of taking the mean and variance of motion parameters under the theoretical assumption of a Gaussian distribution, it is possible to empirically estimate the family of probability distributions that best characterizes the person's subtle changes in motor patterns underlying natural behaviors. The accumulation and rates of change in such minute fluctuations in moment by moment motor performance can then be statistically assessed as a function of context, medication class, combination of medications and dosages, among other factors that are known to interact and manifest through the person's physiological reaction to the drug. Likewise, because such patterns affect the person's motions and are automatically detectable with new technology, it is possible to examine the patterns of a given age group and unveil self-emerging trends across the population, i.e. without having to pre-impose a priori homogeneity assumptions for a given cohort.

Instead of predefining the hypothesis to test, as it is traditionally done, under the new approach one would let the inherent stochastic properties of the data automatically reveal the population trends. Other areas of medicine (e.g. cancer research) have succeeded at advancing their field towards personalized medicine. In psychiatry it has been challenging to do so. It has proven difficult to develop non-invasive data-acquisition methods that are sensitive enough to subtle moment-by-moment changes imperceptible to the observer. With the advent of access to large databases containing physiological data, demographic information and psychotropic medication-intake records, it is now possible to examine new questions using a personalized statistical approach. This new possibility is explored here in individuals with a diagnosis of Autism Spectrum Disorders (ASD) and typically developing controls (TD) using records from the Autism Brain Imaging Data Exchange (ABIDE) (Di Martino et al. (2014) Mol. Psychiatry 19:659-667).

Paradoxically, it is often the case that when investigating mental disorders that are defined by observable behavioral disturbances, most brain research requires the patient (and the control participants) to curtail overt behavior and be motionless at some stage of the experiment. For instance, studies of perceptual processing require eye-fixation at some stage. Electroencephalographic (EEG) data acquisition becomes plagued with artifacts whenever the participant blinks, and functional magnetic resonance imaging (fMRI) experiments require maximal damping of head movements while lying inside the magnet so as to prevent artifacts that emerge from natural micro-motions (Deen et al. (2012) Nature 491:S20). Even upon padding the head inside the magnet, these minute fluctuations are detectable and known to confound the data if no cancellation procedures are in place (Deen et al. (2012) Nature 491:S20; Hutton et al. (2002) Neuroimage 16:217-240; Jenkinson et al. (2002) Neuroimage 17:825-841; Friston et al. (1996) Magn. Reson. Med., 35:346-355). In this sense it is possible for one to take advantage of current methods used to detect micromotions of the head between scans. Instead of throwing away that data as a nuisance, it is used herein in combination with new statistical methods developed for the personalized profiling of micro-motions signatures underlying the movements of natural behaviors.

Recent work has shown that sensory-motor issues underlie many of the socio-motor axes of behavior that are affected in individuals with ASD (Fournier et al. (2010) J. Autism Dev. Disord., 40:1227-1240; Haswell et al. (2009) Nat. Neurosci., 12:970-972; Gidley Larson et al. (2008) Brain 131:2894-2903; Gowen et al. (2013) J. Autism Dev. Disord., 43:323-344; Jansiewicz et al. (2006) J. Autism Dev. Disord., 36:613-621; Donnellan et al. (2012) Front Integr. Neurosci., 6:124). Perhaps these anomalies are also detectable in head micromotions, particularly as the person rests, presumably motionless. Such patterns, if they existed in ASD, would help determine the levels of volitional control of the person. In the context of medication intake, these patterns as measured by instrumentation, would inform of subtle changes that the clinician may miss by relying on mere observation. Moreover, the well-functioning of the vestibular system, important for head stability from an early age, depends greatly on the proper sensory-motor integration from various visual, auditory and neck proprioceptive channels (Purves, D. *Neuroscience* 4th Ed., (Sinauer, 2008)). Many of the vestibular system's functions well known to be affected in ASD (Ogawa, T. (1989) No To Hattatsu 21:163-169; Ayres et al. (1980) Am. J. Occup. Ther., 34:375-381) are functional targets in pediatrics sensory-motor driven occupational therapies. However, ASD has no sensory-motor core definition and there is no way to objectively quantify the effectiveness of such interventions.

If the anomalies in the signatures of body movement variability found in ASD (Fournier et al. (2010) J. Autism Dev. Disord., 40:1227-1240; Haswell et al. (2009) Nat. Neurosci., 12:970-972; Gidley Larson et al. (2008) Brain 131:2894-2903; Gowen et al. (2013) J. Autism Dev. Disord., 43:323-344; Jansiewicz et al. (2006) J. Autism Dev. Disord., 36:613-621; Donnellan et al. (2012) Front Integr. Neurosci., 6:124) also extended to the head micro-movements, particularly when the person is lying down with the head padded to dampen these motions, this would indicate that corrupted motor output variability is a systemic problem, signaling a failure to anticipate sensory consequences of the impeding actions in these individuals. In such scenario, besides aiding clinicians and therapists in the design of clinical outcome measures, these tools could help researchers to characterize ASD objectively from head-to-toe and to add a putative specific disorder type (e.g. head-trigeminal-ganglia- vs. body-dorsal-root-ganglia-noise prevalence) to the list of infantile neurological sensory-motor disorders of the nervous systems.

Several of the neurodevelopmental disorders that are officially recognized by the Movement Disorders Society as a movement disorder (e.g. Tourette's, Fragile X related motor disorders, etc.) also have a diagnosis of ASD during childhood (Niu et al. (2014) Parkinsonism Relat. Disord., 20:456-459; Hagerman et al. (2010) Mol. Autism 1:12). Because of this comorbidity, if in addition to the social axes, ASD were conceptualized as a set of sensory-motor disorders, the various subtypes of ASD could be objectively identified, treated and tracked, above and beyond descriptive observation and psychological interpretation of the behavioral phenomenology of this broad spectrum of disorders. Of note, the early definitions of mental illnesses in the early half of the 20th century were primarily founded on motor and neurological issues (Rogers, D. M. *Motor disorder in psychiatry: towards a neurological psychiatry* (J. Wiley & Sons, 1992)). Part of the reason why an entirely different, namely a more embodied approach is needed is because current diagnostic categories of mental illnesses are symptom-based: in fact, they were not designed to be biologically valid (Insel, T. R. (2014) Am. J. Psychiatry 171:395-397).

The approach provided herein speaks to the Research Domain Criteria (RDoC), a recent initiative of the National Institutes of Mental Health (NIMH) that addresses a strategic objective to "Develop, for research purposes, new ways of classifying mental disorders based on dimensions of observable behavior and neurobiological measures." Thus the aim of RDoC is to identify core features—some yet undiscovered or underutilized—that cut across research domains and that use rigorous scientific method (Insel, T. R. (2014) Am. J. Psychiatry 171:395-397). Specifically, RDoC addresses the lack of validity of the Diagnostic Statistical Manual (DSM) for mental illness (as well as in the International Classification of Diseases (ICD)), but it is at present lacking a motor domain (Bernard et al. (2015) Psychol. Med., 1-5). In this sense, the micro-movements would enable a form of personalized precision phenotyping as part of the broader NIH's Precision Medicine initiative.

The head micro-motion data obtainable from a large number of functional neuroimaging datasets deposited in the Autism Brain Imaging Data Exchange (ABIDE) database (containing datasets of 1,112 individuals with and without ASD), offers researchers a unique opportunity to characterize normative data and better profile ASD. To this end, a new statistical platform is used herein for the personalized analyses and sensory-motor profiling of the variability inherent to resting-state behavior.

The data that are a nuisance to other fields could serve the investigation in determining if the sensorymotor disorders that have been systematically quantified across the body in ASD are also present in the micro-movements of the head. If micro-movements' disorders were a systemic feature of ASD and if they were present in individuals currently on or off psychotropic medications, across multiple age groups, one can use these new techniques to provide a personalized dynamic measure of 'precision phenotyping' of ASD as the disorder evolves in time with and without medication. This would enable steering away from symptom-based medication towards individualized target treatments, in line with the current goals of Precision Medicine.

Materials and Methods

Experimental Design

Datasets used in this study were obtained from public, freely accessible Autism Brain Imaging Data Exchange (ABIDE) database (fcon_1000.projects.nitrc.org/indi/abide/). Data are de-identified in compliance with U.S. Health Insurance Portability and Accountability Act (HIPAA) guidelines.

Participants at all sites signed written informed consent and assent (and parental consent, if participants were less than 18 years) in accordance with U.S. 45 CFR 46 and Declaration of Helsinki for participation; research protocols which included neuroimaging and clinical assessments at each site, were approved by the local ethics committees. Analyses of these de-identified data were reviewed and approved by Institutional Review Boards of Rutgers University and Columbia University Medical Center.

Inclusion/Exclusion Criteria

In the current study, ABIDE sites were included that (i) deposited raw resting-state functional Magnetic Resonance Imaging (MRI) scans (i.e., no motion correction or "scrubbing" (Power et al. (2012) Neuroimage 59:2142-2154) was applied to these data), (ii) had a total scan duration at least 8 minutes, and/or (iii) had at least 15 individuals with ASD. Seven of 16 ABIDE sites met these overall inclusion criteria: University of Michigan, Sample 1 and Sample 2 ("UM_1" and "UM_2", respectively), University of Utah School of Medicine ("USM"), New York University Langone Medical Center ("NYU"), University of California, Los Angeles, Sample 1 ("UCLA_1"), Olin, Institute of Living at Hartford Hospital ("OLIN"), and University of Pittsburgh School of Medicine ("PITT").

Full batteries of non-parametric (distributional) analyses were performed on datasets from the 3 sites that met criteria (i) and (ii), UM_1, UM_2, and USM. A complementary set of analyses was performed for the four remaining sites (NYU, UCLA_1, OLIN, and PITT) that deposited raw data with a shorter total scanning time (i.e., that could not be subjected to the full battery of non-parametric distributional analyses) but that had met criteria (iii). Note that NYU excluded individuals with the most severe head movement from the dataset but otherwise no motion correction was applied to the deposited data. All datasets deposited by each of the seven sites were analyzed.

Datasets from a total of 605 participants were analyzed, including 304 individuals with Autism Spectrum Disorder (ASD) and 301 typically developing (TD) controls. Specifically, 246 datasets were analyzed from the three main sites broken down as: UM_1 (NASD=55; NTD=55), UM_2 (NASD=13; NTD=22), and USM (NASD=58; NTD=43) (Total: NASD=126, NTD=120). The rest of the sites included 178 ASD and 197 TD controls. These data break down as: NYU (NASD=79; NTD=105), UCLA_1 (NASD=49; NTD=33), OLIN (NASD=20; NTD=16), and PITT (NASD=30; NTD=27) (Total: NASD=178; NTD=181).

Demographic Characteristics

Main analyses datasets. Participants at the three main sites (UM_1, UM_2, USM) did not differ in age 17.51 (7.28) (mean and standard deviation; range: 8.5-50.22) for the ASD group, and 17.14 (6.22) (range: 8.2-39.39) for the TD group (p=0.67). Participants did not differ in sex (ASD: 116/10 (Males/Females); TD: 102/18 (Males/Females) (X2=3.04, p=0.08). 103 ASD participants were right-handed, 14 were left-handed, 1 was ambidextrous; 105 TD participants were right-handed and 12 were left-handed. Scores were missing for 8 ASD and 3 TD participants.

Additional datasets. Participants at the four other sites (NYU, OLIN, UCLA_1, PITT) also did not differ in age 15.13 (6.06) (mean and standard deviation; range: 7.13-39.1) for the ASD group, and 15.88 (5.80) (range: 6.47-33.24) for the TD group (p=0.22). Participants did not differ in sex (ASD: 153/25 (Males/Females); TD: 145/36 (Males/Females) (X2=2.17, p=0.14). 149 ASD participants were right-handed, 26 were left-handed, 2 were ambidextrous; 168 TD participants were right-handed and 8 were left-handed. Scores were missing for 1 ASD and 5 TD participants.

Psychotropic Medication Intake

All sites in the current study, except USM, reported whether or not ASD participants were currently taking medications. Only one site in the current study, NYU, asked patients on stimulants to withhold their intake during the scan day. Reported medications were classified into nine classes: 1) antidepressants (Fluoxetine, Sertraline hydrochloride, Trazodone, Escitalopram, Citalopram, Bupropion, Mirtazapine, Duloxetine hydrochloride, Venlafaxine, Paroxetine), 2) stimulants (Amphetamine, Dextroamphetamine, Lisdexamfetamine, Methylphenidate Extended release, Dexmethylphenidate, Dextroamphetamine sulfate), 3) anticonvulsants (oxcarbazepine, valproic acid, lamotrigine), 4) atypical antipsychotics (risperidone, ziprasidone hydrochloride, asenapine, quetiapine, aripiprazole), 5) benzodiazepine anticonvulsant (lorazepam), 6) alpha agonists (guanfacine, clonidine), 7) atypical ADHD medication (NRI; atomoxetine), 8) nonbenzodiazepine sedative-hypnotic (eszopiclone), and 9) nonbenzodiazepine anxiolytic (buspirone).

Specific Instructions at each Site to Participants During the Resting Scan

Participants at the 3 main sites (UM_1, UM_2, and USM), as well as at UCLA_1 and OLIN were asked to keep their eyes open. At NYU, most of the data were contributed from studies that asked participants to keep their eyes open during the scan, but also included data from studies that asked participants to keep their eyes closed. Participants at the Pittsburgh School of Medicine were asked to keep their eyes closed. Additional information on eye status for each site is reported at fcon_1000.projects.nitrc.org/indi/abide/.

MRI Acquisition Parameters

Resting-state functional MRI (rs-fMRI) Blood Oxygenation Level Dependent (BOLD) data were acquired on GE (GE Medical Systems, Milwaukee, Wis.) or Siemens (Siemens Healthcare, Erlangen, Germany) 3 Tesla MR scanners. BOLD signal was obtained with T2*-weighted echo planar imaging (EPI) sequence for all of the seven sites used in the present study. All three main sites had identical inter-scan interval (repetition time=TR) of 2000 ms (½ Hz temporal resolution), and a comparable total scan duration. UM_1 and UM_2 scans were 10 minute each (300 volumes) and USM was 8 minutes (240 volumes). NYU scan was 6 minutes (180 volumes; TR=2000 ms (½ Hz)); OLIN scan was 5 minutes 15 seconds (210 volumes; TR=1500 ms (1/1.5 Hz)); UCLA_1 scan was 6 minutes 6 seconds (120 volumes; TR=3000 (⅓ Hz)); PITT scan was 5 minutes 6 seconds (200 volumes; TR=1500 (1/1.5 Hz)).

Pre-Processing of Raw Resting-State Image Files

Head movement parameters were obtained using Statistical Parametric Mapping (SPM8), a freely available software for processing neuroimaging data (fil.ion.ucl.ac.uk/spm/software/spm8/) and in-house code running MATLAB version 8.3 (R2014a) (The MathWorks, Inc., Natick, Mass.).

Head movements introduce changes in signal intensity of collected volumes over time and represent a major confound in neuroimaging (Friston, K. J. in *Statistical Parametric Mapping: The analysis of functional brain images* (eds. K. J. Friston et al.) (Academic Press, 2008)). Thus, software for processing MRI data commonly include a motion estimation component (In SPM, the 'realign' component includes 'estimate' and 'reslice'; the 'reslice' function resamples the volumes using estimated motion parameters).

In SPM, realignment of scanned volumes involves estimating the six parameters of an affine 'rigid-body' transformation (b-splines interpolation using least-squares approach) that minimizes the differences between each successive scan and a reference scan (Friston, K. J. in *Statistical Parametric Mapping: The analysis of functional brain images* (eds. K. J. Friston et al.) (Academic Press, 2008);

Friston et al. (1995) Human Brain Mapping 2:165-189). The default reference scan in SPM8 is the first scan (volume), to which all subsequent volumes are realigned. The output with the six motion parameters (3 translations in x, y, z directions, and 3 rotations: pitch (about x-axis), roll (about y-axis), and yaw (about z-axis)) is recorded as an rp_%s.txt file. Raw NIfTI (.nii) files were separately processed for each site in the ABIDE database used in the current study because of differences in the inter-scan interval (Repetition Time, TR), number of slices, and total scan duration (number of volumes) across sites. Whenever the data from all 7 sites were pooled, ratios were defined that would consider the above mentioned sampling disparities across datasets.

Analytics

Definition of micro-movements: Small trial-by-trial variations in performance as captured by fluctuations in the amplitude or the timing of critical kinematic parameters. These may include velocity- and acceleration-dependent parameters such as the maxima, the minima, and the time to reach the peaks, or the inter-peak interval timings along continuous time series of changes in the positions of some parameter from some physiological signal, etc. This definition should not be confused with small movements or with sub-movements comprising a single movement or motor actions. The present experiment assesses the scan-by-scan velocity-dependent variations in the linear displacement and in the angular rotations of the head's small motions. The analyses refer to the stochastic signatures of those minute motor variations, their accumulation and individualized empirically-estimated statistical features.

The rate of change of linear displacement (angular rotations) was obtained in vector form (a three-dimensional velocity field over time). For each velocity vector the Euclidean norm was used to obtain the magnitude of each element in this scalar field over time, i.e. the linear speed profile corresponding to the given session. In the cases of the angular velocity the three rotational components were treated as Euler angles and converted to quaternions for proper use of the Euclidean norm on the angular velocity field. The resulting scalar field was used as the angular speed profile over the given session. The time series of the speed values was then plotted for each participant as a profile in time, measured (in seconds) across the length of the scanner session.

The pooled data across all participants of a given study divided into ASD and controls was also obtained. Representative ensemble data for the UM_1 study are shown in FIG. 13 of the main text. Notice the differences in speed magnitude between ASD (FIG. 13A) and controls (FIG. 13B). These data sample comprises 55 participants in each participating group of the UM_1 study with 300 scans each. The speed maxima were gathered into a frequency histogram for each group as well as into a cumulative probability density function to contrast the two groups. These are shown in FIG. 13C along with the empirically estimated shape (a) and scale (b) parameters of the continuous Gamma family of probability distributions. The Gamma probability distribution function is given by:

$$y = f(x|a,b) = \frac{1}{\Gamma(a)b^a} x^{a-1} e^{\frac{-x}{b}}$$

in which a is the shape parameter, b is the scale parameter, and $\Gamma$ is the Gamma function (Ross, S. M. *Stochastic processes* 2nd Ed. (Wiley, 1996)).

The Gamma parameters are empirically estimated using maximum likelihood estimation with 95% confidence intervals. The estimated parameter for each individual is plotted on the Gamma plane with confidence intervals to compare the individual to others in the cohort. The data from ensembles of participants is also pooled and the Gamma parameters estimated and plotted on the Gamma plane with confidence intervals to compare different groups in the database.

The noise to signal ratio the Fano Factor (FF) (Fano, 1947) obtained from the empirically estimated Gamma variance divided by the empirically estimated Gamma mean. The Gamma mean is given by $\mu = a \cdot b$ and the Gamma variance is given by $\sigma = a \cdot b^2$. Notice that the noise-to-signal ratio, the Fano Factor in this case is also the Gamma scale parameter:

$$b = \frac{\sigma^2}{\mu} = \frac{a \cdot b^2}{a \cdot b} = b$$

This is important as one will be assessing the levels of noise in relation to the empirical estimation of the Gamma parameters from the data as a function of group type, medications and age. Higher levels of noise will correspond to increases of the b scale parameter along the vertical axes of the Gamma plane; whereas lower levels of noise will correspond to lower values along the scale axis of the Gamma plane.

When the shape parameter a of the Gamma family a=1, the data follows the memoryless Exponential probability distribution. This is the most random distribution whereby events in the past do not accumulate information predictive of events in the future. Larger values towards the right of the shape axes on the Gamma (a, b)-plane tend towards the symmetric distributions, with a variety of skewed distributions in between the two extremes.

Below, the level of randomness in the empirically estimated shape parameter (when close to a=1) or increasing in predictability (the accumulation of information towards the prediction of an expected value) when away from a=1. Likewise higher or lower noise levels according to the empirically estimated b Gamma scale parameter value, which is the FF. Kruskall-Wallis test (non-parametric one-way ANOVA test) is used to assess the statistical significance of the differences in the empirically estimated Gamma parameters between the two participant types.

FIG. 13D shows the results of the median noise-to-signal ratio compared between the two groups. The speed maxima were normalized to avoid allometric effects due to scan length and sampling resolution differences across sites and studies. To this end, the average speed value between each two local minima in the time series were obtained. Each speed maximum was then divided by the sum of the speed maximum and the average speed between the two corresponding minima. The same procedure explained for FIG. 13 was then applied to the normalized speed maxima (denoted normalized peak velocity index, PV index). Smaller values of this index indicate larger values of the average speed in the denominator (i.e. faster rates of change in linear (angular) displacements (rotations) on average). Since there is interest in the cumulative effect over time and their rates of change across the scanning session, the empirical cumulative probability distribution function (eCDF) for these speed-dependent parameters (i.e. average speed, PV index, etc.) was also obtained.

The empirically estimated Gamma shape and scale parameters were plotted as points on the Gamma plane, each representing a study site for the ensemble data. In the cases where the ensemble is unfolded into its individual participants and an individualized estimation procedure is performed, each point corresponds to the stochastic signatures of a single participant. In the latter case, a scatter was obtained and studied on the log-log Gamma plane in search for power law relations. The power law relation obtained is reported with the goodness of fit parameters. The fitting error between the line obtained using the estimated exponent of the power relation (the slope of the line) and the data point from the scatter was obtained for each participant and their histograms compared between ASD and controls. The Gamma scale parameter (i.e. the noise to signal ratio or Fano Factor) was plotted as a function of this error (denoted here delta) and statistical comparisons performed along each dimension. Lastly the Gamma statistics (the empirically estimated Gamma mean and Gamma variance) were plotted against the delta to fit a surface across the signatures of all ASD participants and those of the controls.

To probe the role of psychotropic medications in the level of noise in the displacement and in the rotational head micro-motions, the data from ASD participants who were currently taking psychotropic medications was analyzed, relative to ASD participants who were medication-free as well as TD controls. Noise analyses were conducted using participants from the two sites with the longest scan duration, UM_1 and UM_2 (note that USM did not report medication intake) as well as using pooled data from all study-sites.

Data from ASD participants was analyzed (i) by the number of medications taken, regardless of drug class—whether they were on two or more medications or on three or more medications, (ii) by specific class, whether or not participants were taking this medication along with other medications—a situation referred to as a "combination treatment", (iii), by specific class in isolation, meaning that participants took one and only one medication belonging to a given class and no other medications with it. Analyses in i-iii were conducted relative to medication-free ASD and TD participants. In such comparisons hundreds of speed spikes were gathered across participants per medication sub-group and the above-mentioned Gamma distributional/statistical analyses performed. These analyses were then performed as a function of age groups to elucidate medication-age interaction effects. Five age-groups were identified in the data set for which a sufficient numbers of ASD participants were available per medication class to perform these statistical estimation analyses. Group 1 was comprised of participants ranging between 6 and 10.99 years old. Group 2 was between 11 and 12.99 years old. Group 3 was between 13 and 14.99 years old. Group 4 was between 15 and 16.99 years old. Group 5 included all participants over 17 years old (between 17 and 50 years old).

The following classes were possible to use in the analyses where the patient was taking the medication class as part of a combination-treatment in ii: antidepressant, anticonvulsant, alpha agonist, atypical ADHD, atypical antipsychotic and stimulant. The following classes were possible to use in the analyses where the patient was taking the medication class in isolation, without any other medication in iii: antidepressant, stimulant, atypical antipsychotic, atypical ADHD medication. The results of these analyses are shown in FIG. 16, also pooling patients across all study-sites (except USM).

Results

Noise and Randomness of Micro-Movements in ASD

FIG. 13 illustrates analyses of the magnitudes of the rates of change of linear displacements, shown here for UM_1 site, using pooled data across all participants within each of the ASD and TD groups (similar trends were found for the rates of change of the head's angular rotations). First, FIGS. 13A and 13B show qualitative differences in the magnitude of the raw, scan-by-scan head micromotions between ASD and TD participants, whereby ASD patients have noticeably higher and more frequent head fluctuations. The differences in these speed maxima were quantitated using frequency histograms presented in FIG. 13C, which show rapid accumulation of these peaks in the ASD group. Note that the squared log of the raw peak speed values was used for better visualization of the significant statistical disparity seen in FIG. 13A. The differences between the empirical cumulative distribution functions (eCDF) for these two empirical samples were statistically significant ($P<10^{-17}$, Kolmogorov-Smirnov test). The empirically estimated Gamma shape and scale parameters are also shown in FIG. 13C (plotted on the Gamma plane with 95% Confidence Intervals, CIs). This unambiguous quantitative difference between ASD and controls in the Fano Factor (i.e., the noise-to signal-ratio, b-scale Gamma parameter) was captured using non-parametric one-way ANOVA (the Kruskall-Wallis test) yielding statistically significant differences (df column, error, total (1, 108, 109), $\Gamma^2 17.2$, $P>\Gamma^2 3.38\times10^{-5}$).

The presence of statistically significant group differences was found in the noise and randomness levels within each dataset that were analyzed. FIG. 14A shows the normalized speed maxima index denoted peak velocity (PV) index for each of the three main sites. Across the 3 main studies (UM_1, UM_2 and USM) it was possible to differentiate ASD from control participants as the Gamma parameters and the estimated mean and variance separated these individuals.

FIG. 14B shows the eCDFs while FIG. 14C shows the estimated Gamma statistics (mean and variance) for ASD and TD participants. The insets show the differences in the empirical cumulative distribution functions of the PV index pooled across the ensemble of the three studies. Note that these group differences held independently for NYU, UCLA_1, OLIN, and PITT sites and are presented for both linear displacements and rotations.

FIG. 14D unfolds the ensemble data for all participants from the 3 main studies of comparable temporal resolution and scanning times. Using this large group (N=246; includes 126 ASD and 120 TD participants) a power law relation $f(x)=a \cdot x^b$ was found between the scale (a) and shape (b) estimated Gamma parameters (a=0.53 [0.52, 0.54], b=−0.99 [−1.0, −0.98], goodness of fit SSE 1.49e-05 and adjusted $R^2$ 0.99, RMSE 0.00037). Statistically significant differences for both estimated parameters were confirmed between ASD and TD controls (Friedman test, df columns, interaction, error, total (1, 1, 216, 219), $\Gamma^2$ 163.51, $P>\Gamma^2$ $1.93\times10^{-37}$). The results of the noise-to-signal comparison using scatter and box plots are shown in FIG. 14D. FIG. 14E shows the estimated probability density functions for each participant in the ensemble of each group. This figure underscores the differences between the variability patterns of head micro-motions between ASD and controls.

The normal distance from each point representing a participant's stochastic signature to the unit line from the power law relation characterizing the scatter on the Gamma plane was obtained (denoted delta) and the noise to signal ratio plotted as a function of this residual value in FIG. 14F.

Noisy Cluster Within ASD Group

The analyses of the Fano Factor revealed in the ASD group a subset of individuals with higher noise levels than that in the TD group (i.e., with FF above 0.06, about 2.5 standard deviations from the mean, in FIG. 14F). Closer inspection of this ratio revealed higher levels of variability in ASD. The scatter was examined along three dimensions comprising the mean, the standard deviation and the delta residual as a measure of failure to follow the power law. This is shown in FIG. 15A for controls and FIG. 15B for ASD. FIGS. 15C-15E show the box plots resulting from the Kruskall-Wallis test that yielded significant differences between ASD and TD participants for each of these dimensions (at the alpha 0.01 level). The surface fitted to the scatter revealed that the subgroup with higher noise levels was comprised of some ASD participants that were currently taking at least one psychotropic medication and some that were not.

The Role of Psychotropic Medications in Noise and Randomness Levels in ASD

Motivated by the above-mentioned results, it was first asked whether there is an effect of taking two or more medications (regardless of class) on patterns of micro-movement signatures. The ASD sub-groups included participants taking no medications, two medications and three medications from the UM_1 and UM_2 study-sites included in FIGS. 14-15.

FIG. 16A shows the results of this comparison on the Gamma plane. Systematic increase in the levels of noise (upwards shift along the scale, the noise-to-signal ratio axis) and in randomness (leftward shift along the shape axis towards a=1 the special case of the memoryless Exponential distribution) of the head micro-movement signatures was found. Consistent results were found for microdisplacements and micro-rotations. The number of medications taken pulled the stochastic signatures of head micro-motions of medicated ASD participants away from those of TD controls. The medicated ASD with 3 medication-combination-treatments were the farthest apart from TD controls. They fell along the directions of the Gamma plane towards the random exponential distribution, and with higher levels of noise-to-signal ratio than controls.

FIG. 16B shows the differences in the total cumulative distances traveled along the linear and angular domains for each patient. This comparison includes two studies (UM_1 and UM_2) in FIGS. 14-15 that reported medication intake by participants, with 300 frames per participant (both studies at ½ Hz). These were used because they had congruent fixed scanning rate needed to be able to compare the cumulative linear and rotational total excursions of the head during the session. A statistically significant systematic increase was found with medication quantity between medicated ASD and TD controls (P<0.01), meaning that statistical patterns were significantly worse for ASD participants taking multiple medications. This difference in shape and scale was also consistent between medicated and non-medicated ASD, as well as, notably, between non-medicated ASD and controls.

Effects by Medication Class per Age Group (Taken with Other Medications)

The medication information by medication classes broken down into different age groups was then examined Given the broad range of ages in the sample (6 to 50 years old) it was desirable to elucidate several questions. First, the classes that were most likely driving the statistically significant effects of medications on the head micro-movement patterns of ASD participants was investigated. Second, it was asked whether age was a factor with variable effects (i.e. across medications). If so, it was asked which age group accounted for the worst increase in noise and randomness levels away from the non-medicated ASD, and which age would pull the medicated-ASD towards the controls (with highest reliability and predictability in the speed dependent signal). Lastly it was investigated whether there was an overall medication-class trend. Given the systematic deleterious pattern uncovered by the medication quantity, the corresponding noise-pattern order per the medication class, when this class was part of a combination treatment, or taken in isolation. For each group, it is also highlighted which medication is likely to be prescribed most frequently (i.e., as reported in the ABIDE database for these study-sites).

FIG. 17A shows the panels with translation (T) and rotation (R) for different age groups (G1-G5). Notice that when taken as part of a combination, the anticonvulsants, across all age groups and for both translation and rotation speeds, correspond to data points that are the highest along the scale axis and the lowest along the shape axis, i.e. the farthest from the TD controls. The systematic order is shown in the FIG. 17 legend with atypical antipsychotic at the lowest end, closer to TD controls. The effects on medicated ASD were different across age groups maximally pulling them away from TD in the oldest age group 5. In contrast other medication classes pulled them towards the TD group in the younger groups (G1-G3). The most prescribed medication in combination is the alpha-agonist in the youngest group (6 to 11 year olds), whereas antidepressant and stimulants are the most prescribed in the oldest group (those above 17 years old). Anticonvulsants abound in groups 2 and 3 (spanning 11 to 15 year olds) whereas group 4 (16 to 17 year olds) has the atypical ADHD medication as the most prescribed in combination with others.

Effects by Medication Class per Age Group (Single Medication)

The effects when a given medication class is taken in isolation was investigated. FIG. 18 shows the results across age groups (in the case of missing medication class, it was not included). Here, one can see a clear trend whereby the younger medicated ASD groups are pulled away from the non-medicated ASD participants, towards the TD participants, indicating a benefit. In groups with older participants this trend is opposite. Examination of these older age groups shows that the patterns of medicated ASD participants systematically pull away from those of the TD participants. The older the person the more deleterious the effects are in the noise-to-signal ratio of the speed-dependent parameters and the farther away from symmetric (Gaussian-like) distributions that the TD manifest. The examination of the proportions of medications across age groups revealed that the atypical antipsychotics are likely to be the most prescribed in the youngest group while the oldest participants (congruent with the analyses above) have a higher percentage of antidepressants and stimulants prescribed to them.

Herein, it has been shown that when asked to remain still, participants with ASD have more difficulty volitionally controlling their head micro-movements relative to the age- and sex-matched TD participants across each of the seven ABIDE study-sites. The stochastic signatures of speed-dependent translational and rotational head motions rapidly and randomly accumulate noise, an effect that systematically worsens with intake of psychotropic medication (FIG. 14). These deleterious statistical patterns were present when the participant took the medication class as part of a combination as well as when the medication type was taken in isolation. Besides revealing an objectively quantifiable trend in ASD as a group, specific effects of medication classes and interactions with age were found. In particular, when a drug from a given class was taken in isolation (i.e., not as part of a combination treatment), ASD participants in younger age groups showed stochastic patterns that were closer to normative patterns of age- and sex-matched TD controls (FIG. 16). This result provides evidence that younger patients with a diagnosis of ASD may in some instances benefit more from a single drug class than from the interactions of multiple medications. Likewise in older participants an opposite effect was detected. This opens several lines of questions regarding the age of the person being prescribed a drug to alleviate symptoms as well as the amount of time a person may be on a medication class before treatment visibly interferes with motor control. The biometrics presented here reveal on the Gamma parameter plane the relative distances to normative patterns. These assessments can serve as an objective outcome measure to help guide physicians ascertain the individualized benefits and/or the risks of drug class(es) to treat a given patient.

The results on the signatures of head micro-motions are congruent with recent findings on bodily- and limbs-related micro-motions (Torres et al. (2013) Front. Integr. Neurosci., 7:32), indicating that lack of volitional control may be a systemic problem in ASD that can be measured across the body with high precision instrumentation and new personalized statistical platform. This work shows that a physical measure distinguishing volitional control vs. spontaneous random noise is tangible and quantifiable, relative to the normative signatures characterizing TD participants.

The naked eye misses these patterns; hence it is not surprising that heretofore the ASD phenomena have not been interpreted as a movement disorder. But movement is not just an output signal from the CNS to the PNS. Rather, the statistical information embedded in the returning peripheral afferent stream that self-produced movements generate (caused by the CNS) is a form of kinesthetic reafferent signal. This peripheral signal informs the central controllers the moment-by-moment accumulation of sensory evidence to predict with a degree of certainty the sensory consequences of impending decisions and actions (Von Holst et al. in *Perceptual Processing: Stimulus equivalence and pattern recognition* (ed P. C. Dodwell) 41-72 (Appleton-Century-Crofts, 1950)). Without a reliable and predictable movement-returning signal the continuous volitional control of one's actions are bound to be disrupted. The individual with ASD moves, but the moment-by-moment returning motor signal has high uncertainty, contributed by noise and randomness in the fluctuations. These factors could contribute to aberrant sensory and motor integration and exacerbate social impairments defining the ASD behavioral phenotype. In this regard, sensory issues have been previously reported in ASD (Dinstein et al. (2012) Neuron 75:981-991) along with synaptic dysfunction (Zoghbi et al. (2012) CSH Perspectives Biol., 4:doi:10.1101/cshperspect.a009886; Shcheglovitov et al. (2013) Nature 503:267-271). The corrupted kinesthetic motor reafference may stem in part from synaptic dysfunction putatively producing specific patterns of sensory-motor noise.

The medications reported in the ABIDE study-sites are those commonly used to treat symptoms of ASD. They are noted to have motor side effects, including tremors, dyskinesias, involuntary ticks and other motor disorders in adult populations. A form of monitoring that relies on self-report therefore poses a substantial risk to the patient, particularly to the children, because these effects and drug interactions are not well understood for the young developing nervous systems at the peak of their plasticity. Here it is shown that as a group, there are medication classes that seem especially detrimental as they pull the individuals in the ASD group away from the normative TD signatures of head micro-movements; while others either improve towards the TD controls or show no differences from non-medicated ASD participants. Because the physiological system in individuals with ASD is a coping one (i.e., it may develop subtle over-compensatory mechanisms including those invisible to the naked eye) an advanced quantitative approach may be especially sensitive to detect potential minute changes in movement signatures as a function of medication and age. It will be useful to report in shared national databases how long each person has been under a particular treatment as well as the dosage information so as to assess precise interaction effects over time. Given the (cross-sectional) findings, these new types of personalized statistical approaches have the potential to enable identification of treatments that benefit the person maximally and retain gains over time vs. treatments that place the person at risk or have only transient effects.

There are no specific target drugs for autism yet. Medications that were developed for other disorders are prescribed to the autistic person to try and alleviate some symptoms. The high susceptibility to medications and the specificity within some groups to an increase (or decrease in others) of noise and randomness of the motor patterns found here in the ABIDE dataset indicates that some form of pattern identification may already be possible in the autistic population. The motor noise signatures within each autistic individual can lead to identification of different sub-classes of putative target molecular pathways across the spectrum, particularly if it was possible to identify a subset of highly susceptible individuals to specific drug classes for which the working mechanisms are well understood. This is a different form of precision phenotyping in ASD that through the use of Big Data may help link the coarse behavioral descriptors defining the symptom-based ASD phenotype today with genetic factors directly affecting synaptic noise along specific molecular pathways (Wilson et al. (2003) J. Med. Genet., 40:575-584; Phelan et al. (2001) Am. J. Med. Genet., 101:91-99; Roussignol et al. (2005) J. Neurosci., 25:3560-

3570). The present findings make this a testable hypothesis, introducing a new form of dynamic assessment to track the system as it copes with the disorder, as it is treated and as it reacts to various interventions.

The sensitivity to subtle changes in motor patterns invites the use of these methods in drug development and testing. The development and marketing of a new drug is a lengthy, costly and risky process. No proper methods exist today to detect early in Phase 1 the extent to which the trial may be risky in general as well as to estimate side effects for a given individual. Often the transition to a subsequent phase may proceed as evaluators of the efficacy report tend to report positive results. By the time that problems are visibly detectable by eye and the trial stopped, large resources may have already been spent. Once the drug is approved and goes to the market, physicians must rely on the patients' self-reports or on the reports from the caregivers on the immediate adverse effects from the combination-treatments or as they manifest between sporadic visits. Even when clinical trials evaluation of an approved drug is performed to assess the treatment to some of the symptoms in autism, the use of videotaping or other forms of motion tracking yields data that is currently analyzed under assumptions of normality of the motion parameter data and relying entirely on human heuristics and interpretation.

The non-Gaussian nature of motion data parameters indicates that typical analytic approaches that assume normality or 'detrend' nuisance patterns in the kinematics data may instead discard biologically valid signal (i.e., considered superfluous 'noise', as shown here). Therefore, the findings have important implications for the choice of analytical techniques used in autism research, research involving clinical trials of drugs approved for other disorders and more generally for drug development in animal models, as they too use methods that primarily rely on explicit heuristics.

The stochastic signatures of micro-movements taps into core biological features of neurodevelopmental disorders such as ASD, and is amenable to constitute one of the dimensions of the RDoC that cuts across research domains (Bernard et al. (2015) Psychol. Med., 1-5). The statistical sensitivity of these signatures to specific effects from different medication classes opens the possibility of combining this dimension with other domains of research and treatments to capture interactions in other neurological disorders. Specifically, in the present study the existing clinical classification was used as the basis for performing comparisons. However, the same methods could be used to blindly identify self-emerging clusters as a function of interaction of medication classes and the rates of change in stochastic signatures across different pathologies.

The results also indicate that the magnitude of the micro-motions in ASD may not be the relevant factor for noise cancellation. Rather, it is the stochasticity and accumulation rates that fundamentally differentiate the ASD from controls. Eliminating the scans with higher values of the head motions may not entirely resolve the problem of micro-motions contamination in imaging research (Power et al. (2012) Neuroimage 59:2142-2154; Satterthwaite et al. (2013) Neuroimage 64:240-256). It would be useful instead to apply the current methods to parameterize the stochastic signatures of each person recorded outside the magnet first. For example, by simply asking the individual to lie down still as he would inside the magnet, and then using the empirically estimated statistical signatures one could dynamically cancel out the motor noise once in the magnet. This would represent a statistically well-informed personalized online cancellation routine tailored to anticipate the specific stochastic signatures of each individual's impending micro-motions (Torres, E. B. (2013) Behavioral and Brain Functions 9:10). Instead of a 'one size fits all' static approach applied to the entire population one could have 'prospective' motion correction during acquisition of functional as well as structural MRI (Thesen et al. (2000) Magn. Reson. Med., 44:457-465; Tisdall et al. (2012) Magn. Reson. Med., 68:389-399). An individualized dynamic-stochastic approach would be particularly useful to the emerging field of precision psychiatry by providing this new form of precision phenotyping.

The present results can be translated into the clinic by using a combination of wearable sensing devices (for example, attached to the head, trunk, hand, arm, foot, ankle, and limbs) and the dynamic biometrics presented here. A participant with a neurodevelopmental disorder could be measured continuously at home and in the clinic using any of the commercially available technology specifically adapted to medication intake. Currently such devices (Apple watch, fitbits, etc.) measure motion patterns and patterns from other physiological signals. The same statistical platform presented here for the characterization of head-micro-motions can be used to profile the micro-motion patterns of such physiological signals and their fluctuations and rates of change unique to the person. This quantitative information would assist physicians in reaching the decision on whether or not to alter the psychopharmacological regimen according to the personalized longitudinal assessment of each patient in relation to his/her own patterns from previous visits. It would also allow insurance companies to draw a conclusion on coverage based on an objective outcome measure automatically revealing trends in the person's signatures.

The results from these analyses demonstrate the extreme usefulness of big data made publicly available to the scientific community. Combined with proper analytics this information paves the way towards a transformative path in conceptualization, diagnosis, treatment and tracking of mental illnesses. The micro-motions disturbances revealed by these data sets—data that are a nuisance to others—turned out to contain a wealth of information that helps unravel the puzzle of autism spectrum disorders. In this sense, characterizing micro-motor noise in controls and casting the micro-motor noise in autism relative to the normative data helped see the fundamental statistical differences between these groups as well as the effects of medication in the ASD cohorts. Medication intake in the presence of objective knowledge of sensory-motor consequences would allow a more personalized and safer approach towards treatment of individuals with neurodevelopmental disorders. Micro-motor-noise-driven data analyses in ASD is key to more than one line of future inquiries at the intersection of personalized neuroimaging research, the personalized assessments of pharmacological treatments, as well as the detection and objective profiling of motor noise disorders across neurodevelopment and beyond.

FIG. 19 depicts an example of internal hardware that may be included in any of the electronic components of the system such as the computing device 130 (in FIG. 1). An electrical bus 900 serves as an information highway interconnecting the other illustrated components of the hardware. Processor 905 is a central processing device of the device, configured to perform calculations and logic operations required to execute programming instructions. As used in this document and in the claims, the terms "processor" and "processing device" may refer to a single processor or any number of processors or processor cores in one or more processors. The device may include read only memory (ROM) 910, random access memory (RAM) 915, or other types of memory devices 925, such as flash memory, hard drives and other devices capable of storing electronic data. A memory device may include a single device or a collection of devices across which data and/or instructions are stored An optional display interface 930 may permit information from the bus 900 to be displayed on a display device 935 in visual, graphic or alphanumeric format. An audio interface and audio output (such as a speaker) also may be provided. Communication with external devices and/or sensors, such as motion sensors or biometric sensors, may occur using various communication ports or devices 940 such as a portable memory device reader/writer, a transmitter and/or receiver, an antenna, an RFID tag and/or short-range or near-field communication circuitry. The communication device 940 may be attached to a communications network, such as the Internet, a local area network or a cellular telephone data network.

The hardware may also include a user interface sensor 945 that allows for receipt of data from input devices 955 such as a keyboard 950, a mouse, a joystick, a touchscreen, a remote control, a pointing device, a video input device (camera) and/or an audio input device (microphone). Various methods of activation, validation and/or authorization described in this document may be performed by the central processing device 905 or a controller 920.

While certain of the preferred embodiments of the present invention have been described and specifically exemplified above, it is not intended that the invention be limited to such embodiments. Various modifications or combinations may be made thereto without departing from the scope and spirit of the present invention, as set forth in the following claims.

What is claimed is:

1. A system for identifying a physiologically relevant biorhythm of a subject, comprising:
    at least a motion sensor configured to sense movement of a first body part of the subject and configured to measure micromovement of the subject and produce a time series of micromovement data representing the micromovement of the subject over a period of time, wherein the micromovement is movement at or below a millisecond and millimeter scale;
    at least a biometric sensor attachable to a second body part of the subject and configured to measure simultaneously a non-motion biometric of the subject and produce a time series of biometric values of the subject over the period of time;
    a processing device; and
    a computer readable medium containing programming instructions that, when executed, will cause the processing device to:
    determine a noise-to-signal ratio based on the time series of micromovement data for each of a plurality of time intervals within the period of time and for each of a plurality of ranges of values of the biometric in the time series of biometric values, and
    identify as a physiologically relevant biorhythm at least a portion of the time series of micromovement data, wherein the portion is defined by at least one range of the plurality of ranges of values for the biometric and at least one time interval of the plurality of time intervals, and the noise-to-signal ratio determined for the portion is lower than 50% of all the noise-to-signal ratios determined.

2. The system of claim 1, wherein the motion sensor is an inertial measure unit (IMU) sensor attachable to the first body part of the subject.

3. The system of claim 2, wherein the motion sensor is configured to be attached to one of the following: a head, trunk, or limb that includes a hand, foot, an arm or ankle of the subject.

4. The system of claim 1, wherein the biometric sensor is one of the following: a thermometer, an electroencephalogram (EEG), an electromyography (EMG), a stethoscope or a heart rate monitor.

5. The system of claim 1, wherein the time series of micromovement data include one or more of the following: a velocity, an acceleration, a speed profile, a max speed, a max acceleration, a minimum speed, a minimum acceleration, a time to reach maximum speed, a time to reach maximum acceleration, a max retraction speed, a time to reach max retraction speed, an inter-peak intervals, a three-dimensional path, an accuracy of target touching, an overall amount of time for motion, a rotation or positioning, a translational movement, a rotational movement, or a joint angle.

6. The system of claim 1, wherein the programming instructions comprise additional programming instructions configured to cause the processing device to:
    analyze motion fluctuation in the portion of the time series of micromovement data that correspond to the physiologically relevant biorhythm to determine a rate of change of the noise-to-signal ratio for each biometric interval; and
    use the rate of change to determine whether the physiological relevant biorhythm at each of the plurality of ranges of values for the biometric is systematic or spontaneously random.

7. The system of claim 6, wherein the time series of micromovement data include an acceleration and the biometric values include a temperature, and the programming instructions for determining the rate of change of the noise-to-signal ratio comprise programming instructions configured to cause the processing device to:
    estimate parameters of a continuous Gamma distribution family based on the portion of the series of movement data at each of the plurality of ranges of values for the biometric;
    determine a shape parameter of the continuous Gamma distribution; and
    determine a rate of change of the shape parameter of the continuous Gamma distribution.

8. The system of claim 1, wherein the motion sensor is a functional magnetic resonance imaging (fMRI) device configured to collect a sequence of images of a head of the subject over the period of time.

9. The system of claim 8, wherein the programming instructions for producing the time series of micromovement data representing the micromovement of the subject comprise programming instructions configured to use a motion estimate method to estimate a micromovement of the head of the subject over the period of time.

10. The system of claim 1, further comprising a display, wherein the programming instructions for identifying the portion of the time series of micromovement data as corresponding to a physiologically relevant biorhythm comprise programming instructions configured to display a three-dimensional matrix on the display, the three-dimensional matrix comprising a plurality of cells in a two-dimensional plane corresponding, in which:
    a first dimension is the plurality of time intervals;
    a second dimension is the plurality of ranges of values for the biometric; and each of the plurality of cells is coded by a color or a gray scale that represents a maximal deviation from a mean acceleration of the time series of micromovement data for a portion.

11. The system of claim 10, wherein the first dimension has a sampling resolution which is the same as a sample resolution of the motion sensor.

12. The system of claim 10, wherein the second dimension comprises a heart-rate or a temperature.

13. A method of identifying a physiologically relevant biorhythm of a subject;
said method comprising:
a) measuring, by a motion sensor, micromovement of a subject and producing a time series of micromovement data representing the micromovement of the subject over a period of time, wherein the micromovement is movement at or below a millisecond and millimeter scale;
b) measuring simultaneously, by a biometric sensor configured to be attached to a body part of the subject, a non-motion biometric of the subject and producing a time series of biometric values of the subject over the period of time;
c) determining, by a processing device, a noise-to-signal ratio based on the time series of micromovement data for each of a plurality of time intervals within the period of time and for each of a plurality of ranges of values of the biometric in the time series of biometric values; and
d) identifying, by the processing device, as a physiologically relevant biorhythm at least a portion of the time series of micromovement data, wherein the portion is defined by at least one range of the plurality of ranges of values for the biometric and at least one time interval of the plurality of time intervals, and the noise-to-signal ratio determined for the portion is lower than 50% of all the noise-to-signal ratios determined.

14. The method of claim 13, wherein the motion sensor is attached to one of the following: a head, trunk, or limb that includes a hand, foot, an arm or ankle, of the subject.

15. The method of claim 13, wherein the biometric value is one of the following: temperature, breathing rate or heartbeat rate of the subject.

16. The method of claim 13, wherein the time series of micromovement data include one or more of the following: a velocity, an acceleration, a speed profile, a max speed, a max acceleration, a minimum speed, a minimum acceleration, a time to reach maximum speed, a time to reach maximum acceleration, a max retraction speed, a time to reach max retraction speed, an inter-peak intervals, a three-dimensional path, an accuracy of target touching, an overall amount of time for motion, a rotation or positioning, a translational movement, a rotational movement, or a joint angle.

17. The method of claim 13, further comprising, by the processing device:
analyzing motion fluctuation in the portion of the time series of micromovement data that correspond to the physiologically relevant biorhythm to determine a rate of change of the noise-to-signal ratio for each biometric interval;
using the rate of change to determine whether the physiological relevant biorhythm at each of the plurality of ranges of values for the biometric is systematic or spontaneously random.

18. The method of claim 17, wherein the time series of micromovement data include an acceleration and the biometric values include a temperature, and determining the rate of change of the noise-to-signal ratio comprises:
estimating parameters of a continuous Gamma distribution family based on the portion of the series of movement data at each of the plurality of ranges of values for the biometric;
determining a shape parameter of the continuous Gamma distribution; and
determining a rate of change of the shape parameter of the continuous Gamma distribution.

19. The method of claim 13, wherein measuring the movement of the subject comprises capturing and collecting a sequence of images of a head of the subject over the period of time from a functional magnetic resonance imaging (fMRI) device.

20. The method of claim 19, wherein producing the time series of micromovement data representing the micromovement of the subject comprises using a motion estimate method to estimate a micromovement of the head of the subject over the period of time.

21. The method of claim 13, wherein identifying the portion of the time series of micromovement data as corresponding to a physiologically relevant biorhythm comprising displaying a three-dimensional matrix on a display, the three-dimensional matrix comprising a plurality of cells in a two-dimensional plane, in which:
a first dimension is the plurality of time intervals;
a second dimension is the plurality of ranges of values for the biometric; and
each of the plurality of cells is coded by a color or a gray scale that represents a maximal deviation from a mean acceleration of the time series of micromovement data for a portion.

22. The method of claim 21, wherein the first dimension has a sampling resolution of the motion sensor.

23. The method of claim 21, wherein the second dimension comprises a heart-rate or a temperature.

\* \* \* \* \*